(12) United States Patent
Michlitsch et al.

(10) Patent No.: US 7,955,340 B2
(45) Date of Patent: Jun. 7, 2011

(54) APPARATUS AND METHODS FOR FORMING AND SECURING GASTROINTESTINAL TISSUE FOLDS

(75) Inventors: Kenneth J. Michlitsch, Livermore, CA (US); Vahid C. Saadat, Saratoga, CA (US); Richard C. Ewers, Fullerton, CA (US); Chris Rothe, San Jose, CA (US); Rodney Brenneman, San Juan Capistrano, CA (US); Cang C. Lam, Irvine, CA (US); Eugene C. Chen, Carlsbad, CA (US)

(73) Assignee: USGI Medical, Inc., San Clemente, CA (US)

( * ) Notice: Subject to any disclaimer, the term of this patent is extended or adjusted under 35 U.S.C. 154(b) by 1327 days.

(21) Appl. No.: 10/734,562

(22) Filed: Dec. 12, 2003

(65) Prior Publication Data
US 2004/0225183 A1 Nov. 11, 2004

Related U.S. Application Data

(63) Continuation-in-part of application No. 10/672,375, filed on Sep. 25, 2003, now Pat. No. 7,416,554, and a continuation-in-part of application No. 10/612,170, filed on Jul. 1, 2003, and a continuation-in-part of application No. 10/639,162, filed on Aug. 11, 2003, now Pat. No. 7,618,426, and a continuation-in-part of application No. 10/173,203, filed on Jun. 13, 2002, now Pat. No. 7,128,708, and a continuation-in-part of application No. 10/458,060, filed on Jun. 9, 2003, now abandoned, which is a continuation-in-part of application No. 10/346,709, filed on Jan. 15, 2003, now Pat. No. 7,637,905, application No. 10/734,562, which is a continuation-in-part of application No. 10/288,619, filed on Nov. 4, 2002, now Pat. No. 7,160,312, which is a continuation-in-part of application No. 09/746,579, filed on Dec. 20, 2000, now Pat. No. 6,991,643, application No. 10/734,562, which is a continuation-in-part of application No. 10/188,509, filed on Jul. 3, 2002, now Pat. No. 7,186,262, which is a continuation-in-part of application No. 09/898,726, filed on Jul. 3, 2001, now Pat. No. 6,626,899, which is a continuation-in-part of application No. 09/602,436, filed on Jun. 23, 2000, now Pat. No. 6,669,687.

(60) Provisional application No. 60/500,627, filed on Sep. 5, 2003, provisional application No. 60/433,065, filed on Dec. 11, 2002, provisional application No. 60/471,893, filed on May 19, 2003, provisional application No. 60/141,077, filed on Jun. 25, 1999.

(51) Int. Cl.
 *A61B 17/10* (2006.01)
 *A61B 17/08* (2006.01)
 *A61B 1/00* (2006.01)

(52) U.S. Cl. ......... 606/139; 606/153; 600/104; 600/141

(58) Field of Classification Search .................. 600/104, 600/114, 118, 125, 131, 139, 141, 143, 144, 600/153; 606/108, 139, 144, 148, 151, 153, 606/157, 158, 213, 215–217, 228, 232
See application file for complete search history.

(56) References Cited

U.S. PATENT DOCUMENTS

| | | | |
|---|---|---|---|
| 616,672 A | 12/1898 | Kelling | |
| 2,201,610 A | 5/1940 | Dawson, Jr. | |
| 2,413,142 A | 12/1945 | Jones et al. | |
| 2,510,198 A | 6/1950 | Tesmer | |
| 2,533,494 A | 12/1950 | Mitchell, Jr. | |
| 3,060,972 A * | 10/1962 | Sheldon | 138/120 |
| 3,096,962 A | 7/1963 | Meijs | |
| 3,150,379 A | 9/1964 | Brown | |
| 3,162,214 A * | 12/1964 | Bazinet, Jr. | 138/120 |
| 3,166,072 A | 1/1965 | Sullivan, Jr. | |
| 3,168,274 A | 2/1965 | Street | |
| 3,190,286 A * | 6/1965 | Stokes | 600/141 |
| 3,266,059 A | 8/1966 | Stelle | |
| 3,430,662 A | 3/1969 | Guarnaschelli | |
| 3,494,006 A | 2/1970 | Brumlik | |
| 3,546,961 A * | 12/1970 | Marton | 74/502.5 |
| 3,551,987 A | 1/1971 | Wilkinson | |

| Patent No. | | Date | Inventor(s) |
|---|---|---|---|
| 3,583,393 A | | 6/1971 | Takahashi |
| 3,643,653 A | * | 2/1972 | Takahashi et al. ............ 600/129 |
| 3,646,615 A | | 3/1972 | Ness |
| 3,664,345 A | | 5/1972 | Dabbs et al. |
| 3,753,438 A | | 8/1973 | Wood et al. |
| 3,835,841 A | | 9/1974 | Terada |
| 3,858,578 A | | 1/1975 | Milo |
| 3,867,944 A | | 2/1975 | Samuels |
| 3,874,388 A | | 4/1975 | King et al. |
| 3,910,281 A | | 10/1975 | Kletschka et al. |
| 3,913,565 A | | 10/1975 | Kawahara |
| 3,915,157 A | | 10/1975 | Mitsui |
| 3,948,251 A | | 4/1976 | Hosono |
| 3,974,834 A | | 8/1976 | Kane |
| 3,976,079 A | | 8/1976 | Samuels et al. |
| 4,006,747 A | | 2/1977 | Kronenthal et al. |
| 4,007,743 A | | 2/1977 | Blake |
| 4,036,218 A | | 7/1977 | Yamashita et al. |
| 4,054,128 A | * | 10/1977 | Seufert et al. .................. 600/116 |
| 4,060,089 A | | 11/1977 | Noiles |
| 4,069,825 A | | 1/1978 | Akiyama |
| 4,176,662 A | | 12/1979 | Frazer |
| 4,201,198 A | | 5/1980 | Okada et al. |
| 4,224,929 A | | 9/1980 | Furihata |
| 4,235,238 A | | 11/1980 | Ogiu et al. |
| 4,245,624 A | | 1/1981 | Komiya |
| 4,259,959 A | | 4/1981 | Walker |
| 4,366,810 A | | 1/1983 | Slanetz, Jr. |
| 4,367,746 A | | 1/1983 | Derechinsky |
| 4,414,720 A | | 11/1983 | Crooms |
| 4,462,402 A | | 7/1984 | Burgio |
| 4,494,531 A | | 1/1985 | Gianturco |
| 4,532,926 A | | 8/1985 | O'Holla |
| 4,534,350 A | | 8/1985 | Golden et al. |
| 4,548,202 A | | 10/1985 | Duncan |
| 4,577,621 A | | 3/1986 | Patel |
| 4,586,503 A | | 5/1986 | Kirsch et al. |
| 4,592,339 A | | 6/1986 | Kuzmak et al. |
| 4,592,356 A | | 6/1986 | Gutierrez |
| 4,595,007 A | | 6/1986 | Mericle |
| 4,601,283 A | | 7/1986 | Chikama |
| 4,610,250 A | | 9/1986 | Green |
| 4,624,243 A | | 11/1986 | Lowery et al. |
| 4,646,722 A | | 3/1987 | Silverstein et al. |
| 4,648,733 A | | 3/1987 | Merkt |
| 4,651,718 A | | 3/1987 | Collins et al. |
| 4,655,257 A | * | 4/1987 | Iwashita ....................... 138/120 |
| 4,669,473 A | | 6/1987 | Richards et al. |
| 4,700,693 A | * | 10/1987 | Lia et al. ........................ 600/141 |
| 4,705,040 A | | 11/1987 | Mueller et al. |
| 4,711,002 A | | 12/1987 | Kreeger |
| 4,724,840 A | | 2/1988 | McVay et al. |
| 4,745,908 A | | 5/1988 | Wardle |
| 4,748,959 A | | 6/1988 | Cook et al. |
| 4,750,492 A | | 6/1988 | Jacobs |
| 4,765,335 A | | 8/1988 | Schmidt et al. |
| 4,790,294 A | * | 12/1988 | Allred et al. ................... 600/141 |
| 4,815,450 A | | 3/1989 | Patel |
| 4,832,055 A | | 5/1989 | Palestrant |
| 4,841,888 A | | 6/1989 | Mills et al. |
| 4,869,238 A | | 9/1989 | Opie et al. |
| 4,872,579 A | | 10/1989 | Palmer |
| 4,873,976 A | | 10/1989 | Schreiber |
| 4,890,615 A | | 1/1990 | Caspari et al. |
| 4,923,461 A | | 5/1990 | Caspari et al. |
| 4,929,240 A | | 5/1990 | Kirsch et al. |
| 4,949,927 A | | 8/1990 | Madocks et al. |
| 4,957,498 A | | 9/1990 | Caspari et al. |
| 4,988,171 A | | 1/1991 | Yokota |
| 5,000,683 A | | 3/1991 | Brock |
| 5,005,558 A | | 4/1991 | Aomori |
| 5,015,249 A | | 5/1991 | Nakao et al. |
| 5,020,539 A | | 6/1991 | Yokoi et al. |
| 5,025,778 A | | 6/1991 | Silverstein et al. |
| 5,032,127 A | | 7/1991 | Frazee et al. |
| 5,035,231 A | | 7/1991 | Kubokawa et al. |
| 5,035,692 A | | 7/1991 | Lyon et al. |
| 5,037,433 A | | 8/1991 | Wilk et al. |
| 5,041,129 A | | 8/1991 | Hayhurst et al. |
| 5,059,201 A | | 10/1991 | Asnis |
| 5,068,719 A | | 11/1991 | Tsuji |
| 5,073,166 A | | 12/1991 | Parks et al. |
| 5,088,979 A | | 2/1992 | Filipi et al. |
| 5,092,901 A | | 3/1992 | Hunter et al. |
| 5,099,827 A | | 3/1992 | Melzer et al. |
| 5,100,418 A | | 3/1992 | Yoon et al. |
| 5,108,420 A | | 4/1992 | Marks |
| 5,122,136 A | | 6/1992 | Guglielmi et al. |
| 5,123,914 A | | 6/1992 | Cope |
| RE34,021 E | | 8/1992 | Mueller et al. |
| 5,170,775 A | | 12/1992 | Tagami |
| 5,172,225 A | | 12/1992 | Takahashi |
| 5,174,276 A | * | 12/1992 | Crockard ....................... 600/104 |
| 5,176,691 A | | 1/1993 | Pierce |
| 5,179,935 A | * | 1/1993 | Miyagi .......................... 600/142 |
| 5,187,572 A | | 2/1993 | Nakamura et al. |
| 5,196,928 A | | 3/1993 | Karasawa et al. |
| 5,201,746 A | | 4/1993 | Shichman |
| 5,203,864 A | | 4/1993 | Phillips |
| 5,217,001 A | | 6/1993 | Nakao et al. |
| 5,217,471 A | | 6/1993 | Burkhart |
| 5,217,473 A | | 6/1993 | Yoon |
| 5,222,508 A | | 6/1993 | Contarini |
| 5,222,961 A | | 6/1993 | Nakao et al. |
| 5,222,963 A | | 6/1993 | Brinkerhoff et al. |
| 5,224,946 A | | 7/1993 | Hayhurst et al. |
| 5,234,430 A | | 8/1993 | Huebner |
| 5,234,445 A | | 8/1993 | Walker et al. |
| 5,250,053 A | | 10/1993 | Snyder |
| 5,251,611 A | | 10/1993 | Zehel et al. |
| 5,254,126 A | | 10/1993 | Filipi et al. |
| 5,261,916 A | | 11/1993 | Engelson |
| 5,268,001 A | | 12/1993 | Nicholson et al. |
| 5,271,381 A | * | 12/1993 | Ailinger et al. ................ 600/128 |
| 5,275,608 A | | 1/1994 | Forman et al. |
| 5,282,827 A | | 2/1994 | Kensey et al. |
| 5,284,488 A | | 2/1994 | Sideris |
| 5,289,817 A | | 3/1994 | Williams et al. |
| 5,304,184 A | | 4/1994 | Hathaway et al. |
| 5,304,195 A | | 4/1994 | Twyford, Jr. et al. |
| 5,304,204 A | | 4/1994 | Bregen |
| 5,316,543 A | | 5/1994 | Eberbach |
| 5,318,528 A | | 6/1994 | Heaven et al. |
| 5,325,845 A | | 7/1994 | Adair |
| 5,327,914 A | | 7/1994 | Shlain |
| 5,330,503 A | | 7/1994 | Yoon |
| 5,334,217 A | | 8/1994 | Das |
| 5,337,732 A | | 8/1994 | Grundfest et al. |
| 5,337,733 A | | 8/1994 | Bauerfeind et al. |
| 5,342,376 A | | 8/1994 | Ruff |
| 5,345,949 A | | 9/1994 | Shlain |
| 5,348,259 A | | 9/1994 | Blanco et al. |
| 5,354,298 A | | 10/1994 | Lee et al. |
| 5,366,459 A | | 11/1994 | Yoon |
| 5,366,479 A | | 11/1994 | McGarry et al. |
| 5,372,146 A | | 12/1994 | Branch |
| 5,372,604 A | | 12/1994 | Trott |
| 5,374,275 A | | 12/1994 | Bradley et al. |
| 5,380,334 A | | 1/1995 | Torrie et al. |
| 5,382,231 A | * | 1/1995 | Shlain ........................... 128/898 |
| 5,383,897 A | | 1/1995 | Wholey |
| 5,395,030 A | | 3/1995 | Kuramoto et al. |
| 5,395,367 A | | 3/1995 | Wilk |
| 5,397,304 A | | 3/1995 | Truckai |
| 5,402,768 A | | 4/1995 | Adair |
| 5,403,326 A | * | 4/1995 | Harrison et al. ............... 606/139 |
| 5,403,329 A | | 4/1995 | Hinchcliffe |
| 5,417,691 A | | 5/1995 | Hayhurst |
| 5,417,699 A | | 5/1995 | Klein et al. |
| 5,423,885 A | | 6/1995 | Williams |
| 5,425,744 A | | 6/1995 | Fagan et al. |
| 5,429,118 A | | 7/1995 | Cole et al. |
| 5,429,598 A | | 7/1995 | Waxman et al. |
| 5,431,666 A | | 7/1995 | Sauer et al. |
| 5,433,721 A | | 7/1995 | Hooven et al. |
| 5,433,727 A | | 7/1995 | Sideris |
| 5,437,266 A | | 8/1995 | McPherson et al. |
| 5,437,680 A | | 8/1995 | Yoon |

| | | | | | | |
|---|---|---|---|---|---|---|
| 5,437,681 A | 8/1995 | Meade et al. | | 5,702,397 A | 12/1997 | Goble et al. |
| 5,441,499 A | 8/1995 | Fritzsch | | 5,702,421 A | 12/1997 | Schneidt |
| 5,445,167 A | 8/1995 | Yoon et al. | | 5,704,898 A * | 1/1998 | Kokish ................... 600/141 |
| 5,448,989 A | 9/1995 | Heckele | | 5,707,394 A | 1/1998 | Miller et al. |
| 5,458,609 A | 10/1995 | Gordon et al. | | 5,709,708 A | 1/1998 | Thal |
| 5,462,560 A | 10/1995 | Stevens | | 5,713,903 A | 2/1998 | Sander et al. |
| 5,462,561 A | 10/1995 | Voda | | 5,720,765 A | 2/1998 | Thal |
| 5,465,894 A | 11/1995 | Clark et al. | | 5,724,978 A | 3/1998 | Tenhoff |
| 5,470,337 A | 11/1995 | Moss | | 5,725,552 A | 3/1998 | Kotula et al. |
| 5,470,338 A | 11/1995 | Whitfield et al. | | 5,728,045 A | 3/1998 | Komi |
| 5,476,470 A | 12/1995 | Fitzgibbons, Jr. | | 5,732,707 A | 3/1998 | Widder et al. |
| 5,478,354 A | 12/1995 | Tovey et al. | | 5,741,297 A | 4/1998 | Simon |
| 5,480,405 A | 1/1996 | Yoon | | 5,741,429 A | 4/1998 | Donadio et al. |
| 5,482,029 A | 1/1996 | Sekiguchi et al. | | 5,746,752 A | 5/1998 | Burkhart |
| 5,496,332 A | 3/1996 | Sierra et al. | | 5,746,755 A | 5/1998 | Wood et al. |
| 5,496,334 A | 3/1996 | Klundt et al. | | 5,749,828 A * | 5/1998 | Solomon et al. ............ 600/141 |
| 5,499,991 A | 3/1996 | Garman et al. | | 5,749,893 A | 5/1998 | Vidal et al. |
| 5,501,691 A | 3/1996 | Goldrath | | 5,752,963 A | 5/1998 | Allard et al. |
| 5,507,811 A | 4/1996 | Koike et al. | | 5,759,151 A | 6/1998 | Sturges |
| 5,520,691 A | 5/1996 | Branch | | 5,766,169 A | 6/1998 | Fritzsch et al. |
| 5,520,701 A | 5/1996 | Lerch | | 5,766,189 A | 6/1998 | Matsuno |
| 5,522,843 A | 6/1996 | Zang | | 5,772,597 A | 6/1998 | Goldberger et al. |
| 5,527,321 A | 6/1996 | Hinchliffe | | 5,776,150 A | 7/1998 | Nolan et al. |
| 5,527,322 A | 6/1996 | Klein et al. | | 5,779,624 A | 7/1998 | Chang |
| 5,527,342 A | 6/1996 | Pietrzak et al. | | 5,779,719 A | 7/1998 | Klein et al. |
| 5,531,759 A | 7/1996 | Kensey et al. | | 5,782,859 A | 7/1998 | Nicholas et al. |
| 5,531,788 A | 7/1996 | Dibie et al. | | 5,782,865 A | 7/1998 | Grotz |
| 5,540,704 A | 7/1996 | Gordon et al. | | 5,787,897 A | 8/1998 | Kieturakis |
| 5,549,618 A | 8/1996 | Fleenor et al. | | 5,792,152 A | 8/1998 | Klein et al. |
| 5,549,621 A | 8/1996 | Bessler et al. | | 5,792,153 A | 8/1998 | Swain et al. |
| 5,558,665 A | 9/1996 | Kieturakis | | 5,797,929 A | 8/1998 | Andreas et al. |
| 5,562,684 A | 10/1996 | Kammerer | | 5,797,960 A | 8/1998 | Stevens et al. |
| 5,562,686 A | 10/1996 | Sauer et al. | | 5,807,241 A | 9/1998 | Heimberger |
| 5,562,688 A | 10/1996 | Riza | | 5,810,849 A | 9/1998 | Kontos |
| 5,569,274 A | 10/1996 | Rapacki et al. | | 5,810,851 A | 9/1998 | Yoon |
| 5,569,306 A | 10/1996 | Thal | | 5,810,853 A | 9/1998 | Yoon |
| 5,571,116 A | 11/1996 | Bolanos et al. | | 5,810,882 A | 9/1998 | Bolduc et al. |
| 5,571,119 A | 11/1996 | Atala | | 5,814,064 A | 9/1998 | Daniel et al. |
| 5,573,496 A | 11/1996 | McPherson et al. | | 5,814,070 A | 9/1998 | Borzone et al. |
| 5,573,540 A | 11/1996 | Yoon | | 5,817,107 A | 10/1998 | Schaller |
| 5,573,548 A | 11/1996 | Nazre et al. | | 5,817,110 A | 10/1998 | Kronner |
| 5,575,801 A | 11/1996 | Habermeyer et al. | | 5,823,956 A | 10/1998 | Roth et al. |
| 5,578,045 A | 11/1996 | Das | | 5,824,011 A | 10/1998 | Stone et al. |
| 5,582,577 A | 12/1996 | Lund et al. | | 5,827,298 A | 10/1998 | Hart et al. |
| 5,582,616 A | 12/1996 | Bolduc et al. | | 5,829,447 A | 11/1998 | Stevens et al. |
| 5,584,835 A | 12/1996 | Greenfield | | 5,836,955 A | 11/1998 | Buelna et al. |
| 5,584,859 A | 12/1996 | Brotz | | 5,840,078 A | 11/1998 | Yerys |
| 5,601,557 A | 2/1997 | Hayhurst | | 5,842,973 A | 12/1998 | Bullard |
| 5,603,718 A | 2/1997 | Xu | | 5,843,084 A | 12/1998 | Hart et al. |
| 5,613,974 A | 3/1997 | Andreas et al. | | 5,843,126 A | 12/1998 | Jameel |
| 5,613,975 A | 3/1997 | Christy | | 5,846,261 A | 12/1998 | Kotula et al. |
| 5,620,408 A | 4/1997 | Vennes et al. | | 5,855,614 A | 1/1999 | Stevens et al. |
| 5,624,380 A | 4/1997 | Takayama et al. | | 5,860,991 A | 1/1999 | Klein et al. |
| 5,624,381 A * | 4/1997 | Kieturakis ................ 600/206 | | 5,861,003 A | 1/1999 | Latson et al. |
| 5,626,588 A | 5/1997 | Sauer et al. | | 5,865,791 A | 2/1999 | Whayne et al. |
| 5,626,614 A | 5/1997 | Hart | | 5,868,760 A | 2/1999 | McGuckin, Jr. |
| 5,630,540 A | 5/1997 | Blewett | | 5,868,762 A | 2/1999 | Cragg et al. |
| 5,632,752 A | 5/1997 | Buelna | | 5,873,817 A * | 2/1999 | Kokish et al. ............... 600/143 |
| 5,643,274 A | 7/1997 | Sander et al. | | 5,879,371 A | 3/1999 | Gardiner et al. |
| 5,643,295 A | 7/1997 | Yoon | | 5,887,594 A | 3/1999 | LoCiero, III |
| 5,643,317 A | 7/1997 | Pavcnik et al. | | 5,888,247 A | 3/1999 | Benetti |
| 5,643,320 A | 7/1997 | Lower et al. | | 5,891,168 A | 4/1999 | Thal |
| 5,658,312 A | 8/1997 | Green et al. | | 5,893,856 A | 4/1999 | Jacobs et al. |
| 5,658,313 A | 8/1997 | Thal | | 5,895,404 A | 4/1999 | Ruiz |
| 5,662,587 A | 9/1997 | Grundfest et al. | | 5,897,417 A | 4/1999 | Grey |
| 5,662,654 A | 9/1997 | Thompson | | 5,897,562 A | 4/1999 | Bolanos et al. |
| 5,662,662 A | 9/1997 | Bishop et al. | | 5,899,920 A | 5/1999 | DeSatnick et al. |
| 5,662,663 A | 9/1997 | Shallman | | 5,899,921 A | 5/1999 | Caspari et al. |
| 5,665,109 A | 9/1997 | Yoon | | 5,901,895 A | 5/1999 | Heaton et al. |
| 5,665,112 A | 9/1997 | Thal | | 5,902,254 A | 5/1999 | Magram |
| 5,667,513 A | 9/1997 | Torrie et al. | | 5,904,647 A | 5/1999 | Ouchi |
| 5,676,670 A | 10/1997 | Kim | | 5,908,381 A | 6/1999 | Aznoian et al. |
| 5,676,674 A | 10/1997 | Bolanos et al. | | 5,916,146 A * | 6/1999 | Allotta et al. ............... 600/141 |
| 5,679,005 A | 10/1997 | Einstein | | 5,916,147 A * | 6/1999 | Boury ..................... 600/146 |
| 5,683,417 A | 11/1997 | Cooper | | 5,916,224 A | 6/1999 | Esplin |
| 5,683,419 A | 11/1997 | Thal | | 5,921,915 A | 7/1999 | Azonian et al. |
| 5,690,655 A | 11/1997 | Hart et al. | | 5,925,059 A | 7/1999 | Palermo et al. |
| 5,693,060 A | 12/1997 | Martin | | 5,928,260 A | 7/1999 | Chin et al. |
| 5,700,273 A | 12/1997 | Buelna et al. | | 5,928,264 A | 7/1999 | Sugarbaker et al. |

| | | | |
|---|---|---|---|
| 5,938,586 A | 8/1999 | Wilk et al. | |
| 5,941,815 A | 8/1999 | Chang | |
| 5,944,738 A | 8/1999 | Amplatz et al. | |
| 5,947,983 A | 9/1999 | Solar et al. | |
| 5,947,997 A | 9/1999 | Pavcnik et al. | |
| 5,948,001 A | 9/1999 | Larsen | |
| 5,954,731 A | 9/1999 | Yoon | |
| 5,954,732 A | 9/1999 | Hart et al. | |
| 5,954,733 A | 9/1999 | Yoon | |
| 5,957,937 A | 9/1999 | Yoon | |
| 5,961,440 A | 10/1999 | Schweich, Jr. et al. | |
| 5,964,765 A | 10/1999 | Fenton, Jr. et al. | |
| 5,964,782 A | 10/1999 | Lafontaine et al. | |
| 5,964,783 A | 10/1999 | Grafton et al. | |
| 5,976,127 A | 11/1999 | Lax | |
| 5,976,158 A | 11/1999 | Adams et al. | |
| 5,976,159 A | 11/1999 | Bolduc et al. | |
| 5,980,555 A | 11/1999 | Barbut et al. | |
| 5,980,558 A | 11/1999 | Wiley | |
| 5,984,932 A | 11/1999 | Yoon | |
| 5,984,933 A | 11/1999 | Yoon | |
| 5,993,466 A | 11/1999 | Yoon | |
| 5,993,467 A | 11/1999 | Yoon | |
| 5,993,476 A | 11/1999 | Groiso | |
| 6,013,083 A | 1/2000 | Bennett | |
| 6,017,358 A | 1/2000 | Yoon et al. | |
| 6,027,460 A | 2/2000 | Shturman | |
| 6,027,523 A | 2/2000 | Schmieding | |
| 6,033,430 A | 3/2000 | Bonutti | |
| 6,036,699 A | 3/2000 | Andreas et al. | |
| 6,042,155 A | 3/2000 | Lockwood | |
| 6,045,497 A | 4/2000 | Schweich, Jr. et al. | |
| 6,045,573 A | 4/2000 | Wenstrom, Jr. et al. | |
| 6,050,936 A | 4/2000 | Schweich, Jr. et al. | |
| 6,053,935 A | 4/2000 | Brenneman et al. | |
| 6,056,770 A | 5/2000 | Epstein et al. | |
| 6,059,715 A | 5/2000 | Schweich, Jr. et al. | |
| 6,059,719 A | 5/2000 | Yamamoto et al. | |
| 6,074,401 A | 6/2000 | Gardiner et al. | |
| 6,077,214 A | 6/2000 | Mortier et al. | |
| 6,077,281 A | 6/2000 | Das | |
| 6,077,291 A | 6/2000 | Das | |
| 6,079,414 A | 6/2000 | Roth et al. | |
| 6,086,600 A | 7/2000 | Kortenbach | |
| 6,086,601 A | 7/2000 | Yoon | |
| 6,099,464 A | 8/2000 | Shimizu et al. | |
| 6,110,183 A | 8/2000 | Cope | |
| 6,113,609 A * | 9/2000 | Adams | 606/139 |
| 6,113,611 A | 9/2000 | Allen et al. | |
| 6,119,913 A | 9/2000 | Adams et al. | |
| 6,149,658 A | 11/2000 | Gardiner et al. | |
| 6,152,870 A | 11/2000 | Diener | |
| 6,152,935 A | 11/2000 | Kammerer et al. | |
| 6,159,146 A * | 12/2000 | El Gazayerli | 600/106 |
| 6,159,224 A | 12/2000 | Yoon | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,167,889 B1 | 1/2001 | Benetti | |
| 6,171,235 B1 | 1/2001 | Konstorum et al. | |
| 6,171,320 B1 | 1/2001 | Monassevitch | |
| 6,174,280 B1 | 1/2001 | Oneda et al. | |
| 6,174,323 B1 | 1/2001 | Biggs et al. | |
| 6,179,195 B1 | 1/2001 | Adams et al. | |
| 6,179,776 B1 | 1/2001 | Adams et al. | |
| 6,183,411 B1 | 2/2001 | Mortier et al. | |
| RE37,117 E | 3/2001 | Palermo | |
| 6,197,017 B1 | 3/2001 | Brock et al. | |
| 6,197,022 B1 | 3/2001 | Baker | |
| 6,214,007 B1 | 4/2001 | Anderson | |
| 6,228,023 B1 | 5/2001 | Zaslavsky et al. | |
| 6,231,561 B1 | 5/2001 | Frazier et al. | |
| 6,234,958 B1 | 5/2001 | Snoke et al. | |
| 6,238,412 B1 | 5/2001 | Dubrul et al. | |
| 6,245,079 B1 | 6/2001 | Nobles et al. | |
| 6,260,552 B1 | 7/2001 | Mortier et al. | |
| 6,261,222 B1 | 7/2001 | Schweich, Jr. et al. | |
| 6,264,602 B1 | 7/2001 | Mortier et al. | |
| 6,270,453 B1 * | 8/2001 | Sakai | 600/141 |
| 6,270,515 B1 | 8/2001 | Linden et al. | |
| 6,277,064 B1 | 8/2001 | Yoon | |
| 6,283,973 B1 | 9/2001 | Hubbard et al. | |
| 6,290,674 B1 | 9/2001 | Roue et al. | |
| 6,293,956 B1 | 9/2001 | Crainich et al. | |
| 6,296,656 B1 | 10/2001 | Bolduc et al. | |
| 6,302,311 B1 * | 10/2001 | Adams et al. | 227/176.1 |
| 6,306,081 B1 | 10/2001 | Ishikawa et al. | |
| 6,306,159 B1 | 10/2001 | Schwartz et al. | |
| 6,306,163 B1 | 10/2001 | Fitz | |
| 6,312,437 B1 | 11/2001 | Kortenbach | |
| 6,315,714 B1 | 11/2001 | Akiba | |
| 6,315,715 B1 | 11/2001 | Taylor et al. | |
| 6,315,789 B1 | 11/2001 | Cragg | |
| 6,322,563 B1 | 11/2001 | Cummings et al. | |
| 6,322,580 B1 | 11/2001 | Kanner | |
| 6,331,165 B1 | 12/2001 | Turturro et al. | |
| 6,332,468 B1 | 12/2001 | Benetti | |
| 6,332,863 B1 | 12/2001 | Schweich, Jr. et al. | |
| 6,332,864 B1 | 12/2001 | Schweich, Jr. et al. | |
| 6,332,893 B1 | 12/2001 | Mortier et al. | |
| 6,336,940 B1 | 1/2002 | Graf et al. | |
| 6,346,074 B1 | 2/2002 | Roth | |
| 6,348,064 B1 | 2/2002 | Kanner | |
| 6,352,503 B1 * | 3/2002 | Matsui et al. | 600/104 |
| 6,355,052 B1 | 3/2002 | Neuss et al. | |
| 6,358,197 B1 | 3/2002 | Silverman et al. | |
| 6,363,938 B2 | 4/2002 | Saadat et al. | |
| 6,368,338 B1 | 4/2002 | Konya et al. | |
| 6,368,339 B1 | 4/2002 | Amplatz | |
| 6,387,104 B1 | 5/2002 | Pugsley, Jr. et al. | |
| 6,391,044 B1 | 5/2002 | Yadav et al. | |
| 6,402,679 B1 | 6/2002 | Mortier et al. | |
| 6,402,680 B2 | 6/2002 | Mortier et al. | |
| 6,406,420 B1 | 6/2002 | McCarthy et al. | |
| 6,408,889 B1 | 6/2002 | Komachi | |
| H2037 H | 7/2002 | Yates et al. | |
| 6,419,696 B1 | 7/2002 | Ortiz et al. | |
| 6,423,087 B1 | 7/2002 | Sawada | |
| 6,425,859 B1 | 7/2002 | Foley et al. | |
| 6,425,911 B1 | 7/2002 | Akerfeldt et al. | |
| 6,428,468 B1 | 8/2002 | Knighton et al. | |
| 6,428,550 B1 | 8/2002 | Vargas et al. | |
| 6,432,112 B2 | 8/2002 | Brock et al. | |
| 6,440,061 B1 | 8/2002 | Wenner et al. | |
| 6,443,944 B1 | 9/2002 | Doshi et al. | |
| 6,447,533 B1 * | 9/2002 | Adams | 606/213 |
| 6,458,074 B1 * | 10/2002 | Matsui et al. | 600/106 |
| 6,468,203 B2 | 10/2002 | Belson | |
| 6,478,791 B1 | 11/2002 | Carter et al. | |
| 6,485,411 B1 | 11/2002 | Konstorum et al. | |
| 6,494,888 B1 | 12/2002 | Laufer et al. | |
| 6,506,196 B1 | 1/2003 | Laufer | |
| 6,508,828 B1 | 1/2003 | Akerfeldt et al. | |
| 6,527,753 B2 | 3/2003 | Sekine et al. | |
| 6,533,796 B1 | 3/2003 | Sauer et al. | |
| 6,537,285 B1 | 3/2003 | Hatasaka, Jr. et al. | |
| 6,554,793 B1 | 4/2003 | Pauker et al. | |
| 6,554,845 B1 | 4/2003 | Fleenor et al. | |
| 6,558,400 B2 | 5/2003 | Deem et al. | |
| 6,569,085 B2 * | 5/2003 | Kortenbach et al. | 600/104 |
| 6,572,629 B2 * | 6/2003 | Kalloo et al. | 606/151 |
| 6,589,208 B2 | 7/2003 | Ewers et al. | |
| 6,592,596 B1 | 7/2003 | Geitz | |
| 6,641,592 B1 | 11/2003 | Sauer et al. | |
| 6,656,194 B1 | 12/2003 | Gannoe et al. | |
| 6,663,639 B1 | 12/2003 | Laufer et al. | |
| 6,695,764 B2 | 2/2004 | Silverman et al. | |
| 6,702,826 B2 | 3/2004 | Liddicoat et al. | |
| 6,716,232 B1 | 4/2004 | Vidal et al. | |
| 6,719,763 B2 | 4/2004 | Chung et al. | |
| 6,719,764 B1 | 4/2004 | Gellman et al. | |
| 6,736,828 B1 * | 5/2004 | Adams et al. | 606/213 |
| 6,743,239 B1 | 6/2004 | Kuehn et al. | |
| 6,743,240 B2 | 6/2004 | Smith et al. | |
| 6,746,460 B2 | 6/2004 | Gannoe et al. | |
| 6,755,843 B2 | 6/2004 | Chung et al. | |
| 6,761,685 B2 | 7/2004 | Adams et al. | |
| 6,773,440 B2 | 8/2004 | Gannoe et al. | |

| Patent/Publication | Date | Inventor |
|---|---|---|
| 6,773,441 B1 | 8/2004 | Laufer et al. |
| 6,800,056 B2 | 10/2004 | Tartaglia et al. |
| 6,808,491 B2 * | 10/2004 | Kortenbach et al. ......... 600/104 |
| 6,811,532 B2 * | 11/2004 | Ogura et al. ................. 600/146 |
| 6,817,974 B2 | 11/2004 | Cooper et al. |
| 6,821,285 B2 | 11/2004 | Laufer et al. |
| 6,835,199 B2 | 12/2004 | McGuckin, Jr. et al. |
| 6,837,846 B2 * | 1/2005 | Jaffe et al. ................... 600/114 |
| 6,837,849 B2 | 1/2005 | Ogura et al. |
| 6,899,673 B2 * | 5/2005 | Ogura et al. ................. 600/146 |
| 6,921,361 B2 | 7/2005 | Suzuki et al. |
| 6,921,378 B2 | 7/2005 | O'Keefe et al. |
| 6,932,834 B2 | 8/2005 | Lizardi et al. |
| 6,974,411 B2 * | 12/2005 | Belson ........................ 600/114 |
| 6,986,737 B2 * | 1/2006 | Suzuki et al. ................ 600/106 |
| 6,986,781 B2 | 1/2006 | Smith |
| 6,997,931 B2 * | 2/2006 | Sauer et al. .................. 606/139 |
| 7,063,630 B2 | 6/2006 | Cavallaro |
| 7,083,630 B2 | 8/2006 | DeVries et al. |
| 7,156,857 B2 * | 1/2007 | Pasricha et al. .............. 606/148 |
| 7,160,312 B2 | 1/2007 | Saadat |
| 7,232,445 B2 * | 6/2007 | Kortenbach et al. ......... 606/142 |
| 7,727,246 B2 * | 6/2010 | Sixto et al. ................... 606/151 |
| 2001/0000040 A1 | 3/2001 | Adams et al. |
| 2001/0016675 A1 | 8/2001 | Mortier et al. |
| 2001/0025171 A1 | 9/2001 | Mortier et al. |
| 2001/0049509 A1 | 12/2001 | Sekine et al. |
| 2001/0051815 A1 | 12/2001 | Esplin |
| 2001/0056282 A1 * | 12/2001 | Sonnenschein et al. ...... 606/139 |
| 2002/0010490 A1 | 1/2002 | Schaller et al. |
| 2002/0013608 A1 | 1/2002 | ElAttrache et al. |
| 2002/0019649 A1 | 2/2002 | Sikora et al. |
| 2002/0022765 A1 | 2/2002 | Belson |
| 2002/0022851 A1 * | 2/2002 | Kalloo et al. ................. 606/151 |
| 2002/0022861 A1 | 2/2002 | Jacobs et al. |
| 2002/0029080 A1 | 3/2002 | Mortier et al. |
| 2002/0040226 A1 * | 4/2002 | Laufer et al. ................. 606/153 |
| 2002/0049458 A1 | 4/2002 | Singhatat |
| 2002/0055757 A1 | 5/2002 | Torre et al. |
| 2002/0058855 A1 | 5/2002 | Schweich, Jr. et al. |
| 2002/0062062 A1 | 5/2002 | Belson et al. |
| 2002/0065534 A1 | 5/2002 | Hermann et al. |
| 2002/0068849 A1 | 6/2002 | Schweich, Jr. et al. |
| 2002/0068945 A1 | 6/2002 | Sixto, Jr. et al. |
| 2002/0068946 A1 * | 6/2002 | Kortenbach et al. ......... 606/142 |
| 2002/0072761 A1 | 6/2002 | Abrams et al. |
| 2002/0077524 A1 | 6/2002 | Schweich, Jr. et al. |
| 2002/0078967 A1 | 6/2002 | Sixto, Jr. et al. |
| 2002/0082621 A1 | 6/2002 | Schurr et al. |
| 2002/0082622 A1 | 6/2002 | Kane |
| 2002/0087048 A1 | 7/2002 | Brock et al. |
| 2002/0107530 A1 | 8/2002 | Sauer et al. |
| 2002/0111534 A1 * | 8/2002 | Suzuki et al. ................. 600/102 |
| 2002/0116012 A1 | 8/2002 | May et al. |
| 2002/0120178 A1 | 8/2002 | Tartaglia et al. |
| 2002/0120253 A1 | 8/2002 | Ouchi |
| 2002/0147385 A1 | 10/2002 | Butler et al. |
| 2002/0161281 A1 | 10/2002 | Jaffe et al. |
| 2002/0177750 A1 * | 11/2002 | Pilvisto ........................ 600/146 |
| 2002/0183768 A1 | 12/2002 | Deem et al. |
| 2002/0193661 A1 | 12/2002 | Belson |
| 2002/0193662 A1 | 12/2002 | Belson |
| 2002/0193816 A1 | 12/2002 | Laufer et al. |
| 2003/0004544 A1 * | 1/2003 | Kawashima et al. ......... 606/222 |
| 2003/0009085 A1 | 1/2003 | Arai et al. |
| 2003/0036748 A1 * | 2/2003 | Cooper et al. ................ 606/1 |
| 2003/0045778 A1 | 3/2003 | Ohline et al. |
| 2003/0055442 A1 * | 3/2003 | Laufer et al. ................. 606/153 |
| 2003/0065359 A1 | 4/2003 | Weller et al. |
| 2003/0109892 A1 | 6/2003 | Deem et al. |
| 2003/0109900 A1 | 6/2003 | Martinek |
| 2003/0120289 A1 * | 6/2003 | McGuckin et al. ........... 606/151 |
| 2003/0139752 A1 | 7/2003 | Pasricha et al. |
| 2003/0158582 A1 | 8/2003 | Bonutti et al. |
| 2003/0165887 A1 * | 9/2003 | Reed ............................ 435/6 |
| 2003/0167062 A1 | 9/2003 | Gambale et al. |
| 2003/0167071 A1 | 9/2003 | Martin et al. |
| 2003/0171651 A1 | 9/2003 | Page et al. |
| 2003/0171760 A1 | 9/2003 | Gambale |
| 2003/0176890 A1 | 9/2003 | Buckman et al. |
| 2003/0181924 A1 | 9/2003 | Yamamoto et al. |
| 2003/0204205 A1 | 10/2003 | Sauer et al. |
| 2003/0208209 A1 | 11/2003 | Gambale et al. |
| 2003/0216613 A1 | 11/2003 | Suzuki et al. |
| 2003/0225312 A1 | 12/2003 | Suzuki et al. |
| 2003/0229296 A1 | 12/2003 | Ishikawa et al. |
| 2003/0236505 A1 | 12/2003 | Bonadio et al. |
| 2003/0236535 A1 * | 12/2003 | Onuki et al. .................. 606/144 |
| 2003/0236536 A1 | 12/2003 | Grigoryants et al. |
| 2003/0236549 A1 | 12/2003 | Bonadio et al. |
| 2004/0010271 A1 | 1/2004 | Kortenbach |
| 2004/0024386 A1 | 2/2004 | Deem et al. |
| 2004/0030347 A1 | 2/2004 | Gannoe et al. |
| 2004/0049095 A1 | 3/2004 | Goto et al. |
| 2004/0059346 A1 | 3/2004 | Adams et al. |
| 2004/0059350 A1 | 3/2004 | Gordon et al. |
| 2004/0082963 A1 | 4/2004 | Gannoe et al. |
| 2004/0088008 A1 | 5/2004 | Gannoe et al. |
| 2004/0092974 A1 | 5/2004 | Gannoe et al. |
| 2004/0093091 A1 | 5/2004 | Gannoe et al. |
| 2004/0097986 A1 | 5/2004 | Adams |
| 2004/0116949 A1 | 6/2004 | Ewers et al. |
| 2004/0122452 A1 | 6/2004 | Deem et al. |
| 2004/0122453 A1 | 6/2004 | Deem et al. |
| 2004/0122456 A1 | 6/2004 | Saadat et al. |
| 2004/0122473 A1 | 6/2004 | Ewers et al. |
| 2004/0122474 A1 | 6/2004 | Gellman et al. |
| 2004/0133238 A1 | 7/2004 | Cerier |
| 2004/0138682 A1 * | 7/2004 | Onuki et al. .................. 606/144 |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0167546 A1 | 8/2004 | Saadat et al. |
| 2004/0176784 A1 | 9/2004 | Okada |
| 2004/0193008 A1 | 9/2004 | Jaffe et al. |
| 2004/0193009 A1 | 9/2004 | Jaffe et al. |
| 2004/0193117 A1 | 9/2004 | Laufer et al. |
| 2004/0193184 A1 | 9/2004 | Laufer et al. |
| 2004/0193193 A1 | 9/2004 | Laufer et al. |
| 2004/0193194 A1 | 9/2004 | Laufer et al. |
| 2004/0194790 A1 | 10/2004 | Laufer et al. |
| 2004/0199052 A1 | 10/2004 | Banik et al. |
| 2004/0210243 A1 | 10/2004 | Gannoe et al. |
| 2004/0215216 A1 | 10/2004 | Gannoe et al. |
| 2004/0225183 A1 | 11/2004 | Michlitsch et al. |
| 2004/0225305 A1 | 11/2004 | Ewers et al. |
| 2004/0243152 A1 | 12/2004 | Taylor et al. |
| 2004/0249362 A1 | 12/2004 | Levine et al. |
| 2004/0249367 A1 | 12/2004 | Saadat et al. |
| 2004/0249392 A1 | 12/2004 | Mikkaichi et al. |
| 2004/0249395 A1 | 12/2004 | Mikkaichi et al. |
| 2005/0004576 A1 | 1/2005 | Benderev |
| 2005/0020901 A1 | 1/2005 | Belson et al. |
| 2005/0033320 A1 | 2/2005 | McGuckin, Jr. et al. |
| 2005/0033328 A1 | 2/2005 | Laufer et al. |
| 2005/0043758 A1 | 2/2005 | Golden et al. |
| 2005/0049617 A1 | 3/2005 | Chatlynne et al. |
| 2005/0065397 A1 | 3/2005 | Saadat et al. |
| 2005/0065401 A1 | 3/2005 | Saadat et al. |
| 2005/0065536 A1 | 3/2005 | Ewers et al. |
| 2005/0075653 A1 | 4/2005 | Saadat et al. |
| 2005/0113640 A1 | 5/2005 | Saadat et al. |
| 2005/0113862 A1 | 5/2005 | Besselink et al. |
| 2005/0119524 A1 | 6/2005 | Sekine et al. |
| 2005/0119671 A1 | 6/2005 | Reydel et al. |
| 2005/0149115 A1 | 7/2005 | Roue et al. |
| 2005/0192629 A1 | 9/2005 | Saadat et al. |
| 2005/0203488 A1 | 9/2005 | Michlitsch et al. |
| 2005/0203489 A1 | 9/2005 | Saadat et al. |
| 2005/0203500 A1 | 9/2005 | Saadat et al. |
| 2005/0234294 A1 | 10/2005 | Saadat et al. |
| 2005/0234296 A1 | 10/2005 | Saadat et al. |
| 2005/0245945 A1 | 11/2005 | Ewers et al. |
| 2005/0250980 A1 | 11/2005 | Swanstrom et al. |
| 2005/0250984 A1 | 11/2005 | Lam et al. |
| 2005/0250985 A1 | 11/2005 | Saadat et al. |
| 2005/0250986 A1 | 11/2005 | Rothe et al. |
| 2005/0250987 A1 | 11/2005 | Ewers et al. |

| | | | |
|---|---|---|---|
| 2005/0250988 A1 | 11/2005 | Ewers et al. | |
| 2005/0251091 A1 | 11/2005 | Saadat et al. | |
| 2005/0251157 A1 | 11/2005 | Saadat et al. | |
| 2005/0251158 A1 | 11/2005 | Saadat et al. | |
| 2005/0251159 A1 | 11/2005 | Ewers et al. | |
| 2005/0251160 A1 | 11/2005 | Saadat et al. | |
| 2005/0251161 A1 | 11/2005 | Saadat et al. | |
| 2005/0251162 A1 | 11/2005 | Rothe et al. | |
| 2005/0251165 A1 | 11/2005 | Vaughan et al. | |
| 2005/0251166 A1 | 11/2005 | Vaughan et al. | |
| 2005/0251176 A1 | 11/2005 | Swanstrom et al. | |
| 2005/0251177 A1 | 11/2005 | Saadat et al. | |
| 2005/0251189 A1 | 11/2005 | Saadat et al. | |
| 2005/0251202 A1 | 11/2005 | Ewers et al. | |
| 2005/0251205 A1 | 11/2005 | Ewers et al. | |
| 2005/0251206 A1 | 11/2005 | Maahs et al. | |
| 2005/0251207 A1 | 11/2005 | Flores et al. | |
| 2005/0251209 A1 | 11/2005 | Saadat et al. | |
| 2005/0251210 A1 | 11/2005 | Westra et al. | |
| 2005/0267335 A1 | 12/2005 | Okada et al. | |
| 2005/0267523 A1 | 12/2005 | Devellian et al. | |
| 2005/0272977 A1 | 12/2005 | Saadat et al. | |
| 2005/0273135 A1 | 12/2005 | Chanduszko et al. | |
| 2005/0277945 A1 | 12/2005 | Saadat et al. | |
| 2005/0277966 A1 | 12/2005 | Ewers et al. | |
| 2005/0277975 A1 | 12/2005 | Saadat et al. | |
| 2005/0277981 A1 | 12/2005 | Maahs et al. | |
| 2005/0277983 A1 | 12/2005 | Saadat et al. | |
| 2006/0009789 A1 | 1/2006 | Gambale et al. | |
| 2006/0020274 A1 | 1/2006 | Ewers et al. | |
| 2006/0020276 A1 | 1/2006 | Saadat et al. | |
| 2006/0100579 A1 | 5/2006 | Maahs et al. | |
| 2006/0135971 A1 | 6/2006 | Swanstrom et al. | |
| 2006/0157067 A1 | 7/2006 | Saadat et al. | |
| 2006/0161185 A1 | 7/2006 | Saadat et al. | |
| 2006/0178560 A1 | 8/2006 | Saadat et al. | |
| 2006/0178562 A1 | 8/2006 | Saadat et al. | |
| 2006/0183975 A1 | 8/2006 | Saadat et al. | |
| 2006/0184161 A1 | 8/2006 | Maahs et al. | |
| 2006/0189845 A1 | 8/2006 | Maahs et al. | |
| 2006/0217762 A1 | 9/2006 | Maahs et al. | |
| 2006/0237022 A1 | 10/2006 | Chen et al. | |
| 2006/0237023 A1 | 10/2006 | Cox et al. | |
| 2006/0258909 A1 | 11/2006 | Saadat et al. | |
| 2006/0271073 A1 | 11/2006 | Lam et al. | |
| 2006/0271074 A1 | 11/2006 | Ewers et al. | |
| 2006/0271101 A1 | 11/2006 | Saadat et al. | |
| 2007/0123840 A1 | 5/2007 | Cox | |
| 2007/0142849 A1 | 6/2007 | Ewers et al. | |

FOREIGN PATENT DOCUMENTS

| | | |
|---|---|---|
| DE | 3504824 A1 | 8/1986 |
| EP | 0 480 428 A2 | 4/1992 |
| EP | 0 497 781 B1 | 8/1992 |
| EP | 0 646 356 A2 | 4/1995 |
| EP | 0 847 727 A1 | 6/1998 |
| EP | 1 031 321 A1 | 8/2000 |
| FR | 2 768 324 A1 | 3/1999 |
| GB | 2 165 559 A | 4/1986 |
| WO | WO 92/04870 A1 | 4/1992 |
| WO | WO 95/19140 A1 | 7/1995 |
| WO | WO 95/25468 A1 | 9/1995 |
| WO | WO 99/22649 A2 | 5/1999 |
| WO | WO 99/51283 A2 | 10/1999 |
| WO | WO 99/59664 A1 | 11/1999 |
| WO | WO 00/40159 A1 | 7/2000 |
| WO | WO 00/54653 A1 | 9/2000 |
| WO | WO 00/57796 A1 | 10/2000 |
| WO | WO 00/78227 A1 | 12/2000 |
| WO | WO 00/78229 A1 | 12/2000 |
| WO | WO 01/21246 A1 | 3/2001 |
| WO | WO 01/66001 A2 | 9/2001 |
| WO | WO 01/66018 A1 | 9/2001 |
| WO | WO 01/67964 A3 | 9/2001 |
| WO | WO 01/70096 A1 | 9/2001 |
| WO | WO 01/70097 A1 | 9/2001 |
| WO | WO 01/85034 A1 | 11/2001 |
| WO | WO 01/87144 A1 | 11/2001 |
| WO | WO 01/89370 A2 | 11/2001 |
| WO | WO 01/89392 A2 | 11/2001 |
| WO | WO 01/89393 A1 | 11/2001 |
| WO | WO 02/00119 A2 | 1/2002 |
| WO | WO 02/24058 A2 | 3/2002 |
| WO | WO 02/24058 A3 | 3/2002 |
| WO | WO 02/24080 A2 | 3/2002 |
| WO | WO 02/39880 A2 | 5/2002 |
| WO | WO 02/39909 A1 | 5/2002 |
| WO | WO 02/060328 A1 | 8/2002 |
| WO | WO 02/064012 A2 | 8/2002 |
| WO | WO 02/068988 A1 | 9/2002 |
| WO | WO 02/069841 A2 | 9/2002 |
| WO | WO 02/085252 A1 | 10/2002 |
| WO | WO 02/094105 A2 | 11/2002 |
| WO | WO 03/007796 A2 | 1/2003 |
| WO | WO 03/007799 A2 | 1/2003 |
| WO | WO 03/090633 A2 | 11/2003 |
| WO | WO 03/092509 A1 | 11/2003 |
| WO | WO 03/094785 A1 | 11/2003 |
| WO | WO 03/096909 A1 | 11/2003 |
| WO | WO 03/099137 A2 | 12/2003 |
| WO | WO 03/105732 A1 | 12/2003 |
| WO | WO 2004/004542 A2 | 1/2004 |
| WO | WO 2004/004544 A2 | 1/2004 |
| WO | WO 2004/019787 A2 | 3/2004 |
| WO | WO 2004/019788 A2 | 3/2004 |
| WO | WO 2004/021865 A2 | 3/2004 |
| WO | WO 2004/021867 A2 | 3/2004 |
| WO | WO 2004/021868 A2 | 3/2004 |
| WO | WO 2004/021873 A2 | 3/2004 |
| WO | WO 2004/021894 A1 | 3/2004 |
| WO | WO 2004/049905 A2 | 6/2004 |
| WO | WO 2004/056273 A1 | 7/2004 |
| WO | WO 2004/071284 A1 | 8/2004 |
| WO | WO 2004/075787 A1 | 9/2004 |
| WO | WO 2004/080313 A1 | 9/2004 |
| WO | WO 2004/084702 A2 | 10/2004 |
| WO | WO 2004/084808 A2 | 10/2004 |
| WO | WO 2004/103189 A1 | 12/2004 |
| WO | WO 2005/004727 A1 | 1/2005 |
| WO | WO 2005/037152 A1 | 4/2005 |

OTHER PUBLICATIONS

Chuttani et al., "A Novel Endoscopic Full-thickness Plicator for Treatment of GERD: An Animal Model Study," *Gastrointestinal Endoscopy*, vol. 26, No. 1,( 2002), pp. 116-122.

Mason, "Development of Future of Gastroplasties for Morbid Obesity," *Arch Surg*, vol. 138 (Apr. 2003), pp. 362-366.

Angiolink, The Expanding Vascular Staple [brochure], 1 page total.

Bluett et al., "Experimental Evaluation of Staple Lines in Gastric Surgery," *Arch. Surg.*, vol. 122, Jul. 1987, pp. 772-776.

Brolin et al., "Experimental Evaluation of Techniques of Gastric Paritioning for Morbid Obesity", *Surgery, Gynecology & Obstetrics*, vol. 153, Dec. 1981, pp. 878-882.

Johnston et al. "The Magenstrasse and Mill Operation of Morbid Obesity", *Obesity Surgery* 13, 2003, pp. 10-16.

Okudaira et al., "The Healing and Tensile Strength of the Gastroplasty Staple Line," *The American Surgeon*, Oct. 1984, pp. 564-568.

Surgical Dynamics Inc., The S D sorb Meniscal Stapler [brochure] (1997), 3 pages total.

Sutura, The Next Generation in Vascular Suturing Devices: SuperStitch [brochure], 2 pages total.

File History for U.S. Appl. No. 10/173,203, filed Jun. 13, 2002.
File History for U.S. Appl. No. 10/173,220, filed Jun. 13, 2002.
File History for U.S. Appl. No. 10/173,227, filed Jun. 13, 2002.
File History for U.S. Appl. No. 10/173,238, filed Jun. 13, 2002.
File History for U.S. Appl. No. 10/228,619, filed Nov. 4, 2002.
File History for U.S. Appl. No. 10/346,709, filed Jan. 15, 2003.
File History for U.S. Appl. No. 10/458,060, filed Jun. 9, 2003.
File History for U.S. Appl. No. 10/734,547, filed Dec. 12, 2003.
File History for U.S. Appl. No. 10/735,030, filed Dec. 12, 2003.
File History for U.S. Appl. No. 10/797,485, filed Mar. 9, 2004.
File History for U.S. Appl. No. 10/990,406, filed Nov. 16, 2004.
File History for U.S. Appl. No. 10/990,453, filed Nov. 16, 2004.

File History for U.S. Appl. No. 10/990,559, filed Nov. 16, 2004.
File History for U.S. Appl. No. 10/991,118, filed Nov. 16, 2004.
File History for U.S. Appl. No. 10/992,306, filed Nov. 17, 2004.
File History for U.S. Appl. No. 10/994,101, filed Nov. 18, 2004.
File History for U.S. Appl. No. 11/400,120, filed Apr. 7, 2006.
European Patent Application No. 3817830.7 filed Dec. 22, 2003, Supplemental European Search Report mailed Oct. 7, 2009.
European Patent Application No. 4702577 filed Jan. 15, 2004, International Preliminary Report on Patentability mailed Jul. 15, 2005.
European Patent Application No. 4752537.3 filed May 17, 2004, Supplemental European Search Report mailed Apr. 7, 2008.
European Patent Application No. 4813830.9 filed Dec. 10, 2004, International Preliminary Report on Patentability mailed Jun. 12, 2006.
PCT International Patent Application No. PCT/US2003/034726 filed Oct. 31, 2003, International Search Report mailed Jan. 21, 2005.
PCT International Patent Application No. PCT/US2003/040859 filed Dec. 22, 2003, International Search Report mailed Jun. 22, 2005.
PCT International Patent Application No. PCT/US2004/015539 filed May 17, 2004, Supplemental European Search Report mailed Apr. 7, 2008.
PCT International Patent Application No. PCT/US2004/041570 filed Dec. 10, 2004, International Search Report mailed Oct. 4, 2005.
PCT International Patent Application No. PCT/US2004/041570 filed Dec. 10, 2004, International Preliminary Report on Patentability mailed Jun. 12, 2006.
US 6,447,535, 09/2002, Jacobs et al. (withdrawn)

\* cited by examiner

*Primary Examiner* — Darwin P Erezo
*Assistant Examiner* — Dianne Dornbusch
(74) *Attorney, Agent, or Firm* — Charles C. Fowler; USGI Medical, Inc.

(57) ABSTRACT

Apparatus and methods are provided for forming a gastrointestinal tissue fold by engaging tissue at a first tissue contact point and moving the first tissue contact point from a position initially distal to, or in line with, a second tissue contact point to a position proximal of the second contact point, thereby forming the tissue fold, and extending an anchor assembly through the tissue fold from a vicinity of the second tissue contact point. Adjustable anchor assemblies; as well as anchor delivery systems, shape-lockable guides and methods for endoluminally performing medical procedures, such as gastric reduction, treatment of gastroesophageal reflux disease, resection of lesions, and treatment of bleeding sites; are also provided.

22 Claims, 42 Drawing Sheets

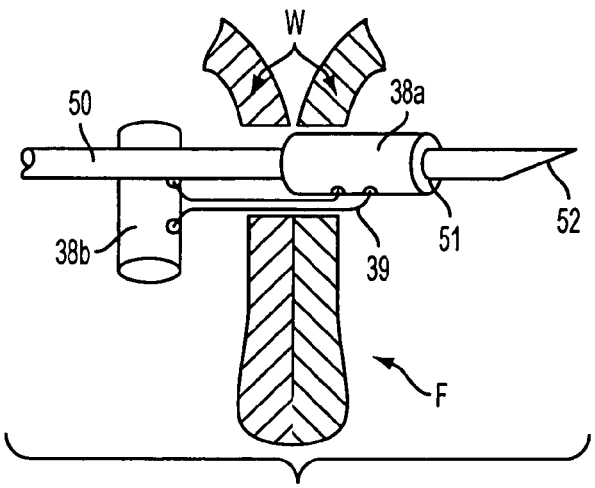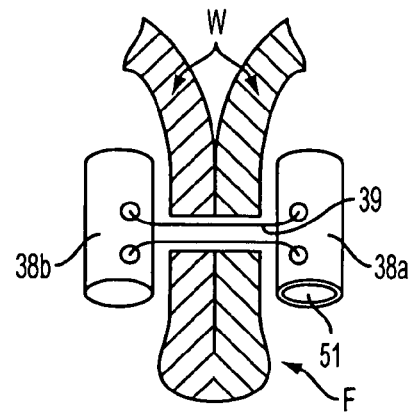
FIG. 5A  FIG. 5B
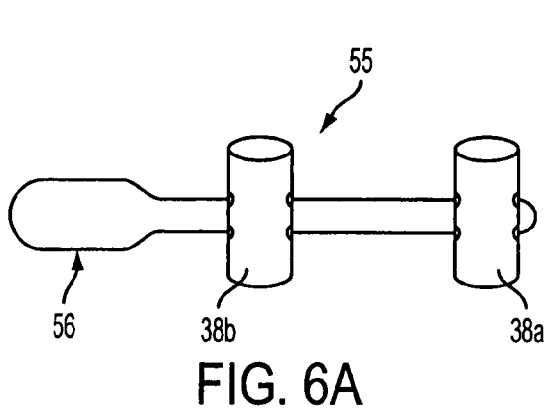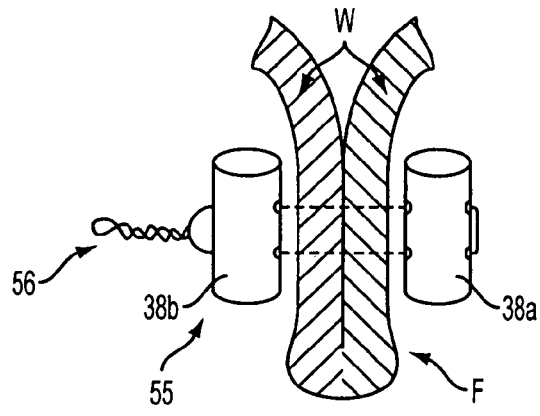
FIG. 6A  FIG. 6B
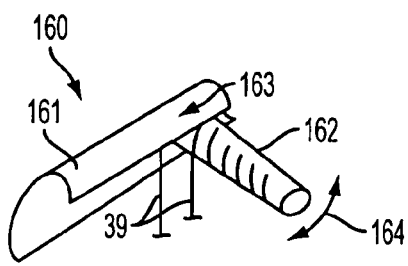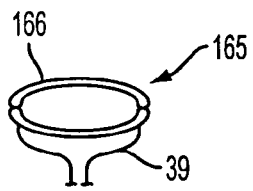
FIG. 17A  FIG. 17B
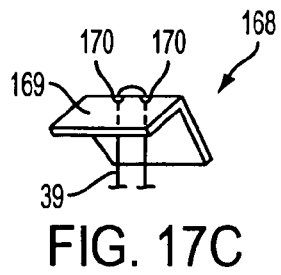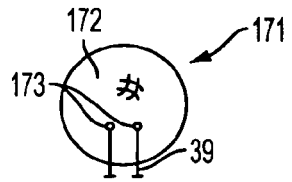
FIG. 17C  FIG. 17D

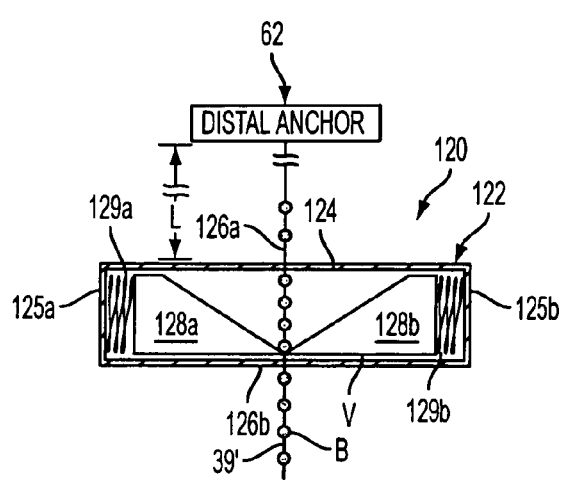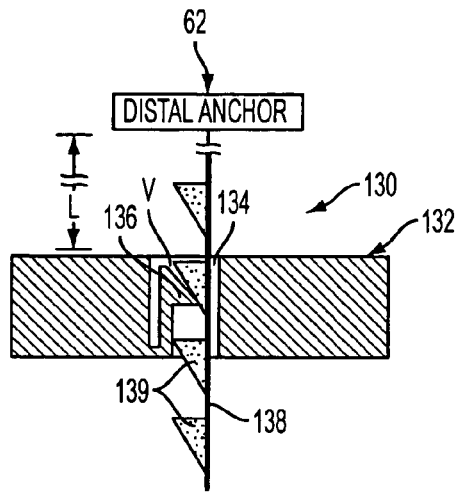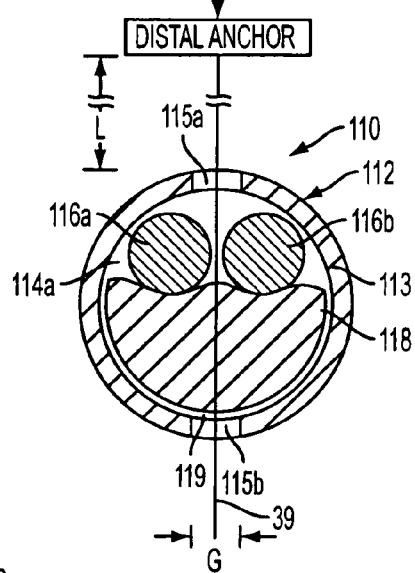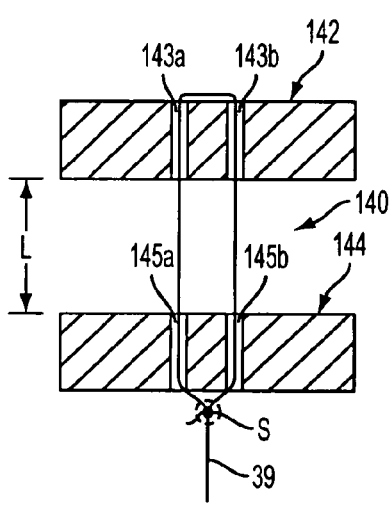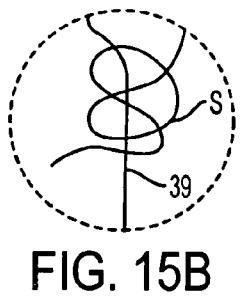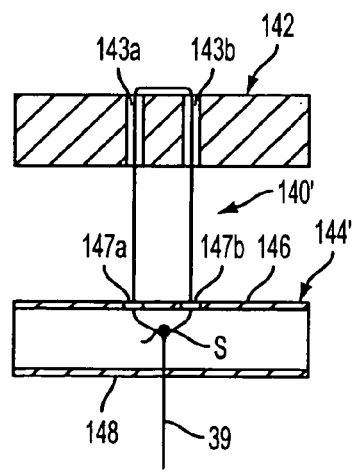
FIG. 14A
FIG. 14B
FIG. 13
FIG. 15A
FIG. 15B
FIG. 15C

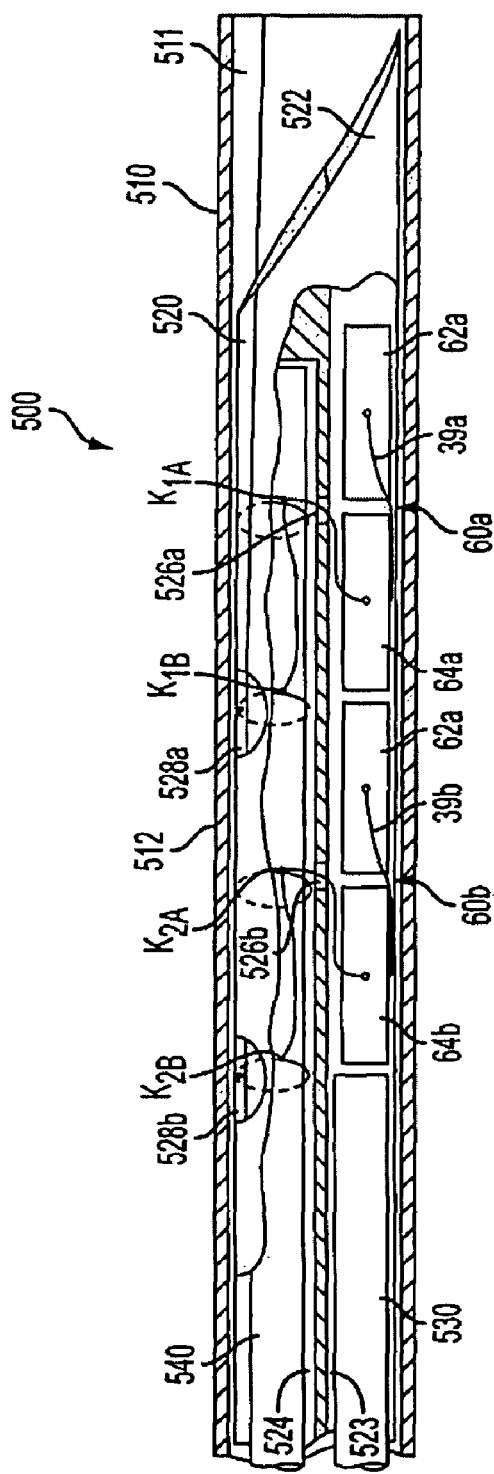
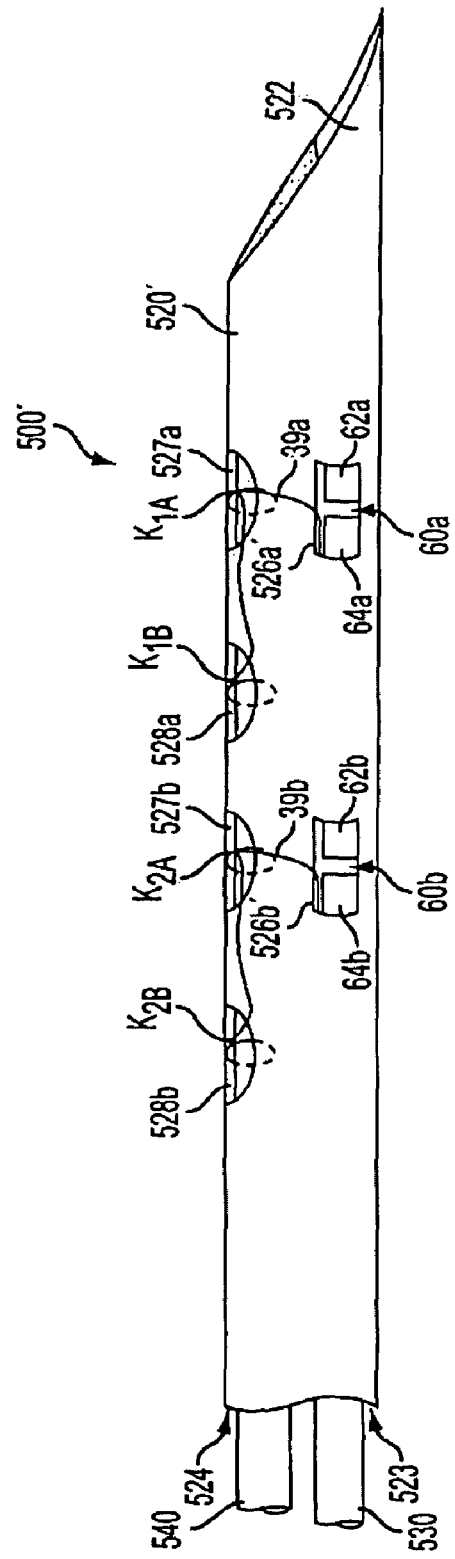
FIG. 25
FIG. 26

APPARATUS AND METHODS FOR FORMING AND SECURING GASTROINTESTINAL TISSUE FOLDS

REFERENCE TO RELATED APPLICATIONS

This application is a Continuation-In-Part of U.S. patent application Ser. No. 10/672,375, filed Sep. 25, 2003, now U.S. Pat. No. 7,416,554, which claims the benefit of the filing date of U.S. provisional patent application Ser. No. 60/500,627, filed Sep. 5, 2003; and is a Continuation-In-Part of U.S. patent applications Ser. No. 10/612,170, filed Jul. 1, 2003, and Ser. No. 10/639,162, filed Aug. 11, 2003, now U.S. Pat. No. 7,618,426; both of which claim the benefit of the filing date of U.S. provisional patent application Ser. No. 60/433,065, filed Dec. 11, 2002. Furthermore, this application is a Continuation-In-Part of U.S. patent application Ser. No. 10/173,203, filed Jun. 13, 2002, now U.S. Pat. No. 7,128,708; as well U.S. patent application Ser. No. 10/458,060, filed Jun. 9, 2003, which is a Continuation-In-Part of U.S. patent application Ser. No. 10/346,709, filed Jan. 15, 2003, now U.S. Pat. No. 7,637,905, and which claims the benefit of the filing date of U.S. provisional patent application Ser. No. 60/471,893, filed May 19, 2003. Furtherstill, this application is a Continuation-In-Part of U.S. patent application Ser. No. 10/288,619, filed Nov. 4, 2002, now U.S. Pat. No. 7,160,312; which is a Continuation-In-Part of U.S. patent application Ser. No. 09/746,579, filed Dec. 20, 2000, now U.S. Pat. No. 6,991,643, and a Continuation-In-Part of, commonly assigned U.S. patent application Ser. No. 10/188,509, filed Jul. 3, 2002, now U.S. Pat. No. 7,186,262; which is a Continuation-In-Part of U.S. patent application Ser. No. 09/898,726, filed Jul. 3, 2001, now U.S. Pat. No. 6,626,899; which is a Continuation-In-Part of U.S. patent application Ser. No. 09/602,436, filed Jun. 23, 2000, now U.S. Pat. No. 6,669,687, which claims the benefit of the filing date of U.S. provisional patent application Ser. No. 60/141,077, filed Jun. 25, 1999. All of these applications are incorporated herein by reference in their entireties.

FIELD OF THE INVENTION

The present invention relates to methods and apparatus for intraluminally forming and securing gastrointestinal ("GI") tissue folds. More particularly, the present invention relates to methods and apparatus for reducing the effective cross-sectional area of a gastrointestinal lumen.

BACKGROUND OF THE INVENTION

Morbid obesity is a serious medical condition pervasive in the United States and other countries. Its complications include hypertension, diabetes, coronary artery disease, stroke, congestive heart failure, multiple orthopedic problems and pulmonary insufficiency with markedly decreased life expectancy.

Several surgical techniques have been developed to treat morbid obesity, e.g., bypassing an absorptive surface of the small intestine, or reducing the stomach size. These procedures are difficult to perform in morbidly obese patients because it is often difficult to gain access to the digestive organs. In particular, the layers of fat encountered in morbidly obese patients make difficult direct exposure of the digestive organs with a wound retractor, and standard laparoscopic trocars may be of inadequate length.

In addition, previously known open surgical procedures may present numerous life-threatening post-operative complications, and may cause atypical diarrhea, electrolytic imbalance, unpredictable weight loss and reflux of nutritious chyme proximal to the site of the anastamosis. Further, the sutures or staples that are often used in these surgical procedures may require extensive training by the clinician to achieve competent use, and may concentrate significant force over a small surface area of the tissue, thereby potentially causing the suture or staple to tear through the tissue.

The gastrointestinal lumen includes four tissue layers, wherein the mucosa layer is the top tissue layer followed by connective tissue, the muscularis layer and the serosa layer. One problem with conventional gastrointestinal reduction systems is that the anchors (or staples) must engage at least the muscularis tissue layer in order to provide a proper foundation. In other words, the mucosa and connective tissue layers typically are not strong enough to sustain the tensile loads imposed by normal movement of the stomach wall during ingestion and processing of food. In particular, these layers tend to stretch elastically rather than firmly hold the anchors (or staples) in position, and accordingly, the more rigid muscularis and/or serosa layer must be engaged. This problem of capturing the muscularis or serosa layers becomes particularly acute where it is desired to place an anchor or other apparatus transesophageally rather than intraoperatively, since care must be taken in piercing the tough stomach wall not to inadvertently puncture adjacent tissue or organs.

In view of the aforementioned limitations, it would be desirable to provide methods and apparatus for forming gastrointestinal tissue folds that achieve gastric reduction by reconfiguring the GI lumen of a patient.

It would be desirable to provide methods and apparatus for forming gastrointestinal tissue folds using anchors that can be reconfigured from a reduced delivery profile to an expanded deployed profile.

It also would be desirable to provide methods and apparatus for forming gastrointestinal tissue folds, wherein an anchor assembly is extended across stomach folds that include the muscularis and serosa tissue layers.

It further would be desirable to provide methods and apparatus for forming gastrointestinal tissue folds, wherein the anchor assembly is deployed in a manner that reduces a possibility of injuring neighboring organs.

It still further would be desirable to provide methods and apparatus for forming gastrointestinal tissue folds, wherein reduced training of a clinician is required to achieve competent use of the anchor assembly.

It would be desirable to provide methods and apparatus for forming gastrointestinal tissue folds that facilitate approximation of a plurality of tissue folds.

SUMMARY OF THE INVENTION

In view of the foregoing, it is an object of the present invention to provide methods and apparatus for forming gastrointestinal tissue folds that achieve gastric reduction by reconfiguring the GI lumen of a patient.

It is another object of the present invention to provide methods and apparatus for forming gastrointestinal tissue folds using anchors that can be reconfigured from a reduced delivery profile to an expanded deployed profile.

It is an additional object of this invention to provide methods and apparatus for forming gastrointestinal tissue folds in which an anchor assembly is extended across stomach folds that include the muscularis and serosa tissue layers.

It is a further object of the present invention to provide methods and apparatus for forming gastrointestinal tissue folds, wherein the anchor assembly is deployed in a manner that reduces a possibility of injuring neighboring organs.

It is yet another object to provide methods and apparatus for forming gastrointestinal tissue folds, wherein reduced training of a clinician is required to achieve competent use of the anchor assembly.

It is an object to provide methods and apparatus for forming gastrointestinal tissue folds that facilitate approximation of a plurality of tissue folds.

These and other objects of the present invention are accomplished by providing a catheter configured for advancement into a patient's gastrointestinal lumen to form a gastrointestinal tissue fold. In one preferred embodiment, the catheter has a distal region including a tissue grabbing assembly adapted to engage and/or stretch a portion of the tissue wall of the GI lumen at a first tissue contact point. A second tissue contact point is then established with the tissue wall at a location initially proximal of, or in line with, the first tissue contact point. The tissue engaged by the tissue grabbing assembly then is moved to a position proximal of the second tissue contact point to form a tissue fold, and one or more anchor assemblies may be delivered across the tissue fold. Preferably, delivery of the anchor assembly across the tissue fold includes delivering the anchor assembly across the muscularis and serosa layers of the tissue wall.

Optionally, a third tissue contact point may be established at another location initially proximal of, or in line with, the first tissue contact point. Upon movement of the tissue engaged by the tissue grabbing assembly to a position proximal of both the second and third tissue contact points, a tissue fold is formed with the second and third contact points on opposing sides of the fold. The third contact point may provide backside stabilization upon delivery of the anchor assembly across the tissue fold from a vicinity of the second tissue contact point.

In a preferred embodiment, the tissue grabbing assembly is carried on a first flexible tube associated with the distal region of the catheter, and the one or more anchor assemblies are delivered by an anchor delivery system disposed within a second flexible tube associated with the distal region of the catheter. The tissue grabbing assembly may comprise any of a number of mechanisms configured to engage the tissue wall, including a pair of jaws configured to move between open and closed positions, a plurality of linearly translating barbs, a coil screw, or one or more needles or hooks. The first tissue contact point may be moved from a tissue engagement position distal to, or in line with, the second tissue contact point, to the tissue folding position by any of a number of mechanisms, including a hinge assembly, a treadmill assembly, or a linear pull assembly.

More preferably, the distal region of the catheter includes a bendable section that permits the first tissue contact point to be positioned relative to the second tissue contact point so that the tissue fold is oriented substantially perpendicular to the anchor delivery system. In this manner, the anchor delivery system, when deployed, pierces the tissue fold and exits into the interior of the GI lumen, rather than the exterior of the tissue wall, thereby reducing a risk of injury to adjacent organs.

The anchor assembly delivery system of the present invention preferably comprises a needle or obturator adapted to pierce the tissue fold and deliver an anchor assembly. In one preferred embodiment, the anchor assembly comprises a pair of rod-like anchors that are delivered through a needle in a reduced delivery profile, wherein the longitudinal axis of the rods is substantially parallel to the longitudinal axis of the needle. Once ejected from the needle, the rods rotate about 90 degrees to engage the tissue. In other embodiments, the anchor assembly may comprise anchors of various shapes delivered, for example, over the exterior of an obturator.

In a preferred embodiment of the present invention, the catheter is adapted to form a plurality of gastrointestinal tissue folds that may be approximated. Optionally, an anchor assembly may be placed across each tissue fold, and the plurality of tissue folds then may be approximated by cinching the plurality of anchor assemblies together. Alternatively, an anchor assembly may be placed across a plurality of tissue folds, and the plurality of tissue folds may be approximated by cinching the anchor assembly. As yet another alternative, a plurality of tissue folds may be approximated prior to placement of an anchor assembly. One or more anchor assemblies then may be placed across the approximated plurality of tissue folds to secure the plurality in the approximated position. Multiple pluralities of tissue folds may be joined together and/or approximated in order to perform a procedure, for example, a gastric reduction or treatment of gastroesophageal reflux disease ("GERD").

To facilitate proper positioning, as well as visualization, of the tools and instruments of the present invention at a treatment site within a tortuous lumen or within unpredictably supported anatomy, a shape-lockable guide may be provided having a flexible state and reversibly rigidizable state. This guide may comprise an overtube through which instruments of the present invention, as well as an endoscope, may be advanced. As described hereinafter, exemplary procedures achievable when using tools of the present invention in conjunction with an endoscope include, for example, endoluminal gastric reduction and endoluminal treatment of GERD.

Methods of using the apparatus of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 5A and 5B are side-sectional views of another anchor assembly suitable for use with apparatus of the present invention;

FIGS. 6A and 6B are side-sectional views of another alternative anchor assembly suitable for use with apparatus of the present invention;

FIG. 13 is a schematic cross-sectional view of an alternative unidirectionally adjustable anchor assembly comprising spring material;

FIGS. 14A-14B are schematic side-sectional views of alternative unidirectionally adjustable anchor assemblies comprising one-way valves;

FIGS. 15A-15C are side-sectional and detail views of alternative unidirectionally adjustable anchor assemblies comprising slipknots;

FIGS. 17A-17D are perspective views of alternative anchors suitable for use with the anchor assemblies of the present invention;

FIG. 25 is a schematic side view, partially in section of an alternative anchor delivery system adapted to deliver a plurality of anchor assemblies;

FIG. 26 is a schematic side view of an alternative embodiment of the anchor delivery system of FIG. 25;

DETAILED DESCRIPTION OF THE INVENTION

In accordance with the principles of the present invention, methods and apparatus are provided for intraluminally forming and securing gastrointestinal ("GI") tissue folds, for example, to reduce the effective cross-sectional area of a GI lumen. These methods and apparatus may be used to treat obesity by approximating the walls of a gastrointestinal lumen to narrow the lumen, thus reducing the area for absorption in the stomach or intestines. More particularly, the present invention involves endoscopic apparatus that engages a tissue wall of the gastrointestinal lumen, creates one or more tissue folds and disposes one or more anchor assemblies through the tissue fold(s). Preferably, the anchor assemblies are disposed through the muscularis and/or serosa layers of the gastrointestinal lumen. In operation, a distal tip of the probe engages the tissue and then moves the engaged tissue to a proximal position relative to the catheter tip, thereby providing a substantially uniform plication of predetermined size.

Formation of a tissue fold preferably is accomplished using at least two tissue contact points that are separated by a linear or curvilinear distance, wherein the separation distance between the tissue contact points affects the length and/or depth of the fold. In operation, a tissue grabbing assembly engages the tissue wall in its normal state (i.e., non-folded and substantially flat), thus providing a first tissue contact point. The first tissue contact point then is moved to a position proximal of a second tissue contact point to form the tissue fold. An anchor assembly then may be extended across the tissue fold at the second tissue contact point. Optionally, a third tissue contact point may be established such that, upon formation of the tissue fold, the second and third tissue contact points are disposed on opposing sides of the tissue fold, thereby providing backside stabilization during extension of the anchor assembly across the tissue fold from the second tissue contact point.

Preferably, the first tissue contact point is used to engage and then stretch or rotate the tissue wall over the second tissue contact point to form the tissue fold. The tissue fold is then articulated to a position wherein a portion of the tissue fold overlies the second tissue contact point at an orientation that is substantially normal to the tissue fold. An anchor then is delivered across the tissue fold at or near the second tissue contact point.

Figure 1A:
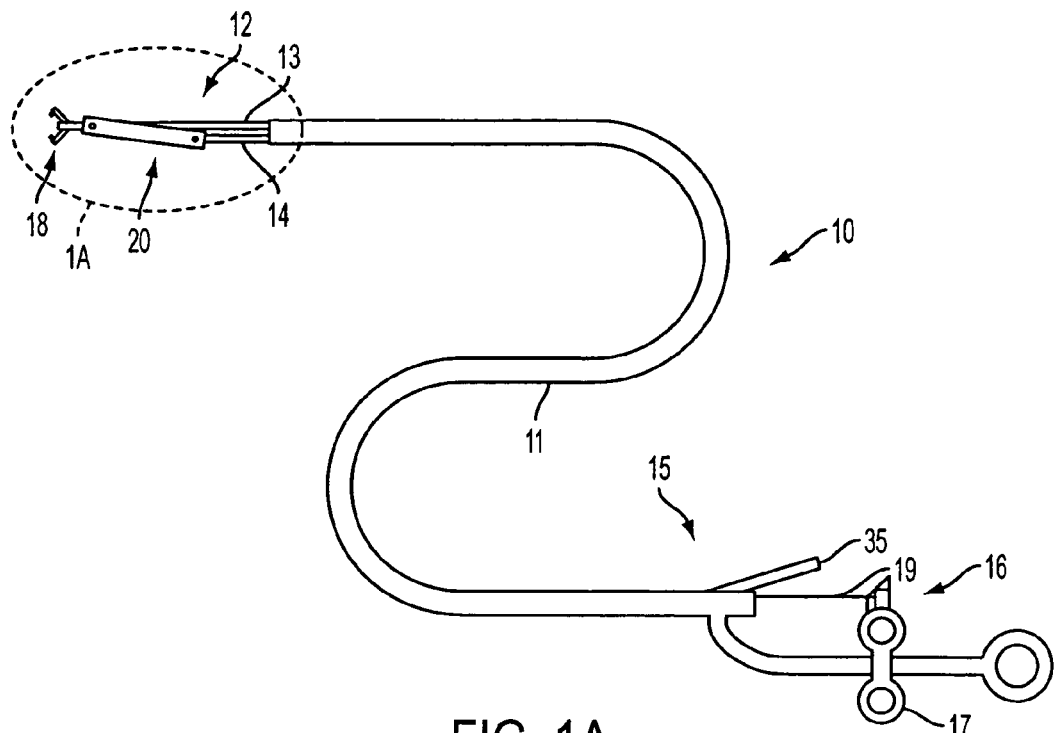
FIGS. 1A and 1B are, respectively, a side view and detail view of apparatus of the present invention for forming a gastrointestinal fold in accordance with the principles of the present invention.

Referring to FIG. 1, apparatus 10 of the present invention comprises torqueable catheter 11 having distal region 12 from which first and second interconnected flexible tubes 13 and 14 extend, and proximal region 15 having handle 16 and actuator 17. Catheter 11 is configured for insertion through a patient's mouth and esophagus into the gastrointestinal lumen. Tissue grabbing assembly 18 is disposed on the distal end of flexible tube 13, and is coupled to actuator 17 via control wire 19 that extends through flexible tube 13.

Figure 1B:
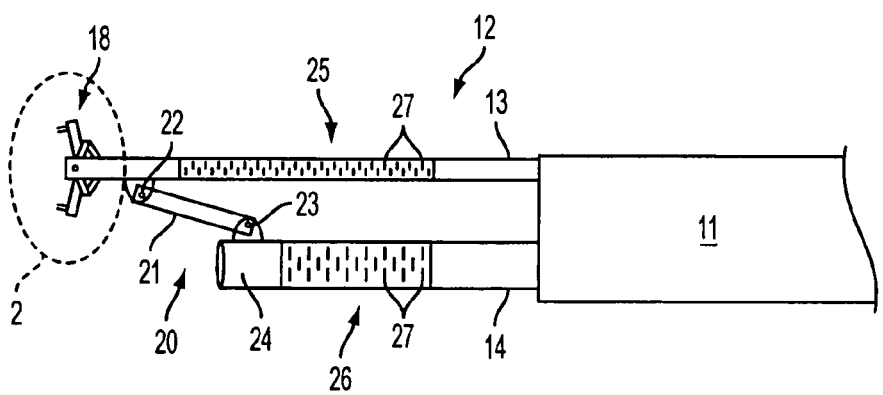

As better illustrated in FIG. 1B, flexible tubes 13 and 14 are connected via hinge assembly 20 that comprises link 21 attached to flexible tube 13 at pivot point 22 and attached to flexible tube 14 at pivot point 23. Hinge assembly 20 prevents tissue grabbing assembly 18 from moving more than a predetermined distance relative to distal end 24 of flexible tube 14.

Still referring to FIG. 1B, flexible tubes 13 and 14 preferably include bendable sections 25 and 26, respectively. The bendable sections may comprise, for example, a plurality of through-wall slots 27 to enhance flexibility of the tube. Preferably, flexible tubes 13 and 14 are made from stainless steel with an etched or laser-cut slot pattern. More preferably, the slot pattern is a sinusoidal repeating pattern of slots perpendicular to the longitudinal axis of tubes 13 and 14. Alternative flexible patterns will be apparent to those of skill in the art.

Figure 2A:
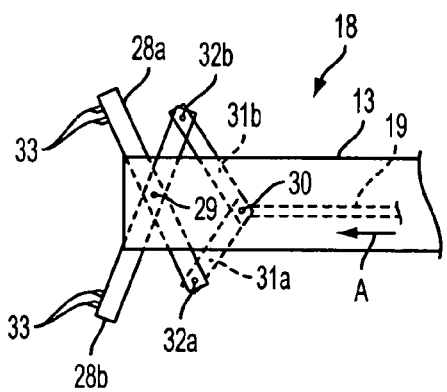
FIGS. 2A and 2B are side-sectional views of a tissue grabbing assembly suitable for use with the apparatus of FIG. 1.
Figure 2B:
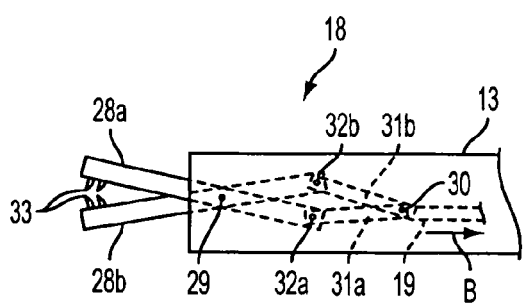

Referring to FIGS. 2A and 2B, tissue grabbing assembly 18 comprises pair of jaws 28a, 28b arranged to rotate about pivot point 29 between an open configuration (FIG. 2A) and a closed configuration (FIG. 2B). Control wire 19 is coupled via pivot point 30 to arms 31a and 31b. Arms 31a and 31b are in turn pivotally coupled to jaws 28a and 28b, respectively, at pivot points 32a and 32b. Each of jaws 28a and 28b preferably includes sharpened teeth 33 disposed near its distal ends to facilitate grasping of the tissue wall of the GI lumen.

Control wire 19 is coupled to actuator 17 of handle 16 so that translation of the wire within flexible tube 13 causes the jaws to open or close. In particular, urging control wire distally (as indicated by arrow A in FIG. 2A) moves pivot point 30 distally, thereby forcing the jaws to open. Urging control wire 19 proximally (as indicated by arrow B in FIG. 2B) moves pivot point 30 proximally, thereby forcing the jaws to close together. In alternative embodiments, tissue grabbing assembly 18 may comprise a grappling hook or fork, or plurality of needles coupled to the distal end of flexible tube 13.

Flexible tube 14 is affixed to and immovable within catheter 11, while flexible tube 13 is coupled to catheter 11 only via hinge 20. Accordingly, when control wire 19 is extended in the distal direction, flexible tube 13 is carried in the distal direction. When control wire 19 is retracted in the proximal direction, flexible tube remains stationary until jaws 28a and 28b close together, after which further retraction of control wire 19 by moving actuator 17 causes flexible tube 13 to buckle in bendable region 25, as described hereinafter.

Figure 3A:
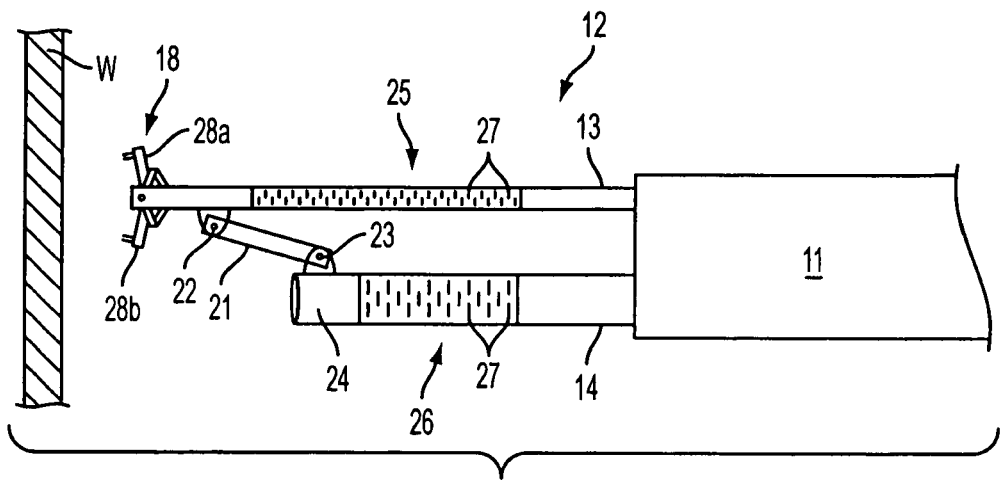
FIGS. 3A-3E are side views illustrating a method of using the apparatus of FIG. 1 to form a gastrointestinal fold.
Figure 3B:
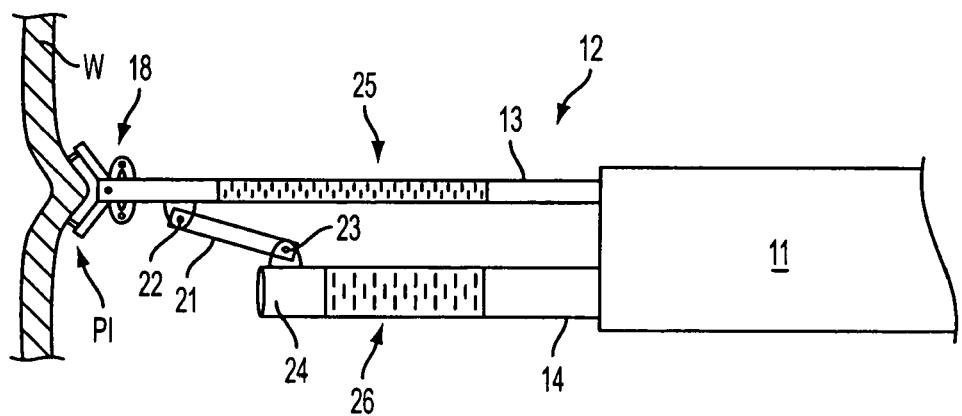

Referring now to FIGS. 1 and 3A-3E, operation of apparatus 10 is described to create a tissue fold in a tissue wall of a GI lumen. In FIG. 3A, distal region 12 of catheter 11 is positioned within a patient's GI lumen transesophageally, and jaws 28a and 28b of tissue grabbing assembly 18 are opened by moving actuator 17 to the distal-most position on handle 16. As depicted in FIG. 3B, actuator 17 may then be moved proximally until the jaws of tissue grabbing assembly 18 engage a portion of tissue wall W at contact point P1.

Figure 3C:
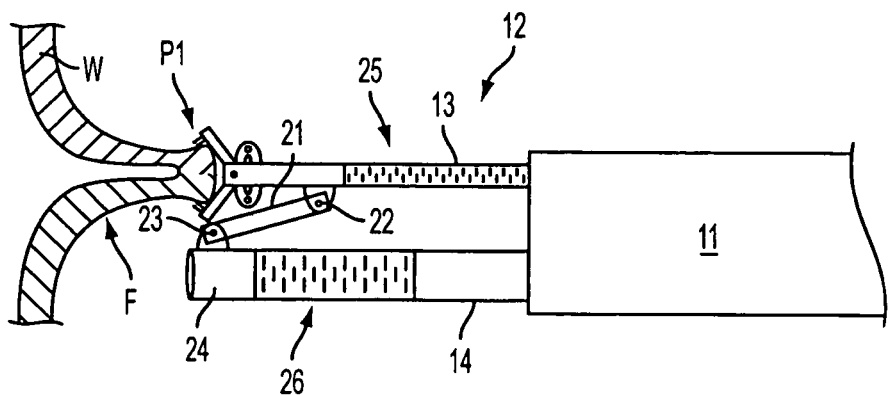

Referring to FIG. 3C, after the tissue wall has been engaged at contact point P1, flexible tube 13 is urged proximally within catheter 11 by further proximal retraction of control wire 19 to stretch tissue wall W and create tissue fold F. During this movement of flexible tube 13, link 21 of hinge assembly 20 causes tissue grabbing assembly 18 to move from a position distal to distal end 24 of flexible tube 14, to a position proximal of distal end 24 of flexible tube 14. Bendable sections 25 and 26 of flexible tubes 13 and 14, respectively, accommodate any lateral motion caused by operation of hinge assembly 20. Advantageously, formation of fold F facilitates the penetration of the tissue wall by a needle and subsequent delivery of an anchor assembly, as described hereinafter.

Figure 3D:
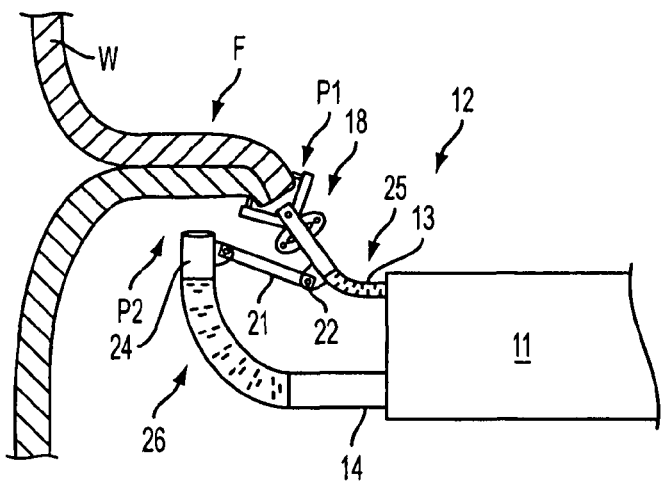
Figure 3E:
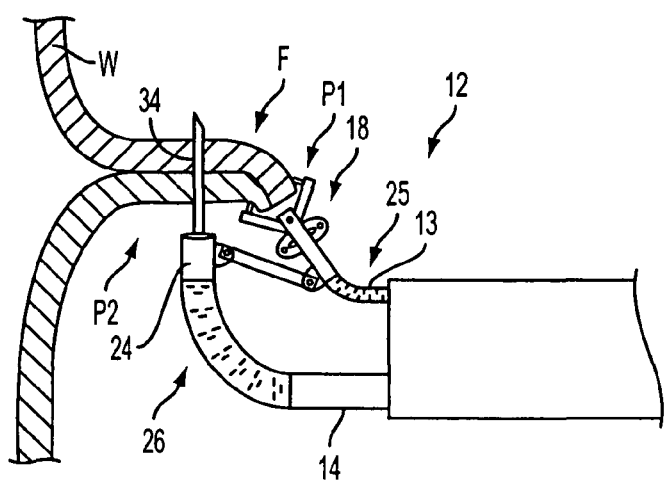

Referring to FIG. 3D, additional proximal movement of actuator 17 causes flexible tubes 13 and 14 to buckle at bendable sections 25 and 26. Hinge assembly 20 transmits force applied to flexible tube 13 via control wire 19 and actuator 17 to the distal tip 24. Preferably, flexible tube 14 is configured so that distal tip 24 contacts, and is substantially perpendicular, to tissue fold F at contact point P2. As illustrated in FIG. 3E, once tissue fold F is stretched across distal tip 24 of flexible tube 14, sharpened needle or obturator 34 may be extended from distal tip 24 of flexible tube 14 to pierce all four layers of the tissue wall W. Sharpened needle or obturator 34 is inserted via inlet 35 to flexible tube 14 on handle 16 (see FIG. 1A).

As discussed above, the GI lumen comprises an inner mucosal layer, connective tissue, the muscularis layer and the serosa layer. To obtain a durable purchase, e.g., in performing a stomach reduction procedure, the staples or anchors used to achieve reduction of the GI lumen must engage at least the muscularis tissue layer, and more preferably, the serosa layer as well. Advantageously, stretching of tissue fold F across distal tip 24 permits an anchor to be ejected through both the muscularis and serosa layers, thus enabling durable gastrointestinal tissue approximation.

As depicted in FIG. 3E, after tissue fold F is stretched across distal tip 24 of flexible tube 14 to form contact point P2 with tissue wall W, needle 34 may be extended from distal tip 24 and through tissue fold F. Because needle 34 penetrates the tissue wall twice, it exits within the gastrointestinal lumen, thus reducing the potential for injury to surrounding organs. Once the needle has penetrated tissue fold F, an anchor assembly is ejected through distal tip 24 as described hereinbelow.

Figure 4A:
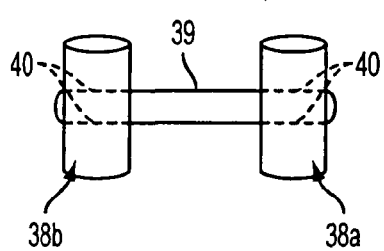
FIGS. 4A-4C are side-sectional views of an anchor assembly and delivery system suitable for use with apparatus of the present invention.
Figure 4B:
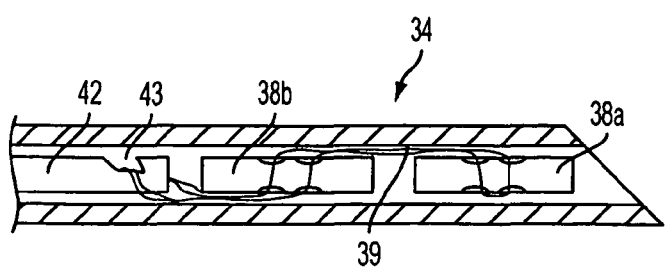
Figure 4C:
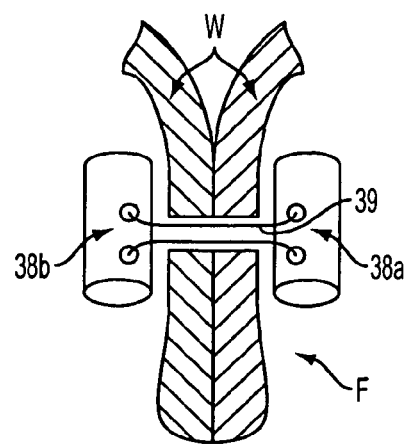

With respect to FIGS. 4A-4C, a first embodiment of an anchor assembly suitable for use with the apparatus of the present invention is described. Anchor assembly 36 comprises T-anchor assembly having distal rod 38a and proximal rod 38b connected by suture 39. The precise shape, size and materials of the anchors may vary for individual applications. In addition, the suture material also may vary for individual applications. By way of example, the suture material may consist of monofilament wire, multifilament wire or any other conventional suture material. Alternatively, suture 39 may comprise elastic material, e.g. a rubber band, to facilitate adjustment of the distance between the proximal and distal rods. Suture 39 extends through a pair of through-holes 40 in each rod, thereby forming a loop. Alternatively, suture 39 may be attached to the rods via an eyelet or using a suitable adhesive. Preferably, through-holes 40 are located near the center of the rods 38a and 38b.

Referring to FIG. 4B, rods 38a and 38b may be delivered through needle 34 (see FIG. 3E) using push rod 42. Push rod 42 is adapted to freely translate through flexible tube 14 and needle 34. Push rod 42 is preferably flexible, so that it may slide through bendable section 26 of flexible tube 14. In addition, push rod 42 may include notch 43 near its distal end to facilitate grasping and tensioning suture 39 after anchor delivery.

During anchor delivery, the longitudinal axis of distal rod 38a is substantially parallel to the longitudinal axis of needle 34. However, once distal rod 38a is ejected from needle 34, suture tension induces the rod to rotate approximately 90 degrees about its longitudinal axis, so that its longitudinal axis is substantially perpendicular to the longitudinal axis of needle 35. This rotation of distal rod 38a prevents it from being pulled back through tissue wall W.

Referring to FIG. 4C, once rod 38a is ejected on the distal side of fold F, needle 35 is retracted and push rod 42 is used to eject rod 38b on the proximal side of tissue fold F. Like distal rod 38a, tension in the suture causes proximal rod 38b to rotate about 90 degrees once it is ejected from the needle. Notch 43 in push rod 42 then may be employed to tighten suture 39 by any of a variety of mechanisms. Alternatively, suture 39 may comprise an elastic material that dynamically tightens the rods against tissue fold F.

Referring now to FIG. 5A, according to other embodiments, the anchor assembly comprises a T-anchor assembly suitable to be disposed over obturator 50. More particularly, distal rod 38a includes through-hole 51 dimensioned for the passage of obturator tip 52, and obturator 50 is translatably inserted through flexible tube 14 via inlet 35 of handle 16 (see FIG. 1A). Proximal rod 38b may be a solid rod that does not include a through-hole for passage of obturator 50. Alternatively, proximal rod 38b may include a through-hole for the passage of the obturator. Preferably, obturator tip 52 is sharpened to facilitate tissue penetration.

With respect to FIG. 5B, once rod 38a is ejected on the distal side of fold F, it rotates into a position substantially parallel to tissue wall W and perpendicular to the longitudinal axis of the obturator. Obturator 50 then is retracted and proximal rod 38b is ejected from flexible tube 14. More particularly, when flexible tube 14 is retracted from tissue wall W, proximal rod 38b is pulled through distal tip 24. Proximal rod 38b then rotates substantially 90 degrees as it is ejected from flexible tube 14 so that rod 38b is urged against tissue wall W.

Referring to FIG. 6A, according to further embodiments, anchor assembly 55 comprises a T-anchor assembly similar to the embodiment depicted in FIG. 4A. However, anchor assembly 55 includes fine wire tether 56 that may be twisted to maintain the tension between rods 38a and 38b.

With respect to FIG. 6B, a method of delivering anchor assembly 55 is described. Initially, distal rod 38a is delivered across both tissue walls using needle 34. The needle then is retracted to release distal rod 38a so that it engages the tissue wall. Next, needle 34 is retracted to release proximal rod 38b, so that it too rotates into engagement with the tissue wall. A proximal portion of the wire tether is captured by notch 43 of push rod 42 (see FIG. 4B), and the push rod is rotated to cause proximal rod 38b to clamp down on the tissue fold. Because wire tether 56 is twisted by rotation of push rod 42, it maintains the desired force on the tissue walls.

Figure 7A:
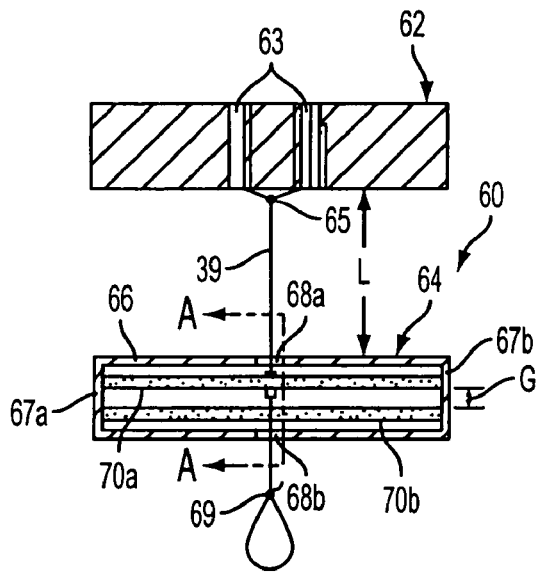
FIGS. 7A-7C are, respectively, a schematic side-sectional view of a unidirectionally adjustable anchor assembly suitable for use with apparatus of the present invention, schematic side-sectional views of alternative techniques for fixing the distal anchor of the assembly, and a cross-sectional view of the proximal anchor taken along section line A—A of FIG. 7A.

Referring now to FIG. 7, a unidirectionally adjustable anchor assembly suitable for use with apparatus of the present invention is described. Anchor assembly 60 comprises distal anchor 62 and unidirectionally adjustable proximal anchor 64, which are connected by suture 39. Distal anchor 62 is translationally fixed with respect to suture 39. Such fixation may be achieved in a variety of ways. For example, as seen in FIG. 7A, distal anchor 62 may comprise a pair of through-holes 63, located near the center of anchor 62 and through which suture 39 is threaded and tied off at knot 65.

Figure 7C:
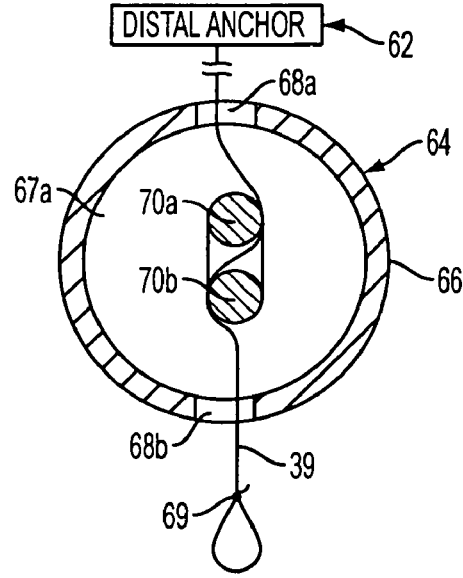
Figure 7B:
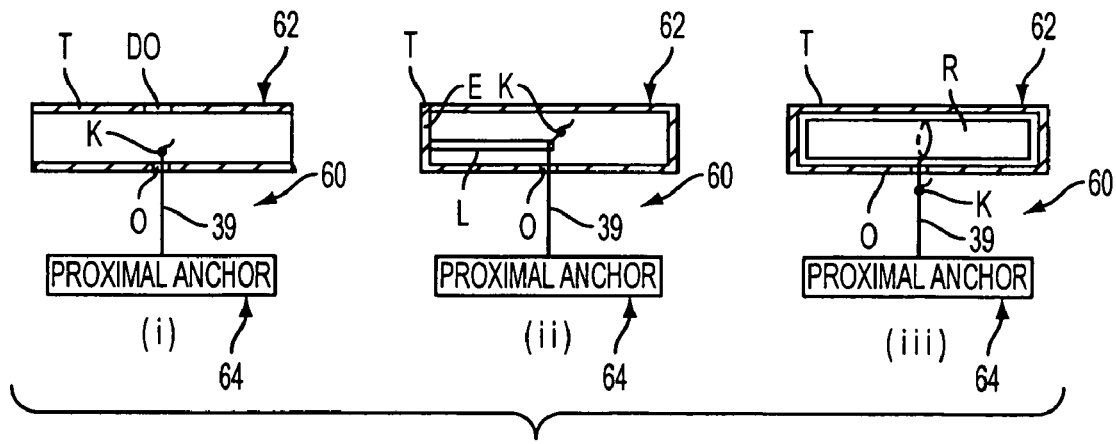

FIG. 7B provides alternative techniques for fixing the distal anchor. As seen in FIG. 7B(i), distal anchor 62 may comprise hollow tube T having opening O. A distal end of suture 39 is passed through opening O and formed into knot K, which is dimensioned such that it cannot pass through opening O, thereby fixing the distal anchor with respect to the suture. In order to facilitate formation of knot K, distal anchor 62 optionally may comprise distal opening DO, which is dimensioned such that knot K may pass therethrough. The distal end of suture 39 may be passed through distal opening DO, knotted, and then pulled back within hollow tube T of anchor 62 until it catches at opening O.

A drawback of the fixation technique described with respect to FIG. 7B(i) is a risk of suture 39 being torn or cut due to rubbing against opening O. In FIG. 7B(ii), hollow tube T comprises first end E to which is connected wire loop L, which may be formed, for example from a nickel-titanium alloy ("Nitinol"). Suture 39 passes through the wire loop before terminating at knot K. Knot K is dimensioned such that it cannot pass back through the wire loop. Wire loop L directs suture 39 through opening O, thereby reducing rubbing of the suture against the opening and reducing a risk of tearing or cutting of suture 39.

FIG. 7B(iii) provides yet another alternative technique for fixing the distal anchor with respect to the suture. Distal anchor 62 again comprises hollow tube T having opening O. Rod R is disposed within tube T, and the ends of the tube may be either closed or crimped to rod R, such that the rod is maintained within the tube. The distal end of suture 39 is threaded through opening O, around rod R, and back out opening O. The suture is then knotted at knot K, thereby fixing distal anchor 62 with respect to suture 39.

In addition to the techniques shown in FIGS. 7A and 7B, suture 39 alternatively may be fixed with respect to anchor 62 by other means, for example, via a knotted eyelet or via a suitable adhesive. Additional techniques will be apparent to those of skill in the art. While anchor 62 is illustratively shown as a rod- or T-type anchor, any of a variety of anchors, per se known, may be used as distal anchor 62. Exemplary anchors are described in co-pending U.S. patent application Ser. No. 10/612,170, filed Jul. 1, 2003, which is incorporated herein by reference in its entirety. Additional anchors are described hereinbelow with respect to FIG. 17. For the purposes of the present invention, anchors and anchor assemblies should be understood to include clips for securing tissue, as well as suture knots and knot replacements. Furthermore, anchor assemblies may comprise multiple components that are not initially coupled to one another; the components may be brought together and/or coupled within a patient at a treatment site.

Referring again to FIG. 7A, adjustable proximal anchor 64 comprises outer cylinder 66 having first end 67a and second end 67b, as well as first opening 68a and second opening 68b. First and second openings 68 are preferably disposed near the center of cylinder 66 and approximately 180° apart. Anchor 64 further comprises first flexible rod 70a and second flexible rod 70b, both of which are disposed within outer cylinder 66 and coupled to first and second ends 67 of cylinder 66. Rods 70 may be formed, for example, from Nitinol or from a polymer, and may be separated from one another by small gap G. As with the previous anchor assemblies, the precise shape, size and materials of the anchors and suture may vary as required for specific applications.

As best seen in FIG. 7C, suture 39 passes from distal anchor 62 through first opening 68a of proximal anchor 64, around second flexible rod 70b, around first flexible rod 70a, between rods 70a and 70b, and out through second opening 68b. This suture winding provides a unidirectional adjustment capability that allows a length L of suture 39 disposed between distal anchor 62 and proximal anchor 64 to be shortened. However, the suture winding precludes an increase in length L. FIG. 8 illustrate the mechanism of this unidirectional adjustment capability in greater detail. Optionally, suture 39 may be tied off proximal of anchor 64 at knot 69, thereby forming a proximal loop of suture to facilitate deployment and/or adjustment of anchor assembly 60.

Figure 8A:
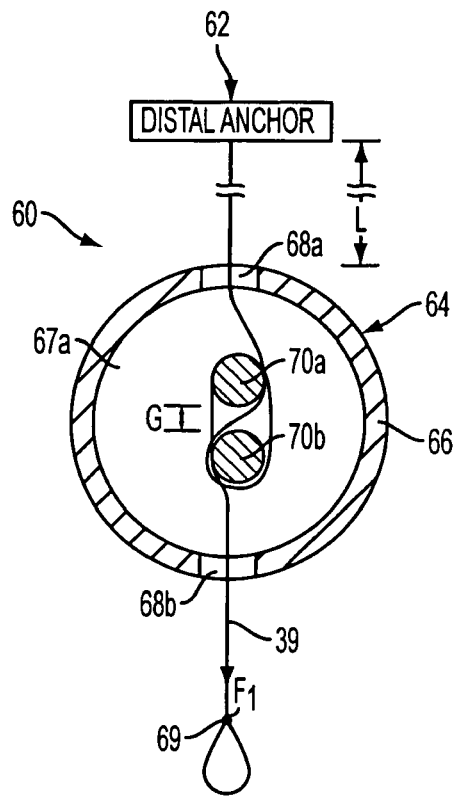
FIGS. 8A and 8B are schematic cross-sectional views illustrating the unidirectional adjustment capability of the anchor assembly of FIG. 7.

In FIG. 8A, a proximally-directed force $F_1$ is applied to suture 39 proximal of adjustable anchor 64, while anchor 64 is held stationary or is advanced distally. A portion of force $F_1$ is transferred through suture 39 to second flexible rod 70b, which causes rod 70b to bow, thereby increasing gap G and allowing suture 39 to freely pass between rods 70a and 70b and through proximal anchor 64, facilitating unidirectional adjustment. When anchor 64 is held stationary while suture 39 is retracted proximally, distal anchor 62 retracts proximally towards anchor 64. Alternatively, when anchor 64 is advanced distally while suture 39 is retracted proximally, distal anchor 62 either remains stationary or retracts proximally towards proximal anchor 64, depending upon a degree of distal advancement of proximal anchor 64. Regardless, length L of suture 39 disposed between anchors 62 and 64 is decreased, thereby unidirectionally adjusting a distance between the anchors.

Figure 8B:
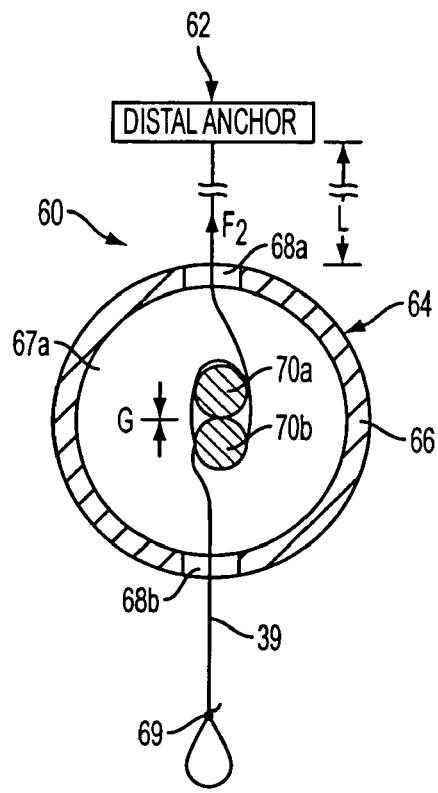

In FIG. 8B, a distally-directed force $F_2$ is applied to suture 39 distal of adjustable anchor 64. Force $F_2$ may be applied, for example, by tissue compressed between anchors 62 and 64. Compressed tissue stores energy in a manner similar to a compression spring and seeks to push anchors 62 and 64 apart after unidirectional tightening. Force $F_2$ causes the loop of suture 39 around first and second rods 70 to tighten, thereby bowing both rods inward and closing gap G such that suture 39 is friction locked between first and second flexible rods 70. In this manner, the length L of suture between anchors 62 and 64 may be selectively decreased but cannot be increased.

As will be apparent to those of skill in the art, the magnitude of force required to unidirectionally adjust length L may be altered in a variety of ways. For example, a length, flexibility or diameter of rods 70 may be altered. Likewise, the elasticity or diameter of suture 39 may be altered. Initial gap G may be increased or decreased. Furtherstill, the materials used to form rods 70 and suture 39 may be changed to alter material properties, such as coefficients of friction, and/or rods 70 or suture 39 may comprise a lubricious coating. Additional methods for varying the magnitude of force, a few of which are described hereinbelow with respect to FIG. 9, will be apparent in view of this disclosure and are included in the present invention.

Figure 9A:
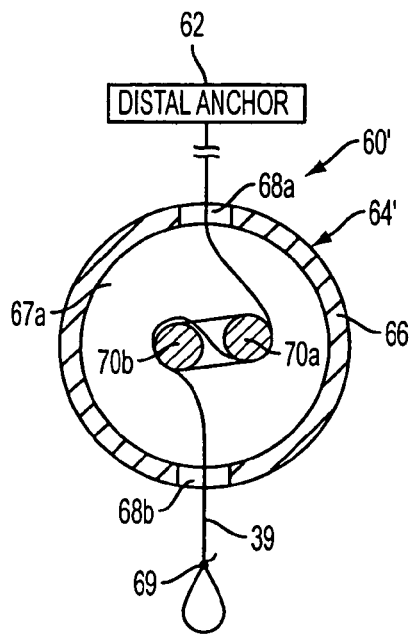
FIGS. 9A-9C are schematic cross-sectional views of alternative embodiments of the proximal anchor of the anchor assembly of FIG. 7.

Referring now to FIG. 9, alternative anchors 64 are described. In FIG. 9A, flexible rods 70 of proximal adjustable anchor 64' are rotated with respect to openings 68 (or vice versa). When utilizing the suture winding described in FIGS. 7 and 8, rotation of rods 70 up to 180° clockwise progressively increases friction when force is applied to anchors 62 and 64. The magnitude of the friction lock is increased when force is applied in the manner described with respect to FIG. 8B. However, friction is also increased when unidirectionally adjusting the length of suture between the proximal and distal anchors by applying force in the manner described with respect to FIG. 8A. Rotation of rods 70 more than about 180° clockwise would cause anchor 64' to friction lock regardless of which direction force were applied to suture 39, thereby negating the unidirectional adjustment capability. Counterclockwise rotation of rods 70 with respect to openings 68 would initially reduce friction during force application to suture 39 in either direction. It is expected that counterclockwise rotation in excess of about 90° would eliminate the friction lock described in FIG. 8B and allow bidirectional adjustment. Continued counterclockwise rotation beyond about 450° would reverse the directions of friction lock and unidirectional adjustment, while counterclockwise rotation beyond about 720° would result in friction lock regardless of which direction force were applied to suture 39.

As discussed previously, openings 68 of cylinder 66 of anchor 64 are preferably disposed approximately 180° apart from one another. However, in order to increase the friction lock force without significantly increasing friction during unidirectional adjustment, first opening 68a may be rotated counterclockwise with respect to second opening 68b (or vice versa), as seen with anchor 64" of FIG. 9B. In this manner, first opening 68a is no longer in line with rods 70, while second opening 68b remains in line with rods 70. When force $F_1$ is applied to anchor 64", second flexible rod 70b is able to bow outward and increase gap G, thereby facilitating unidirectional adjustment. Likewise, when force $F_2$ is applied to the anchor, gap G is closed more tightly upon suture 39, thereby increasing the friction lock force. If first opening 68a alternatively were rotated clockwise with respect to the second opening, it is expected that the friction lock force would be decreased.

Figure 9B:
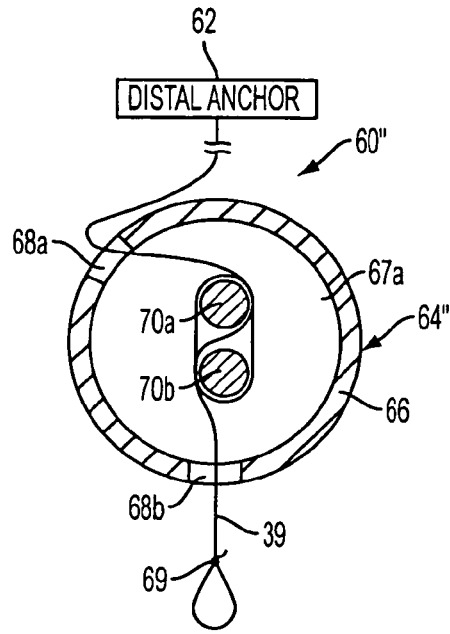
Figure 9C:
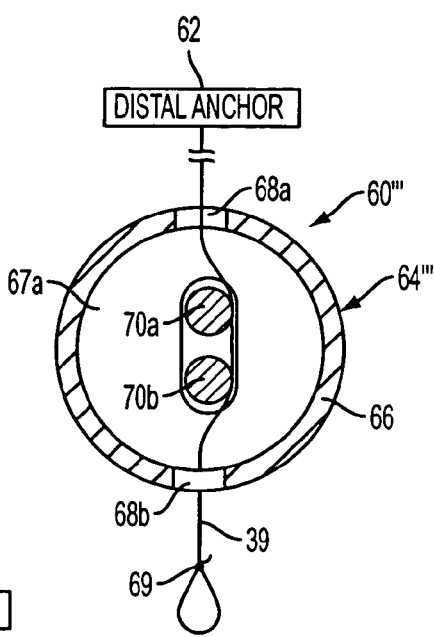

In FIG. 9C, proximal adjustable anchor 64''' comprises an alternative suture winding. Suture 39 passes from distal anchor 62 through first opening 68a of anchor 64''', around second flexible rod 70b, around first flexible rod 70a, back around second flexible rod 70b, between rods 70a and 70b, and out through second opening 68b. As with the suture winding described with respect to anchor 64 of FIGS. 7 and 8, the suture winding illustrated in FIG. 9C provides a unidirectional adjustment capability that allows a length L of suture 39 disposed between distal anchor 62 and proximal anchor 64''' to be shortened. However, this suture winding precludes an increase in length L. Additional unidirectionally adjustable suture windings will be apparent to those of skill in the art.

With reference to FIG. 10, an alternative unidirectionally adjustable anchor comprising three rods is described. Anchor assembly 80 comprises distal anchor 62 and proximal anchor 82. Unidirectionally adjustable proximal anchor 82 comprises outer cylinder 84 having first end 85a and second end 85b (not shown), as well as first opening 86a and second opening 86b. First and second openings 86 are preferably disposed near the center of cylinder 84 and approximately 180° apart. Anchor 82 further comprises first flexible rod 88a, second flexible rod 88b and third flexible rod 88c, all of which are disposed within outer cylinder 66 and coupled to first and second ends 85 of cylinder 64. Rods 88 are separated from one another by gaps $G_1$ and $G_2$.

Figure 10A:
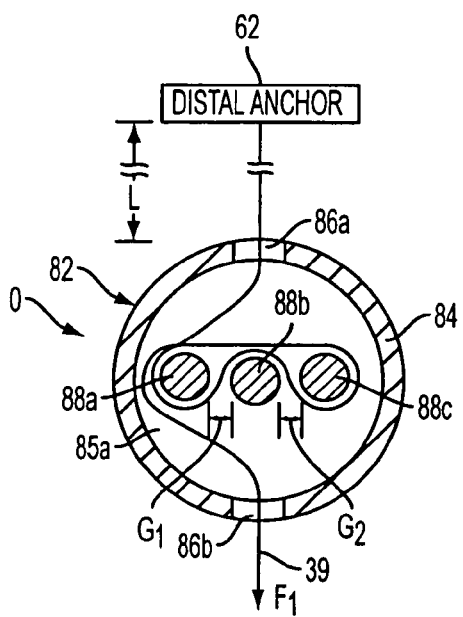
FIGS. 10A and 10B are schematic cross-sectional views of an alternative unidirectionally adjustable anchor assembly suitable for use with apparatus of the present invention.
Figure 10B:
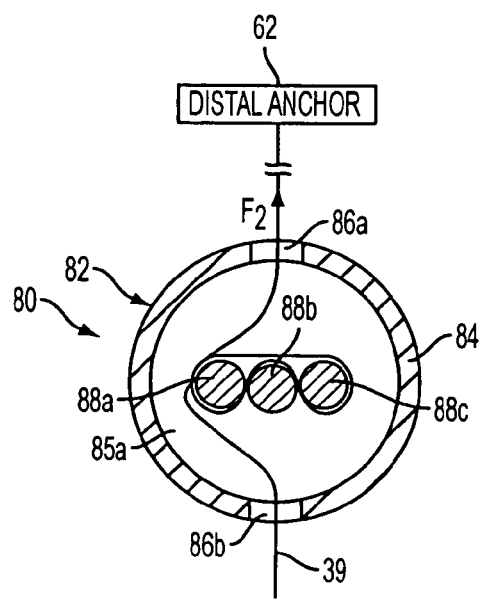

Suture 39 passes from distal anchor 62 through first opening 86a of proximal anchor 82, around first rod 88a, between first rod 88a and second rod 88b, between second rod 88b and third rod 88c, around third rod 88c, back to and around first rod 88a, and out through second opening 86b. As seen in FIG. 10A, when force $F_1$ is applied to suture 39, gaps $G_1$ and $G_2$ remain open, thereby facilitating unidirectional adjustment/shortening of length L of suture 39 disposed between distal anchor 62 and proximal anchor 82. As seen in FIG. 10B, when force $F_2$ is applied to suture 39, gaps $G_1$ and $G_2$ close down upon suture 39, thereby forming a friction lock that precludes an increase in length L of suture 39.

Referring now to FIG. 11, an alternative three rod anchor assembly is described. The unidirectionally adjustable anchors described hereinabove with respect to FIGS. 7-10 all comprise rods disposed within a cylinder having openings for passage of a suture. The openings act to center the suture with respect to the rods and can be used to alter magnitudes of force applied during adjustment and friction locking, as discussed previously. However, such openings present a risk of tearing or cutting the suture as the suture slides through the openings.

As seen in FIG. 11, anchor assembly 90 comprises distal anchor 62 and proximal anchor 92. Unidirectionally adjustable proximal anchor 92 comprises first flexible rod 94a and second flexible rod 94b, as well as rigid rod 96, which is preferably larger in diameter than first and second rods 94. Flexible rods 94 are preferably fabricated from Nitinol or a polymer, while rigid rod 96 is preferably fabricated from stainless steel or a polymer. Alternative materials will be apparent to those of skill in the art.

Anchor 92 further comprises first outer cylinder 98a and second outer cylinder 98b, which are crimped to the ends of first and second rods 94, and rigid rod 96. As an alternative to crimping, first and second cylinders 98 may each comprise an end cap (not shown) to which the rods are coupled. First and second cylinders 94 do not span a central portion of anchor 92. Flexible rods 94 are separated from one another by gap $G_1$, while rods 94 are separated from rigid rod 96 by gap $G_2$.

Figure 11A:
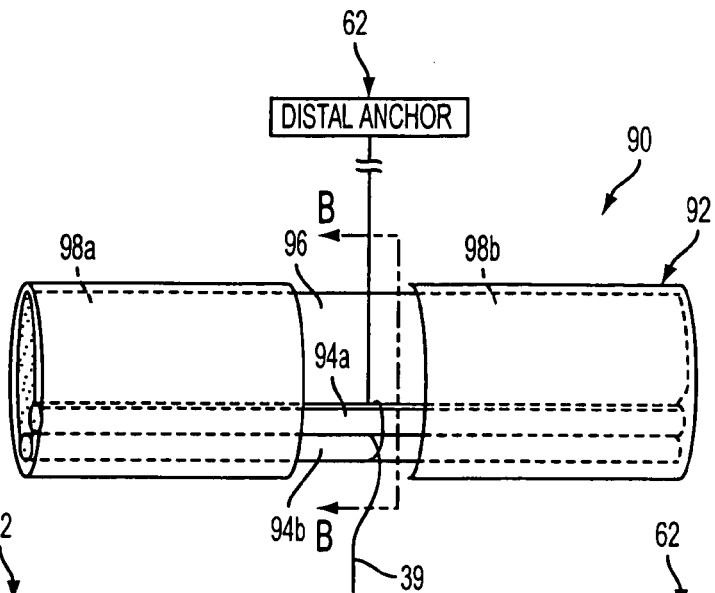
FIGS. 11A-11C are, respectively, a schematic side-view of another alternative unidirectionally adjustable anchor assembly suitable for use with the present invention, and cross-sectional views of the same taken along section line B—B of FIG. 11A.
Figure 11B:
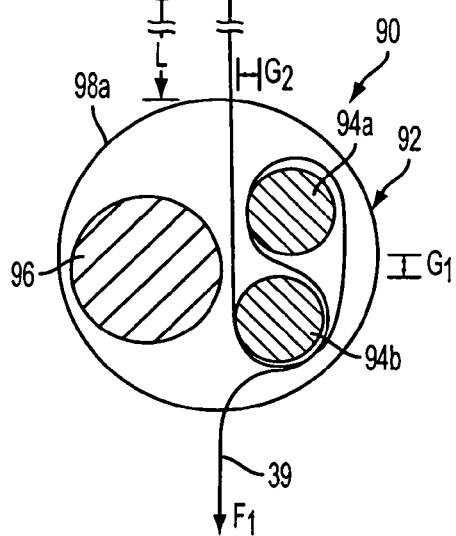
Figure 11C:
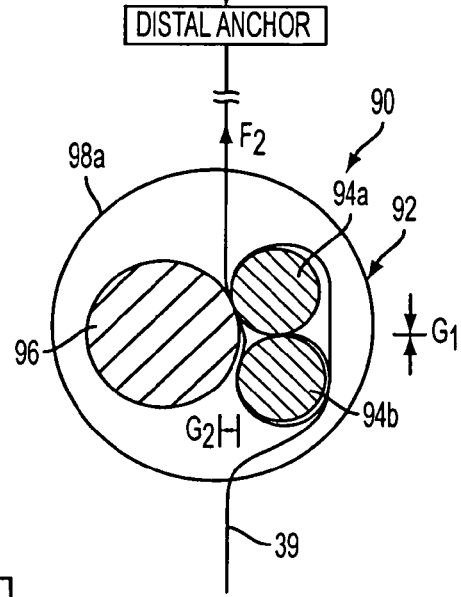

Anchor 92 comprises three rods, but, unlike anchor 82 of FIG. 10, suture 39 is only wrapped around two of them to achieve unidirectional adjustment. As best seen in FIGS. 11B and 11C, the illustrative suture winding of anchor assembly 90 is similar to that described previously with respect to anchor assembly 60 of FIGS. 7 and 8. The break between first and second cylinders 98 acts to center suture 39 with respect to the rods, as seen in FIG. 11A, while rigid rod 96 acts to stiffen and reduce rotation of anchor 92 as it directs suture 39 about flexible rods 94.

Suture 39 passes from distal anchor 62 to proximal anchor 92, between rigid rod 96 and flexible rods 94, around second flexible rod 94b, around first flexible rod 94a, between rigid rod 96 and first flexible rod 94a, between flexible rods 94a and 94b, and out. As seen in FIG. 11A, when force $F_1$ is applied to suture 39, flexible rods 94 are forced apart and gap $G_1$ widens while gap $G_2$ remains substantially constant, thereby allowing unidirectional adjustment of length L of suture 39 disposed between distal anchor 62 and proximal anchor 92. As seen in FIG. 11B, when force $F_2$ is applied to suture 39, gap $G_1$ closes down upon suture 39, thereby forming a friction lock that precludes an increase in length L of suture 39. Gap $G_2$ again remains substantially constant.

Figure 12:
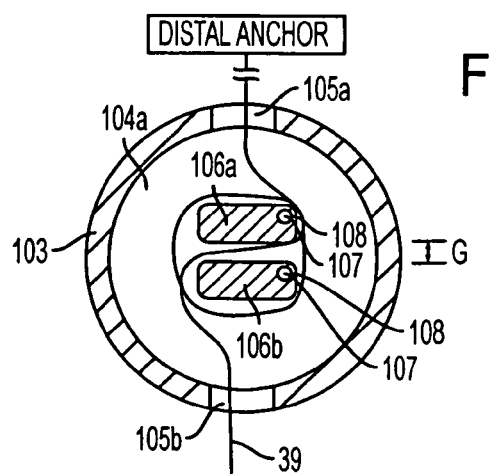
FIG. 12 is a schematic cross-sectional view of an alternative unidirectionally adjustable anchor assembly comprising pivoting paddles.

With reference to FIG. 12, an alternative unidirectionally adjustable anchor assembly comprising pivots is described. Anchor assembly 100 comprises distal anchor 62 and proximal anchor 102. Unidirectionally adjustable proximal anchor 102 comprises outer cylinder 103 having first end 104a and second end 104b (not shown), as well as first opening 105a and second opening 105b. First and second openings 105 are preferably disposed near the center of cylinder 103 and approximately 180° apart. Anchor 102 further comprises first rod or paddle 106a and second rod or paddle 106b, both of which are disposed within outer cylinder 103 and coupled to the first and second ends of cylinder 103 by pins 107, which pass through pivot holes 108. In this manner, first and second paddles 106 are able to rotate about pivot holes 108. Paddles 106 may be formed, for example, from stainless steel or a polymer, and are separated from one another by gap G. As with the previous anchor assemblies, the precise shape, size and materials of the anchors, as well as suture 39, may vary as required for specific applications.

Suture 39 illustratively passes from distal anchor 62 through first opening 105a of proximal anchor 102, around second paddle 106b, around first paddle 106a, between paddles 106a and 106b, and out through second opening 105b. The placement of pivot holes 108 ensures that application of force $F_1$, as described hereinabove, causes paddles 106 to rotate apart from one another and expand gap G, thereby enabling unidirectional adjustment. Likewise, application of previously discussed force $F_2$ causes paddles 106 to rotate together, thereby closing gap G and pinching suture 39 between the paddles in a friction lock. An increase in the magnitude of force $F_2$ serves to rotate paddles 106 together more tightly, thereby increasing the magnitude of the friction lock acting upon suture 39 between the paddles. In this manner, unidirectional adjustment is achieved.

Referring now to FIG. 13, an alternative unidirectionally adjustable anchor assembly comprising spring material is described. Anchor assembly 110 comprises distal anchor 62 and proximal anchor 112. Unidirectionally adjustable proximal anchor 112 comprises outer cylinder 113 having first end 114a and second end 114b (not shown), as well as first opening 115a and second opening 115b. First and second openings 115 are preferably disposed near the center of cylinder 113 and approximately 180° apart. Anchor 112 further comprises first rod 116a and second rod 116b that are separated by gap G, as well as spring material 118, all of which are disposed within outer cylinder 113. Spring material 118 abuts rods 116, which preferably are substantially the same length as cylinder 113, and may either move freely within cylinder 113 or may be coupled to the ends (not shown) of cylinder 113. Spring material 118 may also move freely within cylinder 113 or may be coupled to the cylinder, and comprises lumen 119 having a diameter that is preferably equal to or less than the diameter of suture 39. Spring material 118 may comprise, for example, a compressible biocompatible foam, which acts as a compression spring.

Suture 39 passes from distal anchor 62 to proximal anchor 112 through first opening 115a of cylinder 113, between rods 116, through lumen 119 of spring material 118, and out through second opening 115b. Lumen 119 snugly contacts suture 39 such that application of force $F_1$ causes friction between the suture and the spring material to compress the spring material against the wall of cylinder 114, thereby reducing a stress applied to rods 116 by spring material 118 and increasing gap G such that unidirectional adjustment of length L of suture 39 disposed between distal anchor 62 and proximal anchor 102 may proceed. Application of force $F_2$ stretches spring material 118 against rods 116, thereby increasing the stress applied to the rods by the spring material and closing gap G such that suture 39 is friction locked between rods 116.

With reference to FIG. 14, alternative unidirectionally adjustable anchor assemblies comprising one-way valves are described. In FIG. 14A, anchor assembly 120 comprises distal anchor 62 and proximal anchor 122. Unidirectionally adjustable proximal anchor 122 comprises outer cylinder 124 having first and second ends 125a and 125b, as well as first opening 126a and second opening 126b. First and second openings 126 are preferably disposed near the center of cylinder 124 and approximately 180° apart. Anchor 122 further comprises first inclined plane 128a and second inclined plane 128b, which are forced into apposition by compression springs 129a and 129b, thereby forming one-way valve V at the junction of the two inclined planes. Inclined planes 128 and springs 129 are disposed within outer cylinder 124; springs 129 abut ends 125 of cylinder 124, as well as the ends of the inclined planes. Suture 39' comprises a plurality of knots or beads B adapted to actuate one-way valve V.

Suture 39' passes from distal anchor 62 to proximal anchor 122 through first opening 126a of cylinder 124, between inclined planes 128, through one-way valve V, and out through second opening 126b. Application of force $F_1$ to suture 39' causes a bead B to contact inclined planes 128 and gradually coax them apart by compressing springs 129, thereby opening valve V and allowing the bead to pass through the valve. Once the bead has passed through valve V, springs 129 force inclined planes 128 back into apposition, thereby closing the valve. Continued application of force $F_1$ allows multiple beads to pass through the valve, which facilitates unidirectional adjustment of suture length L disposed between distal anchor 62 and proximal anchor 122. Application of force $F_2$ causes a bead B of suture 39' to impinge upon the proximal sides of inclined planes 128. However, force transferred to the planes by the bead is perpendicular to the direction required to compress springs 129 and urge planes 128 apart. As such, the bead B impinging upon the proximal sides of planes 128 is not able to open one-way valve V and pass back through the valve in a distal direction, thereby ensuring only unidirectional adjustment, i.e. shortening, of the length L of suture disposed between the proximal and distal anchors.

In FIG. 14B, an alternative unidirectionally adjustable anchor having a one-way valve is described. Anchor assembly 130 comprises distal anchor 62 and proximal anchor 132. Unidirectionally adjustable proximal anchor 132 comprises lumen 134 having cantilevered inclined plane 136 disposed therein, which forms one-way valve V. 'Zip-tie' fastener 138, having a plurality of inclined planes 139, connects proximal anchor 132 and distal anchor 62. The plurality of inclined planes 139 are disposed about 180° out of phase with inclined plane 136 of anchor 132.

Fastener 138 passes from distal anchor 62 to proximal anchor 132, through lumen 134 and past inclined plane 136. Inclined planes 139 of fastener 138 mesh with inclined plane 136 and bend or cantilever plane 136, such that planes 139 of fastener 138 may proximally pass one-way valve V when force $F_1$ is applied to the fastener, thereby enabling unidirectional adjustment of length L of fastener 138 disposed between the proximal and distal anchors. Conversely, when force $F_2$ is applied to the fastener, the proximal side of inclined plane 136 of anchor 132 abuts the distal side of an inclined plane 139 of fastener 138, and the fastener cannot be drawn distally through proximal anchor 132, nor can the length L of fastener disposed between the anchors be increased significantly.

Referring now to FIG. 15, alternative unidirectionally adjustable anchor assemblies comprising a slipknot are described. In FIG. 15A, anchor assembly 140 comprises distal anchor 142 and proximal anchor 144. Through-holes 143a and 143b extend through distal anchor 142, while through-holes 145a and 145b extend through proximal anchor 145. Preferably, through-holes 143 and 145 are located near the center of anchors 142 and 144, respectively.

The distal end of suture 39 passes through through-hole 145a of proximal anchor 144 to distal anchor 142, where it passes through through-hole 143a and back through through-hole 143b. It then extends from distal anchor 142 back to proximal anchor 144, where it passes through through-hole 145b of the proximal anchor. The distal end of suture 39 is tied off at unidirectional slipknot S, which is located proximal of anchor 144. FIG. 15B provides a detail view illustrating formation of slipknot S.

As will be apparent to those of skill in the art, application of force $F_1$ causes suture 39 to slide through through-holes 143 and 145, and decrease the length L of suture 39 disposed between anchors 142 and 144. Suture 39 may readily pass through slipknot S in a proximal direction, thereby facilitating unidirectional adjustment of length L. However, application of force $F_2$ tightens slipknot S and prohibits passage of suture 39 through the slipknot in a distal direction, thereby precluding an increase in length L.

FIG. 15C illustrates an alternative embodiment of anchor assembly 140 wherein the slipknot is disposed within the proximal anchor. Anchor assembly 140' comprises distal anchor 142 and proximal anchor 144'. Proximal anchor 144' comprises hollow cylinder or tube 146 having distal openings 147a and 147b, and proximal opening 148.

The distal end of suture 39 passes through proximal opening 148 into the interior of tube 146. It then passes through distal opening 147a of proximal anchor 144' to distal anchor 142, where it passes through through-hole 143a and back through through-hole 143b. Next, suture 39 extends from distal anchor 142 back to proximal anchor 144', where it passes through distal opening 147b into the interior of tube 146 of the proximal anchor. The distal end of suture 39 is tied off at unidirectional slipknot S, which is disposed within tube 146 of anchor 144'. Anchor assembly 140' may be unidirectionally adjusted in a manner similar to that described hereinabove with respect to anchor assembly 140 of FIG. 15A.

FIGS. 7-15 have illustrated anchor assemblies comprising various mechanisms for achieving unidirectional adjustment of the distance between the proximal and distal anchors. These mechanisms have been provided solely for the sake of illustration and should in no way be construed as limiting. Additional mechanisms for achieving unidirectional adjustment will be apparent to those of skill in the art in view of this disclosure and are included in the present invention. Furthermore, a majority of the anchor assemblies of FIGS. 7-15 have been described with the distal anchor being fixed relative to the suture, and the proximal anchor being adjustable. However, it should be understood that the distal anchor may alternatively be adjustable and the proximal anchor may be fixed, and/or both anchors may be unidirectionally adjustable, as with anchor assembly 140 of FIG. 15.

Figure 16A:
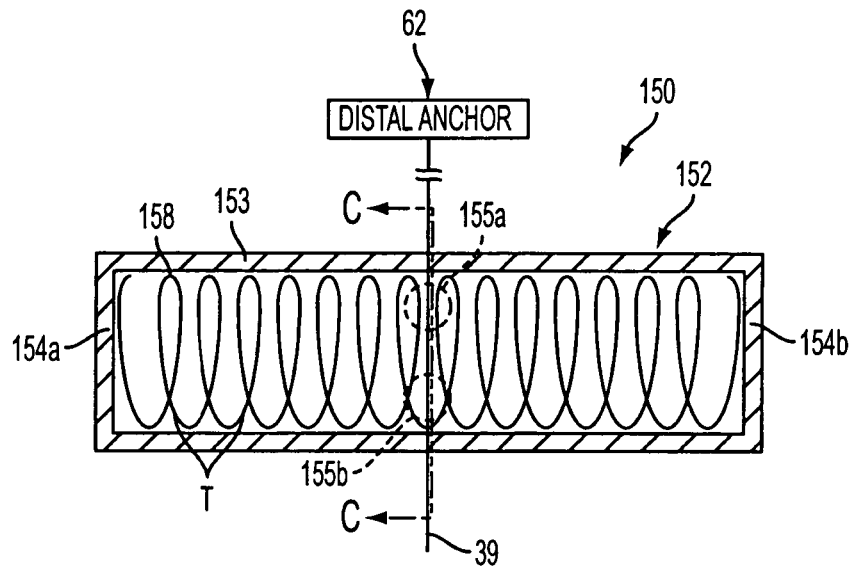
FIGS. 16A-16C are, respectively, a schematic side-sectional view of a bi-directionally adjustable anchor assembly comprising a locking mechanism, and cross-sectional views of the same taken along section line C—C of FIG. 16A.

With reference now to FIG. 16, a bi-directionally adjustable anchor assembly comprising a locking mechanism is described. Anchor assembly 150 comprises distal anchor 62 and proximal anchor 152. As seen in FIG. 16A, bi-directionally adjustable proximal anchor 152 comprises outer cylinder 153 having first end 154a and second end 154b, as well as first opening 155a and second opening 155b. First and second openings 155 are preferably disposed near the center of cylinder 153 and approximately 90° apart. Proximal anchor 152 further comprises tension spring 158 disposed within outer cylinder 153.

Figure 16B:
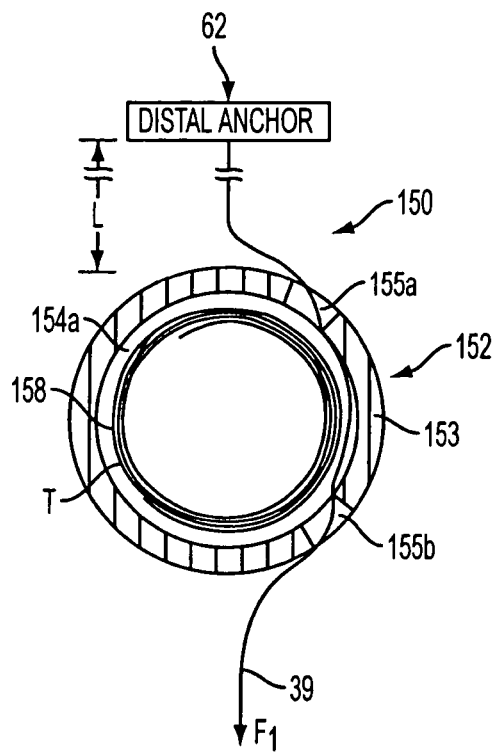
Figure 16C:
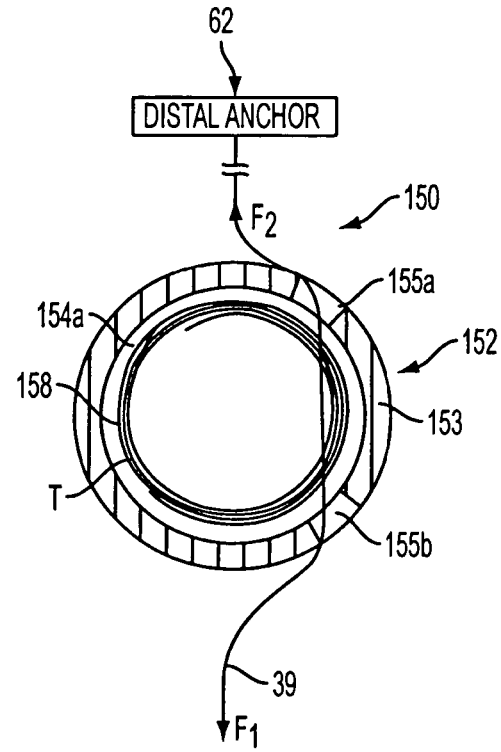

As seen in FIG. 16B, suture 39 passes from distal anchor 62 to proximal anchor 152 through first opening 155a, around spring 158, and out through second opening 155b. Suture 39 moves freely about tension spring 158 in either direction during application of force $F_1$ or force $F_2$, thereby facilitating bi-directional adjustment of suture length L disposed between the proximal and distal anchors. However, as seen in FIG. 16C, simultaneous application of forces $F_1$ and $F_2$ with sufficient magnitude causes suture 39 to force threads T of spring 158 apart, such that suture 39 is trapped between threads T and locked in position, thereby precluding further adjustment of suture length L.

The magnitude of forces required to actuate the locking mechanism of proximal anchor 152 and lock suture 39 within threads T of spring 158 may be specified/altered in a variety of ways. For example, the angular spacing of openings 155 about outer cylinder 153 may be altered, the spring constant of spring 158 may be specified, and/or spring 158 or suture 39 may comprise a lubricious coating. Additional techniques will be apparent to those of skill in the art. It is expected that simultaneous application of forces $F_1$ and $F_2$ will be encountered when anchor assembly 150 has been deployed across a tissue fold and suture length L has been adjusted such that the tissue fold is compressed. A medical practitioner would then apply force $F_1$, while the compressed tissue fold would apply force $F_2$.

Although the anchor assemblies of FIGS. 10-16 have illustratively been described without knots or loops of suture or fastener disposed proximal of the proximal anchor (as seen, for example, with knot 69 on suture 39 of anchor assembly 60 in FIGS. 7 and 8) it should be understood that such loops or knots optionally may be provided in order to facilitate deployment and/or adjustment of the anchor assemblies. Additionally, the previously described anchor assemblies illustratively comprise distal rod- or T-type anchors. However, it should be understood that distal T-anchors have only been provided for the sake of illustration. The distal anchors (as well as the proximal anchors) may comprise any of a variety of anchors, per se known, including, for example, surgical or endoluminal clips, clips for securing tissue and suture knots or knot replacements. Exemplary anchors are described in co-pending U.S. patent application Ser. No. 10/612,170, filed Jul. 1, 2003, which is incorporated herein by reference in its entirety. Furthermore, anchor assemblies may comprise multiple components that are not initially coupled to one another; the components may be brought together and/or coupled within a patient at a treatment site. Additional anchors are described hereinbelow with respect to FIG. 17.

Referring to FIG. 17A, articulating anchor 160 includes semi-cylindrical base 161, rod 162 and suture 39. Rod 162 rotates about pivot point 163 (as indicated by arrow 164) between an expanded position (shown in FIG. 7A) and a reduced profile position, wherein rod 162 pivots within the semi-cylindrical base 161. Articulating anchor 160 may be delivered through a tissue fold using, for example, needle 34 described hereinabove with respect to FIG. 3E. Preferably, articulating anchor 160 is biased in the expanded position so that it automatically expands once it is ejected from the needle.

With respect to FIGS. 17B and 17C the anchors of the present invention also may comprise one or more oblong bodies connected by at least one suture. In FIG. 17B, anchor 165 comprises elliptical ring 166 having sutures 39 attached at substantially opposite sides of the ring. In FIG. 17C, anchor 168 comprises angle bracket 169 having a pair of through-holes 170 for suture 39. In FIG. 17D, anchor 171 comprises oblong bead 172 having a pair of through-holes 173 for suture 39. All three anchors 165, 168 and 171 (as well as the T-anchors described previously) have a first dimension (e.g., width) that is substantially larger than a second dimension (e.g., height). This dimensional difference necessitates that anchors 165, 168 and 171 be inserted within a needle (e.g., needle 34 of FIG. 3E) in a particular orientation. Once the anchor is ejected through a tissue wall, tension on suture 39 forces the anchor to rotate so that it cannot be pulled back through the tissue wall. As will be understood by those of skill in the art, numerous other anchors may be employed without departing from the scope of the present invention.

Figure 18A:
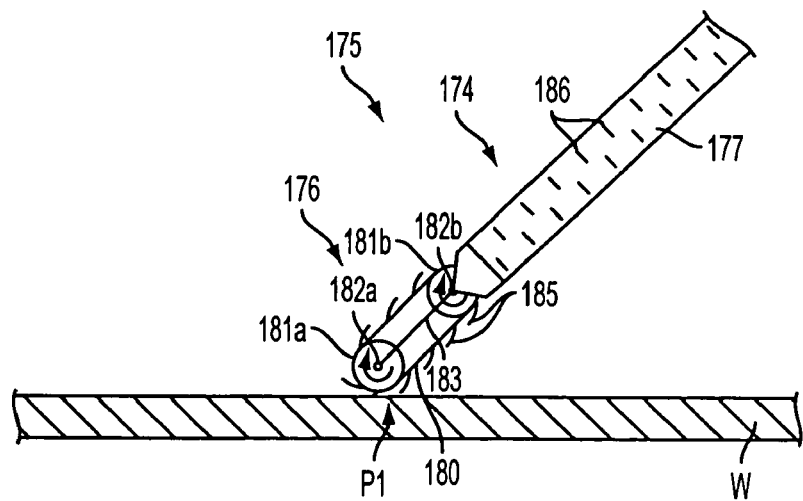
FIGS. 18A-18D are side views of alternative apparatus for forming a gastrointestinal fold.

Referring now to FIG. 18A, an alternative embodiment of apparatus for forming a tissue fold, constructed in accordance with the principles of the present invention, is described. Apparatus 175 comprises treadmill assembly 176 disposed at distal tip 174 of flexible tube 177. Flexible tube 177 is configured to be inserted through a patient's mouth, esophagus and into the stomach. Treadmill assembly 176 comprises conveyor 180 that circles around a pair of hubs 181a and 181b. Hubs 181a and 181b rotate about axles 182a and 182b, respectively, and are interconnected by bracket 183. A plurality of barbs or needles 185 is disposed at substantially regular intervals around the circumference of conveyor 180.

Flexible tube 177 preferably includes a plurality of through-wall slots 186 to enhance flexibility of the tube, yet maintain torqueability. Preferably, flexible tube 177 is made from stainless steel with an etched or laser-cut slot pattern. Preferably, the slot pattern is a sinusoidal repeating pattern of slots perpendicular to the longitudinal axis of the tube. Additional and/or alternative patterns will be apparent to those of skill in the art.

Figure 18B:
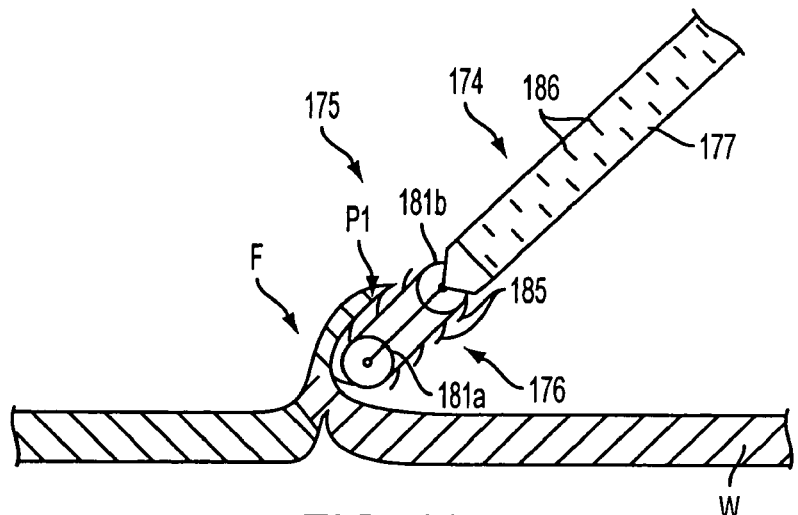
Figure 19:
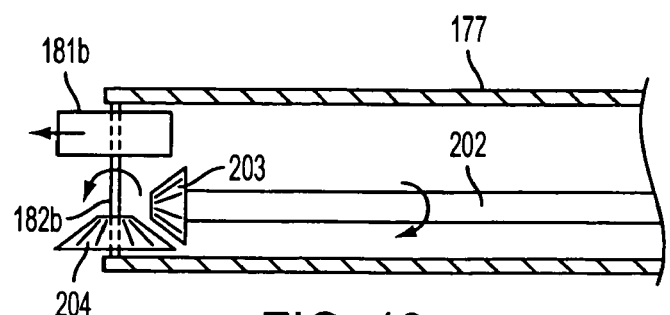
FIG. 19 is a cross-sectional view of the apparatus of FIGS. 18A-18D.

Referring to FIGS. 18 and 19, transmission of motive force to treadmill assembly 176 is described. In particular, drive shaft 202 disposed within flexible tube 177 is coupled to a manual knob or motor located at the proximal end of the catheter. The distal tip of drive shaft 202 is provided with beveled gear 203 that meshes with beveled gear 204 provided on axle 182b. Accordingly, rotation of beveled gear 203 is transmitted to beveled gear 204, thereby causing axle 182b to rotate. Axle 182b in turn rotates hub 181b, actuating conveyor 180. Reversing the rotation of drive shaft 202 reverses the direction of conveyor 180.

Referring again to FIGS. 18A-18D, a method of forming a gastrointestinal tissue fold F using apparatus 175 is described. In FIG. 18A, flexible tube 177 is positioned transesophageally so that treadmill assembly 176 contacts tissue wall W.

Preferably, contact should be made at an angle relative to the tissue wall W. For example, an angle of approximately 45 degrees is depicted in FIG. 8A, while many other angles may be used without departing from the scope of the present invention.

When treadmill assembly 176 contacts tissue wall W, needle 185 engages the tissue at contact point P1 as the needle moves around distal hub 181*a*. As depicted in FIG. 18B, as the needle moves away from distal hub 181*a*, tissue wall W is pulled towards proximal end 181*b*, thereby forming a small tissue fold F. As the treadmill assembly continues to turn, subsequent needles 185 engage the tissue wall so that it becomes securely engaged to treadmill assembly 176 along the length of conveyor 180.

Figure 18C:
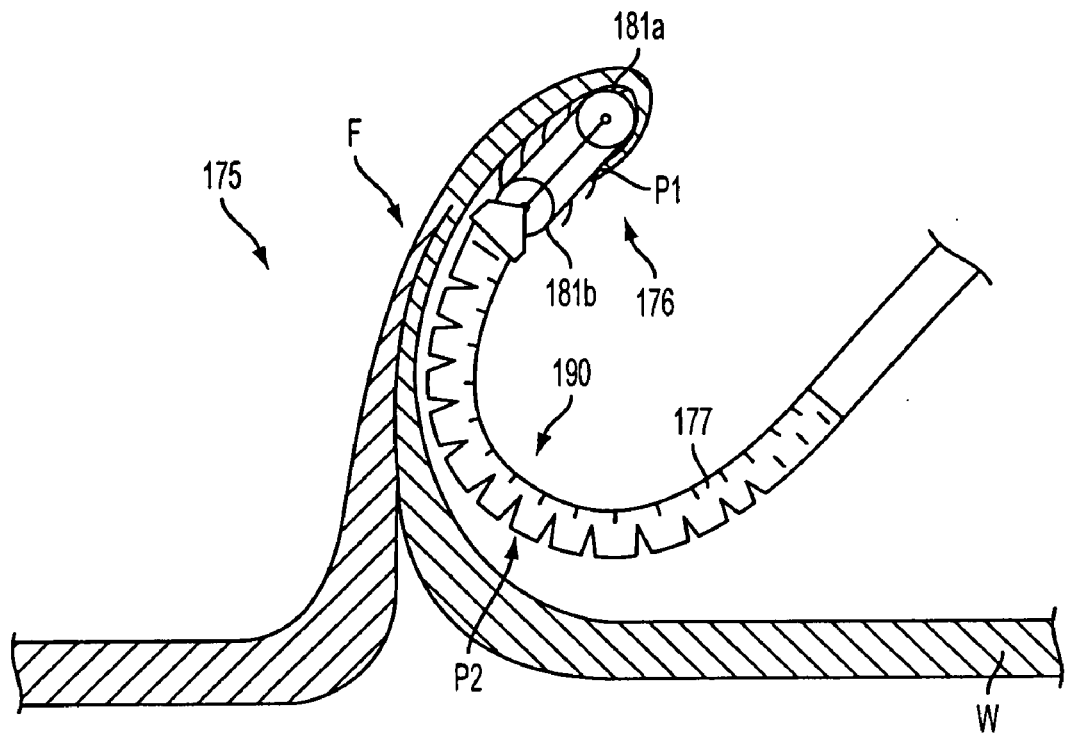

As depicted in FIG. 18C, once tissue wall W is securely engaged to treadmill assembly 176, distal end 174 of flexible tube 177 may be articulated in bendable section 190, thereby moving treadmill assembly 176 away from tissue wall W. The articulation of flexible tube 177 may be accomplished using a control wire and actuator disposed at the proximal end of the catheter, as previously described with respect to the embodiment of FIG. 1. By moving the treadmill assembly away from tissue wall W, additional tissue is pulled proximally and tissue fold F becomes elongated.

Figure 18D:
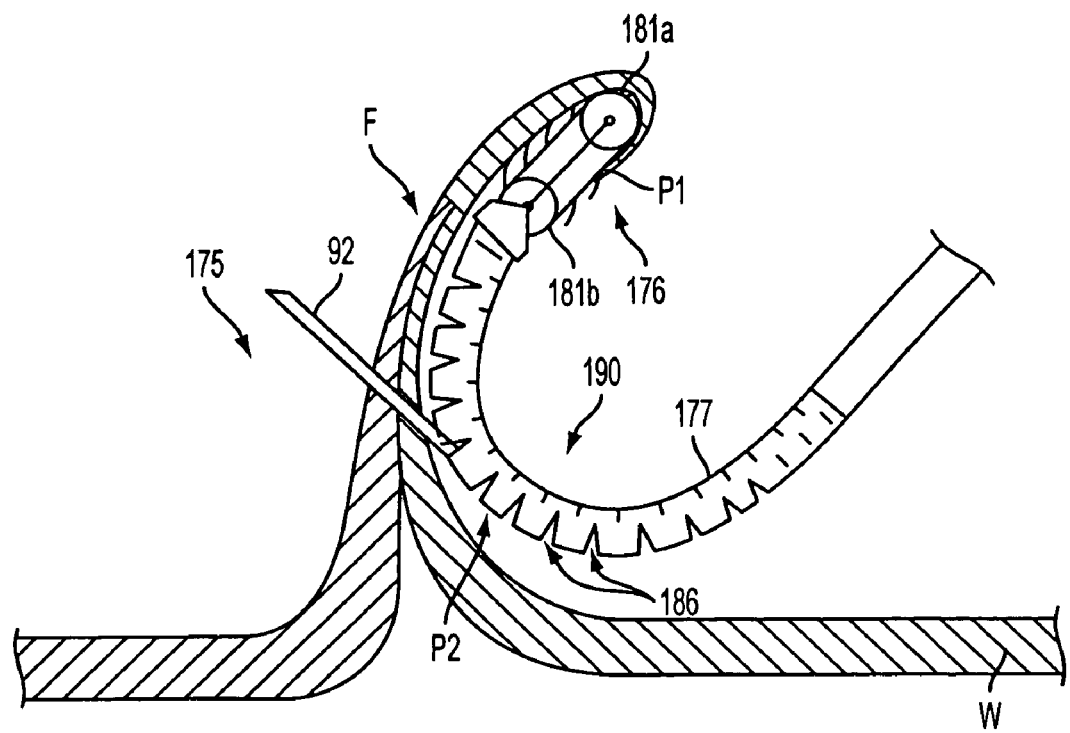

In FIG. 18D, tissue fold F is stretched across bendable section 190 of flexible tube 177 to create contact point P2. This permits a sharpened needle or obturator to be extended through one of slots 186 of bendable section 190 and across all four layers of the tissue wall W. Advantageously, stretching of tissue fold F across bendable section 190 permits an anchor to be ejected through both the muscularis and serosa layers, thus providing a durable foundation for gastrointestinal tissue approximation. For example, needle 192 may be extended through slot 186 in bendable section 190, and through the base of tissue fold F, and an anchor assembly (such as described with respect to any of FIGS. 4-17) may be ejected from needle 192 to secure the fold. Alternatively, an obturator (such as described with respect to FIGS. 5A and 5B) may be used to pierce the tissue fold at contact point P2 and deliver the anchor assembly. Treadmill assembly 176 may be disengaged from tissue wall W by reversing the rotation of proximal hub 181*b*.

Figure 20A:
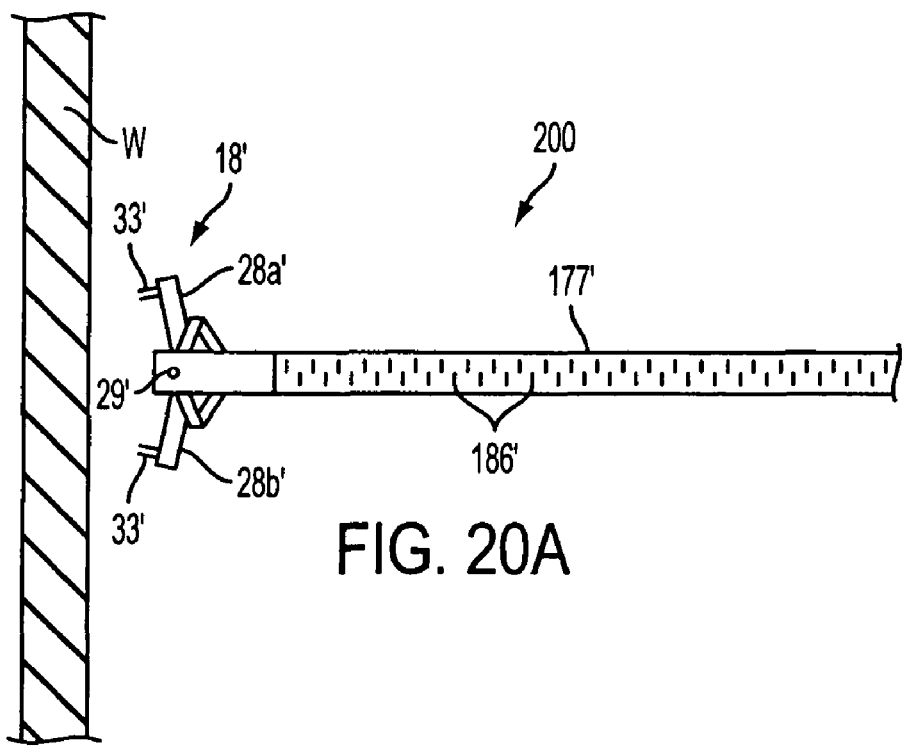
FIGS. 20A-20D are side views of further alternative apparatus for forming a gastrointestinal tissue fold in accordance with the principles of the present invention.

Referring now to FIG. 20A, a further alternative embodiment of apparatus for forming a tissue fold in accordance with the principles of the present invention is described. Apparatus 200 comprises tissue grabbing assembly 18' coupled to the distal end of a flexible tube 177', such as described with respect to the embodiment of FIG. 18. Flexible tube 177' preferably includes a plurality of through-wall slots 186' to enhance flexibility of the tube, yet maintain torqueability. In addition, flexible tube 177' may be made from stainless steel with an etched or laser-cut slot pattern, such as a sinusoidal repeating pattern of slots perpendicular to the longitudinal axis of the tube. Alternative flexible patterns will be apparent.

Tissue grabbing assembly 18' is similar to that described with respect to the embodiment of FIG. 1, and comprises a pair of jaws 28*a*', 28*b*' arranged to rotate about pivot point 29' between an open configuration and a closed configuration. Each of jaws 28*a*', 28*b*' preferably includes sharpened teeth 33' disposed near its distal end to facilitate grasping tissue wall W.

Figure 20B:
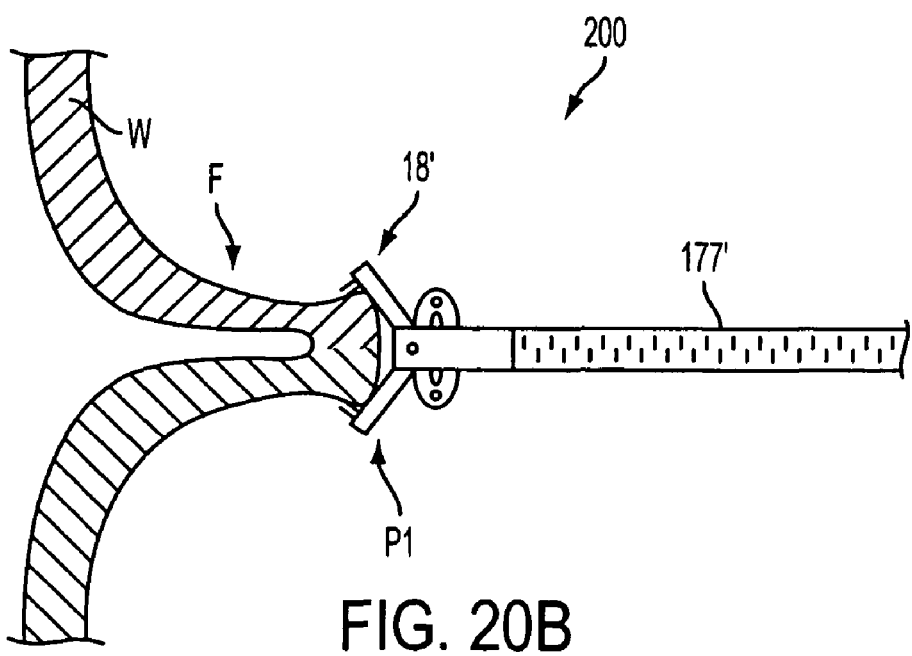

With respect to FIG. 20A, tissue grabbing assembly 18' is positioned transesophageally adjacent to tissue wall W and jaws 28*a*', 28*b*' are moved to the open position. Tissue grabbing assembly 18' then is moved into contact with tissue wall W. As depicted in FIG. 20B, tissue grabbing assembly 18' is used to grab the tissue wall at a first contact point P1. After capturing a portion of tissue wall W within jaws 28*a*', 28*b*', flexible tube 177' is urged proximally to stretch tissue wall W and create tissue fold F.

Figure 20C:
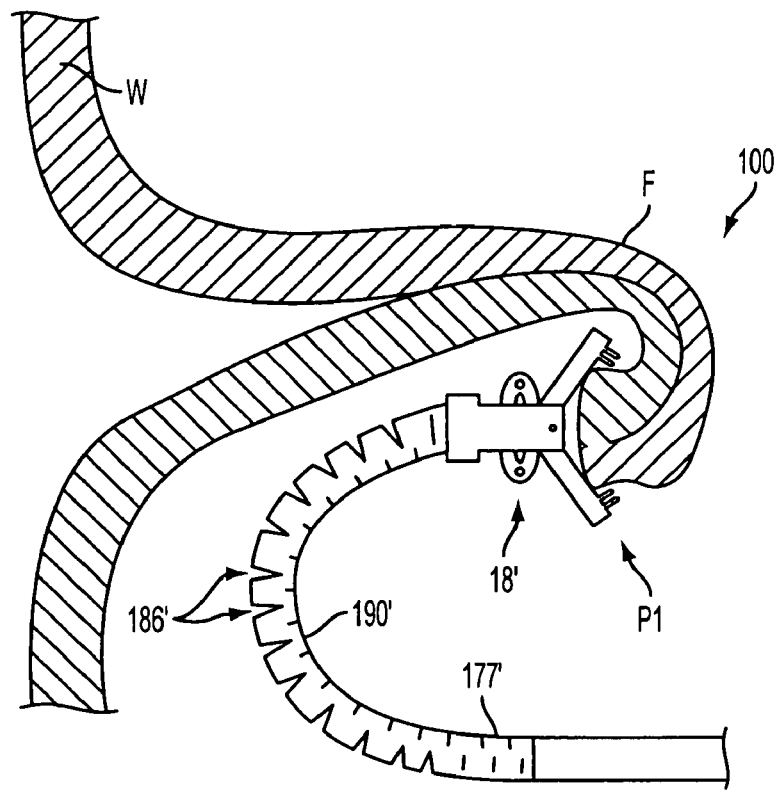

Referring to FIG. 20C, once tissue fold F is formed, the distal end of flexible tube 177' is articulated about bendable section 190' to move tissue grabbing assembly 18' away from tissue wall W. Articulation of flexible tube 177' may be controlled using an actuator disposed at the proximal end of the catheter, thus causing tissue fold F to become elongated.

Figure 20D:
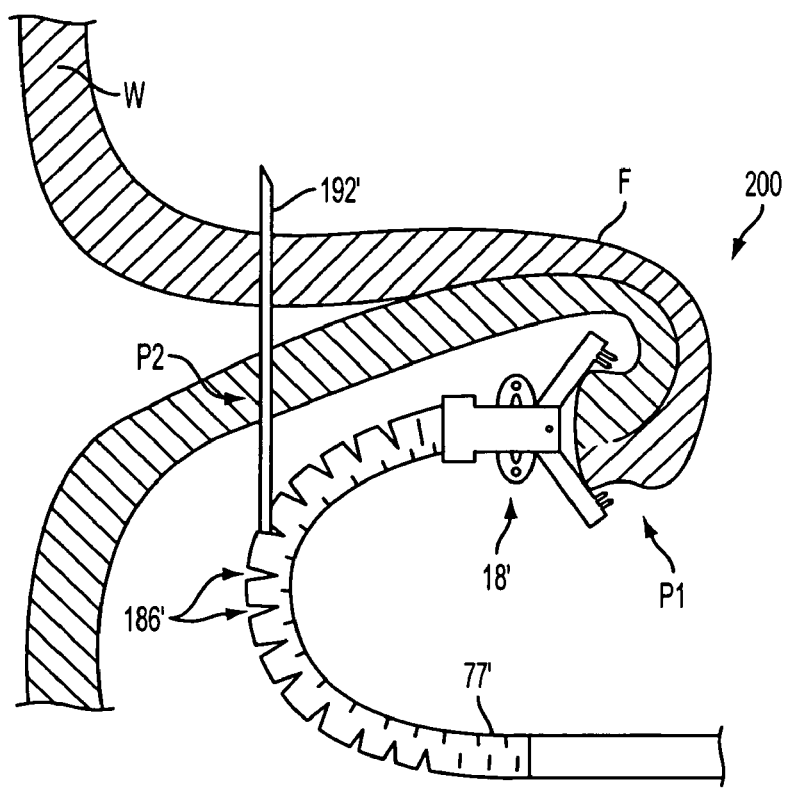

In FIG. 20D, tissue fold F is shown stretched across bendable section 190' so that a sharpened needle or obturator may be extended from one of slots 186' in bendable section 190' and across all four layers of the tissue wall W. Needle 192' then may be extended from slot 186' in bendable section 190' through contact point P2 and tissue fold F. An anchor assembly (e.g., as described with respect to any of FIGS. 4-17) then may be ejected from needle 192' to secure the fold. Alternatively, an obturator (e.g., as described with respect to FIGS. 5A and 5B) may be used to pierce the tissue fold at contact point P2 and deliver the anchor assembly.

With reference now to FIG. 21, an anchor delivery system adapted for use with the adjustable anchor assemblies of FIGS. 7-17 is described. In FIG. 21, the anchor delivery system is illustratively shown in use with anchor assembly 60 of FIG. 7, but this should in no way be construed as limiting. Also, the delivery system of FIG. 21 may be used in conjunction with apparatus for forming a tissue fold, such as apparatus 10, 175 and 200 described previously, or alternative apparatus described hereinafter, in order to anchor the tissue fold. Alternatively, the delivery system may be used for any other application, or in conjunction with any other apparatus, requiring delivery of an anchor assembly.

Figure 21A:
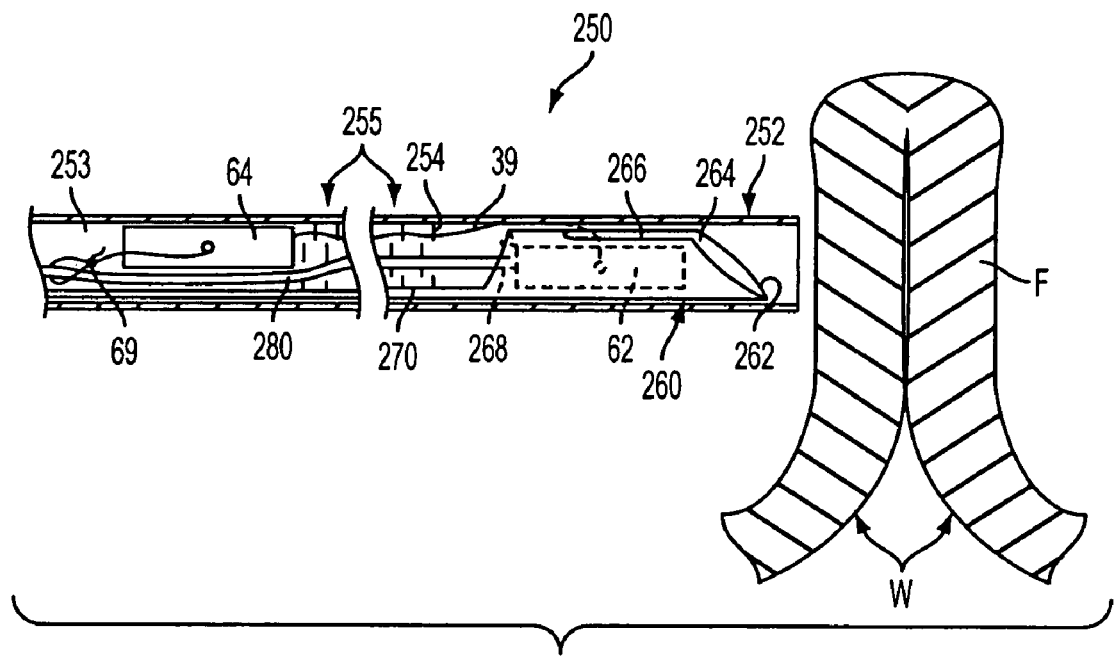
FIGS. 21A-21G are schematic side-sectional views of an anchor delivery system adapted for use with the adjustable anchor assemblies of FIGS. 7-17, illustrating a method of delivering the unidirectionally adjustable anchor assembly of FIG. 7 across a tissue fold.

In FIG. 21A, a distal region of anchor delivery system 250 is disposed adjacent tissue fold F in tissue wall W. Anchor delivery system 250 comprises flexible delivery tube 252 having lumen 253. Flexible delivery tube 252 may be configured for insertion through a patient's mouth and esophagus into a gastrointestinal lumen, such as the stomach. Lumen 253 of delivery tube 252 preferably has a diameter of less than about 5 mm, and even more preferably has a diameter of about 2-3 mm. Flexible delivery tube 252 preferably includes a plurality of through-wall slots 254 to enhance flexibility of the tube, yet maintain torqueability. Slots 254 may form bendable section 255. Preferably, flexible delivery tube 252 is made from stainless steel with an etched or laser-cut slot pattern. The slot pattern is preferably a sinusoidal repeating pattern of slots perpendicular to the longitudinal axis of the tube. Additional and/or alternative patterns will be apparent.

Anchor delivery system 250 further comprises delivery needle 260. Needle 260 preferably has a length of less than 2 cm, and even more preferably has a length of about 1.5 cm. Needle 260 preferably comprises sharpened distal tip 262, lumen 264, slot 266 extending proximally from distal tip 262, and proximal eyelet 268.

Lumen 264 of needle 260 is dimensioned such that a distal anchor may be disposed therein. As discussed previously, anchor delivery system 250 is illustratively described in conjunction with anchor assembly 60 of FIG. 7. In FIG. 21A, distal anchor 62 is disposed within lumen 264 of needle 260. Suture 39 passes through slot 266 of the needle as the suture extends from distal anchor 62 to proximal anchor 64. Needle 260 preferably is disposed within lumen 253 of flexible delivery tube 252 distal of bendable section 255, while proximal anchor 64 preferably is disposed within delivery tube 252 proximal of bendable section 255.

In this arrangement, distal anchor 62 may be deployed through needle 260 while the bendable section is actuated or bent, e.g., when anchor delivery system 250 is used in conjunction with previously described plication apparatus. Proximal anchor 64 subsequently may be advanced through bendable section 255 after the bendable section has once again been straightened. The distance, or length, of suture 39 extending between distal anchor 62, which is disposed distal of the bendable section, and proximal anchor 64, which is disposed proximal of the bendable section, is preferably greater than or equal to about 2 cm, and is even more preferably greater than or equal to about 4 cm.

Needle 260 is proximally coupled to needle pushrod 270, which facilitates translation of the needle beyond a distal end of flexible delivery tube 252. Needle pushrod 270 extends to a control actuator disposed at a proximal end of anchor delivery system 250 (not shown). Pushrod 270 optionally may be spring-loaded (not shown), for example, to facilitate puncture of tissue wall W and passage of needle 260 through tissue fold F.

Anchor delivery system 250 further comprises anchor pushrod 280, which is removably disposed through eyelet 268 of needle 260, and is configured to eject distal anchor 62 from lumen 264 of needle 260. As with needle pushrod 270, anchor pushrod 280 extends to a control actuator disposed at a proximal end of anchor delivery system 250 (not shown). The actuators controlling pushrods 270 and 280 are preferably at least partially coupled so that relative motion between the two pushrods can be limited and/or eliminated, as needed. Pushrod 280 passes through the proximal loop of suture formed by knot 69 on suture 39, such that the suture loop is threaded between needle pushrod 270 and anchor pushrod 280. This facilitates unidirectional adjustment of the length of suture disposed between distal anchor 62 and proximal anchor 64, as described hereinbelow.

Figure 21B:
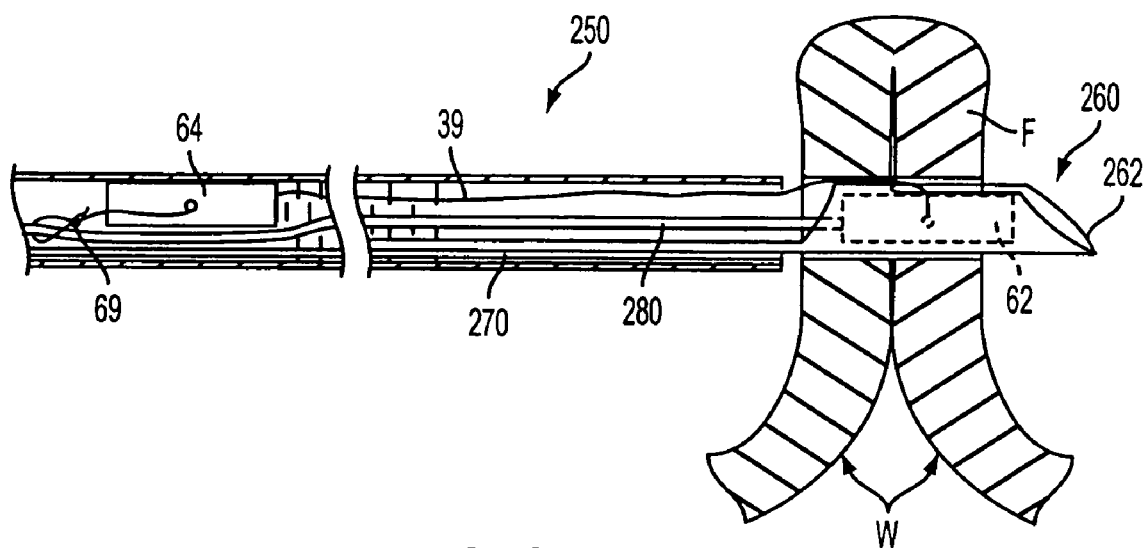
Figure 21C:
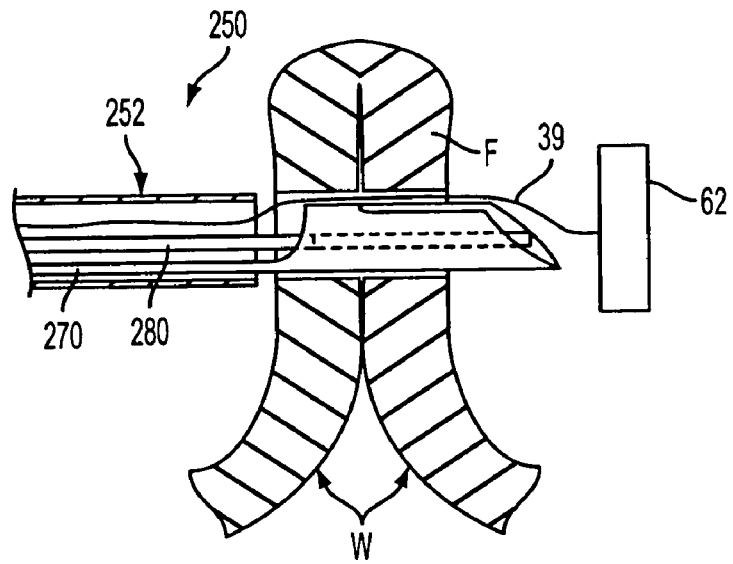

In FIG. 21B, pushrods 270 and 280 are simultaneously distally advanced with sufficient force, e.g., via spring-loading, such that sharpened distal tip 262 of needle 260 pierces tissue wall W and is advanced across fold F. Bendable section 255 of flexible delivery tube 252 optionally may be bent during advancement of the needle, as described previously with respect to the plication apparatus (see FIG. 3E). Anchor pushrod 280 is then advanced distally with respect to needle pushrod 270 and needle 260, such that it abuts distal anchor 62 and ejects the anchor from lumen 264 of needle 260 on the distal side of tissue fold F, as seen in FIG. 21C. Suture 39 likewise is ejected from slot 266 and disposed across fold F.

During delivery, the longitudinal axis of distal anchor 62 is substantially parallel to the longitudinal axis of needle 260. However, once anchor 62 has been ejected from needle 260, suture tension induces the anchor to rotate approximately 90° about its longitudinal axis, so that its longitudinal axis is substantially perpendicular to the longitudinal axis of needle 260. This rotation of distal anchor 62 prevents it from being pulled back through tissue wall W. One or both ends of anchor 62 may be flared outward (not shown) to facilitate such rotation upon contact with the tissue wall.

Figure 21D:
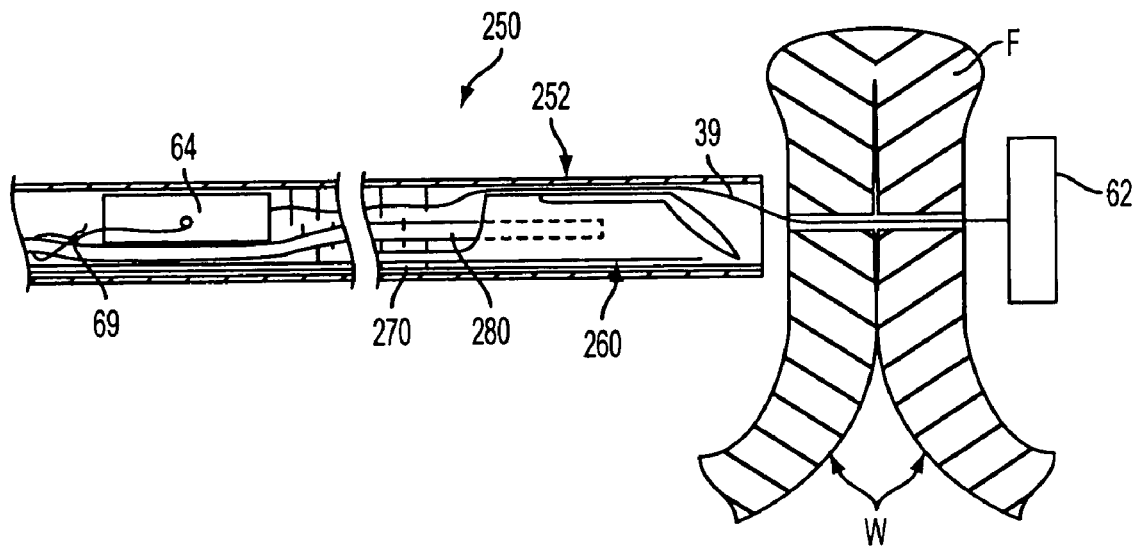

In FIG. 21D, anchor pushrod 280 is retracted proximally within lumen 264 of needle 260, the needle is retracted within flexibly delivery tube 252 via pushrod 270, and then delivery system 250 is retracted proximally across tissue fold F. Distal anchor 62 is disposed on the distal side of the tissue fold, suture 39 extends through the fold, and proximal anchor 64 is disposed on the proximal side of the fold within delivery tube 252. If bendable section 255 were flexed during deployment of distal anchor 62 (see FIG. 3E), it is straightened to facilitate delivery of the proximal anchor.

Figure 21E:
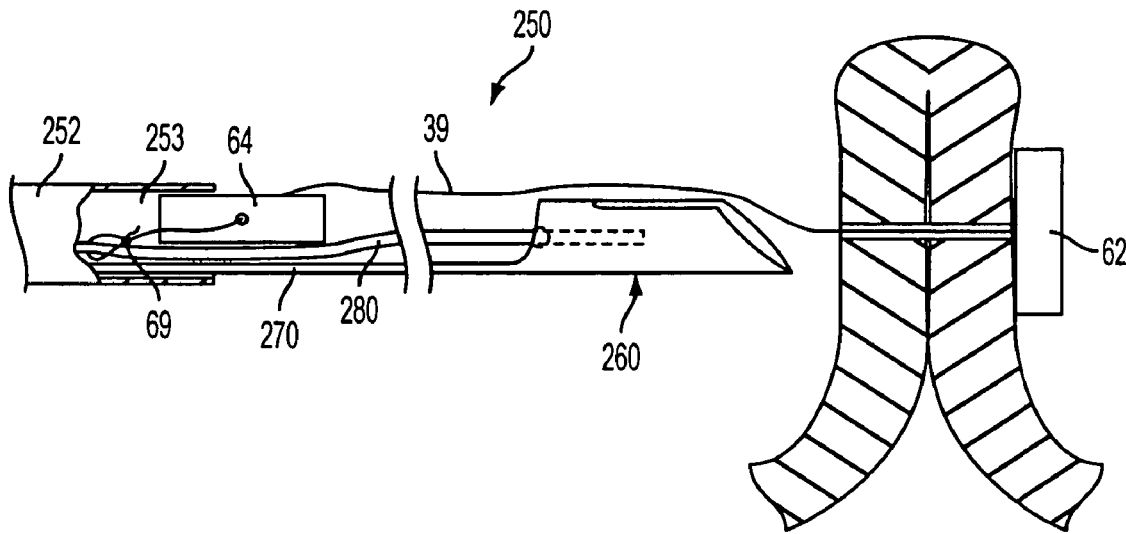

Delivery tube 252 is then retracted proximally with respect to pushrods 270 and 280, causing needle 260 to exit lumen 253 of the delivery tube on the proximal side of tissue fold F, thereby providing space for proximal anchor 64 to exit the lumen. Next, delivery tube 252 or the full delivery system 250 is retracted, such that proximal anchor 64 is ejected from delivery tube lumen 253, as seen in FIG. 21E. Delivery tube 252 is then re-advanced and/or pushrods 270 and 280 are simultaneously retracted, such that needle 260 is repositioned within lumen 253 of the delivery tube.

Figure 21F:
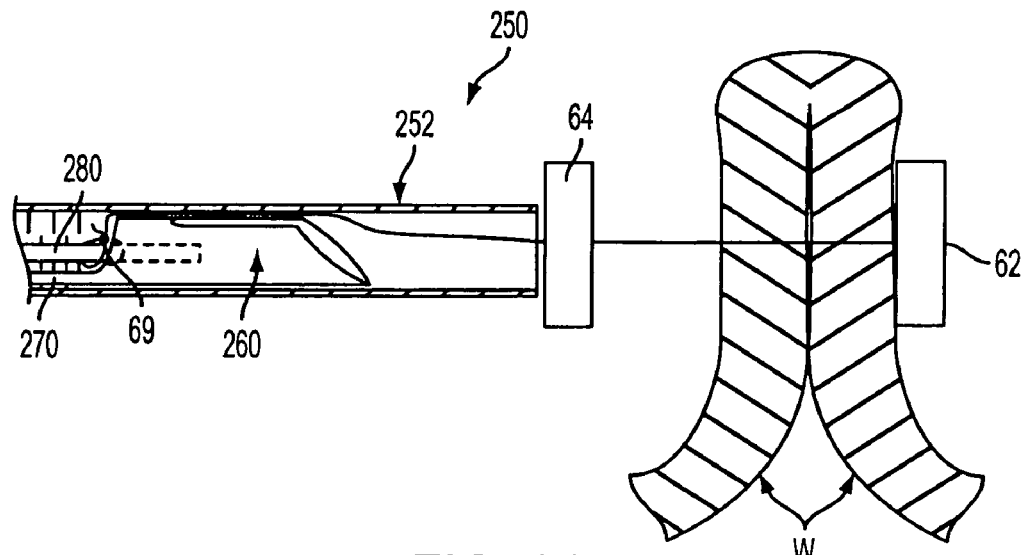

Flexible delivery tube 252 is advanced with respect to needle 260, such that it pushes proximal anchor 64 distally. The proximal suture loop formed by knot 69 on suture 39 catches against the proximal end of needle 260 and anchor pushrod 280, which pulls distal anchor 62 taut against tissue fold F, as seen in FIG. 21F. Continued advancement of delivery tube 252 unidirectionally adjusts, i.e. shortens, length L of suture 39 disposed between distal anchor 62 and proximal anchor 64, while forcing proximal anchor 64 against the tissue fold and firmly anchoring the fold between the proximal and distal anchors.

Figure 21G:
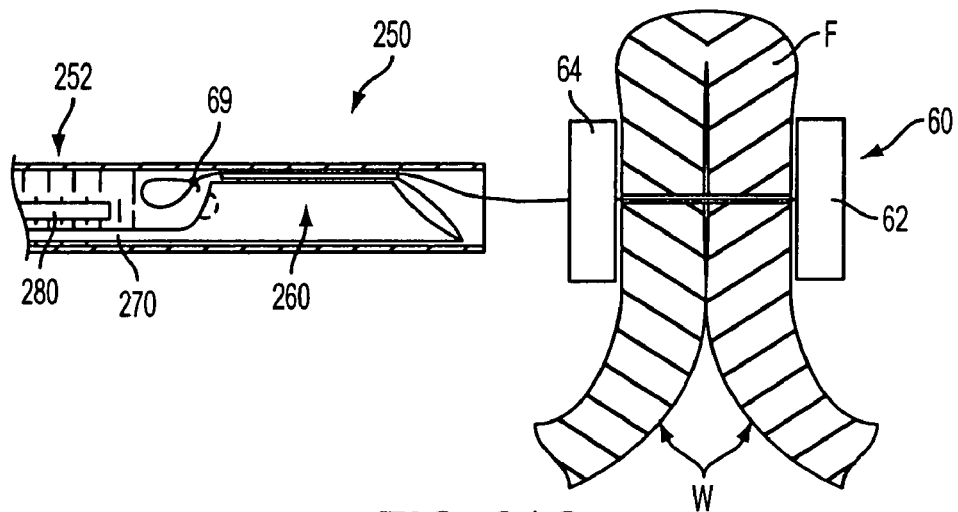

Once length L has been adjusted such that anchor assembly 60 firmly anchors tissue fold F in position, anchor pushrod 280 may be retracted proximally with respect to needle pushrod 270 and needle 260, such that the distal end of anchor pushrod 280 is proximally retracted through eyelet 268 and out of needle 260. As seen in FIG. 21G, the suture loop formed by knot 69 on suture 39 slips off the distal end of anchor pushrod 280, removing anchor assembly 60 from anchor delivery system 250. Anchor delivery system 250 may then be removed from the patient. Alternatively, needle 260, needle pushrod 270 and anchor pushrod 280 may be proximally retracted and removed from lumen 253 of anchor delivery tube 252. An additional anchor assembly 60 may then be reloaded within needle 260 and delivery tube 252 from a proximal end of the delivery tube, while a distal end of the delivery tube remains within the patient. The additional anchor assembly may, for example, be placed across an additional tissue fold.

Delivery system 250 optionally may comprise cutting apparatus (not shown) for removing the portion of suture extending proximally of proximal anchor 64 post-adjustment. Alternatively, secondary apparatus may be provided to remove such proximal length of suture. As yet another alternative, the unneeded length of suture may be left within the patient post-procedure.

In order to decrease the number of steps required to deliver and adjust anchor assembly 60, once distal anchor 62 has been deployed, as in FIG. 21C, the entire anchor delivery system 250 may be retracted proximally, such that needle 260 is retracted across tissue fold F while still disposed outside of delivery tube lumen 253. This is in contrast to the method described with respect to FIG. 21D, wherein the needle is disposed within the delivery tube prior to retraction across the tissue fold. Continued proximal retraction of anchor delivery system 250 or delivery tube 252 deploys proximal anchor 64 from delivery tube lumen 253. Anchor assembly 60 then may be unidirectionally adjusted, as described previously.

Anchor delivery system 250 advantageously provides a medical practitioner with significant control during all steps of anchor assembly deployment. Such control affords the medical practitioner ample opportunity to abort deployment of the anchor assembly. Upon passage of needle 260 across tissue fold F, as seen in FIG. 21B, the medical practitioner may decide to retract the needle across the fold and not launch the distal anchor. Alternatively, after deployment of the distal anchor 62, as seen in FIG. 21D, the medical practitioner may decide not to deploy the proximal anchor and may sever the suture connecting the proximal and distal anchors. The distal anchor then would simply pass harmlessly through the patient's digestive system. As yet another example, the medical practitioner may decide not to cinch the proximal and distal anchors post-deployment, thereby leaving the anchors in place without securing tissue fold F. Furtherstill, the medical practitioner may reverse cinching or cut the anchor assembly post-deployment, thereby reversing tissue fold formation.

As will be apparent to those of skill in the art, when anchor delivery system 250 is used in conjunction with previously described apparatus 10, 175 or 200, to place an anchor assembly across fold F formed by said apparatus, flexible delivery tube 252 may either comprise or be advanced through flexible tube 14, 177 or 177', of apparatus 10, 175 or 200, respectively. Likewise, needle 260 may comprise needle 34, 92 or 92', of apparatus 10, 175 or 200, respectively. Needle 260 alternatively may comprise obturator 50 of FIG. 5. As will be apparent, components of anchor delivery system 250 may also comprise or be advanced through comparable components of alternative tissue folding apparatus described hereinafter.

Referring now to FIG. 22, an alternative anchor delivery system is described. As with anchor delivery system 250 of FIG. 21, anchor delivery system 300 of FIG. 22 is adapted for use with the adjustable anchor assemblies of FIGS. 7-17. In FIG. 22, the anchor delivery system 300 is illustratively shown in use with anchor assembly 60 of FIG. 7, but this should in no way be construed as limiting. Also, delivery system 300 may be used in conjunction with apparatus for forming a tissue fold, such as apparatus 10, 175 and 200 described previously, or alternative apparatus described hereinafter, in order to anchor the tissue fold. Alternatively, the delivery system may be used for any other application, or in conjunction with any other apparatus, requiring delivery of an anchor assembly.

Figure 22A:
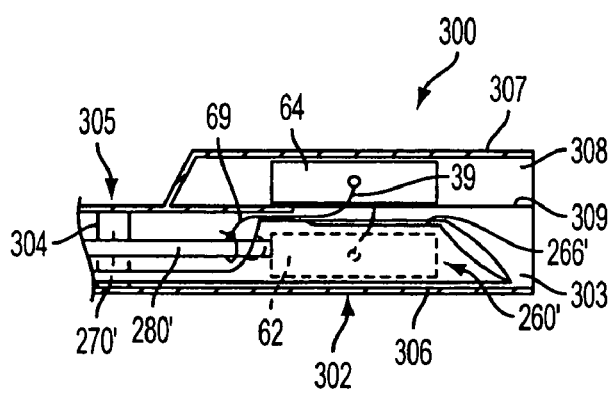
FIGS. 22A and 22B are, respectively, a schematic side-view, partially in section, and an end-view of an alternative anchor delivery system adapted for use with the adjustable anchor assemblies of FIGS. 7-17, wherein the proximal anchor is disposed within a separate delivery tube.

FIG. 22A illustrates a distal region of anchor delivery system 300. System 300 comprises flexible delivery tube 302 having lumen 303. Flexible delivery tube 302 may be configured for insertion through a patient's mouth and esophagus into a gastrointestinal lumen, such as the stomach. Flexible delivery tube 302 preferably includes a plurality of through-wall slots 304 to enhance flexibility of the tube, yet maintain torqueability. Slots 304 may form bendable section 305. Preferably, flexible delivery tube 302 is made from stainless steel with an etched or laser-cut slot pattern. The slot pattern is preferably a sinusoidal repeating pattern of slots perpendicular to the longitudinal axis of the tube. Additional/alternative patterns will be apparent to those of skill in the art.

Figure 22B:
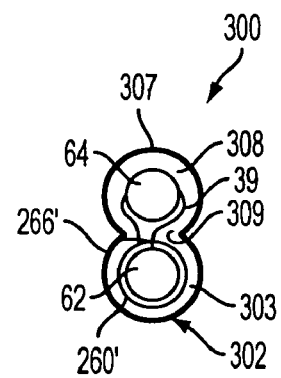

Flexible delivery tube 302 further comprises end region 306, which is coupled to anchor tube 307 having lumen or bore 308. As best seen in FIG. 22B, lumen 308 of anchor tube 307 communicates with lumen 303 of delivery tube 302 via through-slot 309. Proximal anchor 64 is disposed within anchor tube 307, while distal anchor 62 is disposed within needle 260', which sits within delivery tube 302.

Suture 39 passes out of needle 260' from distal anchor 62 through slot 266'. It then crosses from flexible delivery tube 302 to anchor tube 307 via through-slot 309. After passing through proximal anchor 64, suture 39 is passed back to delivery tube 302 via the through-slot, and is threaded around anchor pushrod 280', such that the loop of suture formed by knot 69 on suture 39 is disposed between needle pushrod 270' and anchor pushrod 280'.

Needle 260', needle pushrod 270' and anchor pushrod 280' are substantially the same as needle 260 and pushrods 270 and 280, respectively, which are described hereinabove with respect to anchor delivery system 250 of FIG. 21. Furthermore, anchor assembly 60 may be delivered from and adjusted by anchor delivery system 300 in a manner similar to that described hereinabove with respect to system 250.

In FIG. 22A, anchor tube 307 of anchor delivery system 300 is illustratively shown as a relatively short tube having lumen or bore 308 adapted for disposal of proximal anchor 64 therein. However, it should be understood that anchor tube 307, lumen 308 and/or through-slot 309 alternatively may extend all or part of the way to a proximal end of flexible delivery tube 302 of delivery system 300. Advantageously, such an arrangement facilitates loading of anchor assembly 60 from a proximal end of the anchor delivery system, e.g., for reloading of anchor delivery system 300 while a distal region of the system is disposed within a patient. Such an arrangement also may simplify manufacturing of the system.

Anchor delivery system 300 illustratively has been described with a single anchor assembly 60 disposed therein. However, it should be understood that a plurality of anchor assemblies may be loaded within delivery system 300, thereby facilitating delivery of multiple anchor assemblies across different points of a tissue fold, across different (e.g., adjacent) tissue folds, or across other tissue structures. The plurality of distal anchors 62 preferably are loaded within needle 262' of flexible delivery tube 302, while the plurality of proximal anchors 64 preferably are loaded within lumen 308 of anchor tube 307.

An advantage of anchor delivery system 300, as compared to system 250 of FIG. 21, is that both the proximal and distal anchors are located distal of the bendable section of the delivery tube during delivery. This reduces an initial length of suture that must be disposed between the anchors, thereby reducing a length of unneeded suture extending proximally of the proximal anchor post-delivery and adjustment. It also simplifies delivery by allowing both the proximal and distal anchors to be delivered while the bendable section of the delivery tube is bent. Additionally, placement of the proximal anchor in a separate anchor tube eliminates a need to eject the needle from the flexible delivery tube on the proximal side of a tissue fold in order to deploy the proximal anchor, thereby reducing a risk of accidental tissue puncture with the needle.

Figure 23:
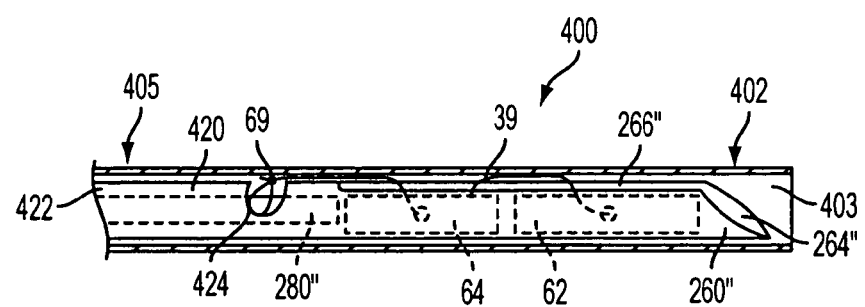
FIG. 23 is a schematic side-sectional view of an alternative anchor delivery system adapted for use with the adjustable anchor assemblies of FIGS. 7-17, wherein both the proximal and distal anchors are loaded within the needle.

With reference to FIG. 23, another alternative anchor delivery system is described. As with anchor delivery systems 250 and 300 of FIGS. 21 and 22, respectively, anchor delivery system 400 of FIG. 23 is adapted for use with the adjustable anchor assemblies of FIGS. 7-17. Anchor delivery system 400 is illustratively shown in use with anchor assembly 60 of FIG. 7, but this should in no way be construed as limiting. Also, delivery system 400 may be used in conjunction with apparatus for forming a tissue fold, such as apparatus 10, 175 and 200 described previously, or alternative apparatus described hereinafter, in order to anchor the tissue fold. Alternatively, delivery system 400 may be used for any other application, or in conjunction with any other apparatus, requiring delivery of an anchor assembly.

FIG. 23 illustrates a distal region of anchor delivery system 400. System 400 comprises flexible delivery tube 402 having lumen 403. Flexible delivery tube 402 may be configured for insertion through a patient's mouth and esophagus into a gastrointestinal lumen, such as the stomach. Flexible delivery tube 402 preferably includes a plurality of through-wall slots to enhance flexibility of the tube, yet maintain torqueability. The slots may form bendable section 405.

Anchor delivery system 400 further comprises delivery needle 260", which is disposed within lumen 403 of flexible delivery tube 402 distal of bendable section 405 during delivery. As discussed previously, anchor delivery system 400 is illustratively described in conjunction with anchor assembly 60 of FIG. 7. Needle 260" preferably has a length sufficient for both distal anchor 62 and proximal anchor 64 of anchor assembly 60 to be disposed therein; for example, needle 260" preferably has a length of less than about 5 cm, and even more preferably has a length of about 3 cm. Except for an increase in length, needle 260" is substantially the same as needle 260 of FIG. 21.

In FIG. 23, both distal anchor 62 and proximal anchor 64 are disposed within lumen 264" of needle 260". Suture 39 passes through and back through slot 266" of the needle as the suture extends from distal anchor 62 to proximal anchor 64. Alternatively the length of suture between the proximal and distal anchors may be disposed within the needle during delivery. Advantageously, both the proximal and distal anchors of anchor assembly 60 may be deployed through needle 260" while bendable section 405 is actuated or bent, e.g., while anchor delivery system 400 is used in conjunction with previously described plication apparatus.

Needle 260" is proximally coupled to flexible needle pushtube 420, which facilitates translation of the needle beyond a distal end of flexible delivery tube 402. As will be apparent to those of skill in the art, needle 260" and needle pushtube 420 optionally may be manufactured as a single piece. Needle pushtube 420 comprises lumen 422, as well as skive 424 that communicates with lumen 422. Needle pushtube 420 extends to a control actuator (not shown), which may be spring-loaded, disposed at a proximal end of anchor delivery system 400.

Anchor pushrod 280", which is substantially the same as anchor pushrod 280 described previously, is removably disposed within lumen 422 of needle pushtube 420 distal of skive 424. As with pushtube 420, anchor pushrod 280" extends to a control actuator (not shown) disposed at a proximal end of the anchor delivery system. Suture 39 proximally extends from proximal anchor 64 through slot 266" of needle 260", through skive 424 and within lumen 422 of needle pushtube 420, around anchor pushrod 280" and out through skive 424 to knot 69. The proximal loop of suture formed by knot 69 is trapped around pushrod 280" and within lumen 422 of the needle pushtube, thereby facilitating unidirectional adjustment of the length of suture disposed between distal anchor 62 and proximal anchor 64. As an alternative to the proximal loop of suture, knot 69 may be formed on the proximal end of suture 39, such that the knot is trapped between anchor pushtube 280" and needle pushrod 420 (see knot K of FIG. 24).

Anchor assembly 60 may be delivered, deployed and adjusted by anchor delivery system 400 in a manner similar to that described hereinabove with respect to system 250 of FIG. 21, with a few alterations. Specifically, during deployment of distal anchor 62, anchor pushrod 280" is advanced against proximal anchor 64, which in turn advances in-line distal anchor 62. The pushrod is advanced a sufficient distance with respect to needle 260" to eject the distal anchor from needle lumen 264", but not so far as to also prematurely eject proximal anchor 64. Motion limitation apparatus may be provided to ensure that the distal anchor is not prematurely ejected. Exemplary motion limitation apparatus is described hereinbelow with respect to FIG. 24; additional apparatus, per se known, will be apparent.

In order to eject proximal anchor 64 from lumen 264" of needle 260", either the needle is retracted until length L of suture 39 disposed between the proximal and distal anchors is pulled taut and pulls the proximal anchor out of the needle lumen, or anchor pushrod 280" is advanced a sufficient distance within the lumen of needle 260" to eject the proximal anchor from the lumen (or a combination thereof). Additionally, in order to release anchor assembly 60 from anchor delivery system 400 post-delivery and adjustment, anchor pushrod 280" is retracted proximal of skive 424 such that the loop of suture 39 formed by knot 69 is no longer trapped within lumen 422 of needle pushrod 420. Upon deployment of anchor assembly 60, delivery system 400 may be removed from the patient. Alternatively, needle 260" and needle pushrod 420, as well as anchor pushrod 280", may be removed from the patient, reloaded with a new anchor assembly, and re-advanced through flexible delivery tube 402 for deployment of additional anchors without necessitating removal of delivery tube 402 from the patient.

A significant advantage of anchor delivery system 400, as compared to system 250 of FIG. 21, is that both the proximal and distal anchors are disposed distal of bendable section 405 of flexible delivery tube 402. A significant advantage of anchor delivery system 400, as compared to system 300 of FIG. 22, is that both the proximal and distal anchors are disposed within needle 260", thereby eliminating a need for an anchor tube and reducing a profile of the system.

Figure 24:
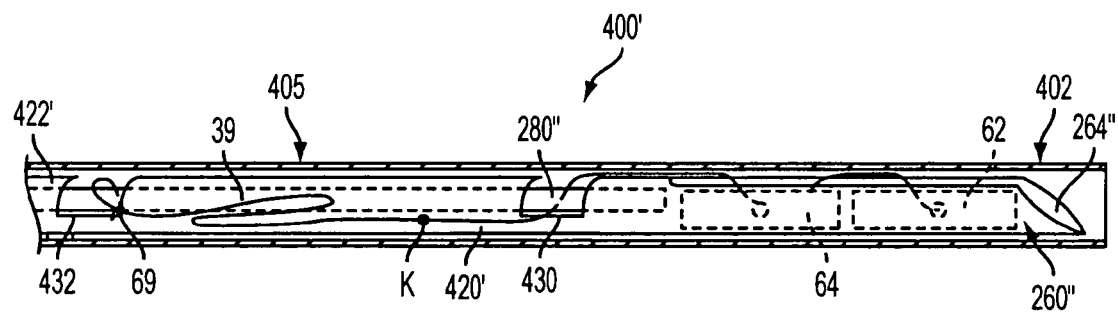
FIG. 24 is a schematic side-sectional view of an alternative embodiment of the anchor delivery system of FIG. 23 comprising motion limitation apparatus.

Referring now to FIG. 24, an alternative embodiment of anchor delivery system 400 is described comprising motion limitation apparatus. Anchor delivery system 400' is substantially the same as system 400, except that needle pushtube 420' comprises two skives: motion limitation skive 430 and unidirectional adjustment skive 432, both of which communicate with lumen 422' of the needle pushrod. Suture 39 proximally extends from proximal anchor 64, through motion limitation skive 430 and within lumen 422' between anchor pushrod 280" and needle pushtube 420'. Suture 39 exits skive 430 and is tied off at motion limitation knot K, which is trapped at skive 430 by anchor pushrod 280". Suture 39 then continues proximally to unidirectional adjustment skive 432 and the proximal loop of suture formed by knot 69, which is trapped at skive 432 around pushrod 280".

A length of suture extending between proximal anchor 64 and knot K is specified such that distal anchor 62 may exit lumen 264" of needle 260", but proximal anchor 64 cannot exit while knot K is trapped at skive 430 by anchor pushrod 280". For example, during delivery of anchor assembly 60 across a tissue fold, advancement of pushrod 280" advances proximal anchor 64, which in turn advances in-line distal anchor 62 until the distal anchor is ejected from needle lumen 264" on the distal side of the tissue fold. Knot K limits a distance anchor pushrod 280" may be advanced and ensures that proximal anchor 64 is not prematurely deployed.

Once anchor delivery system 400' is again disposed on the proximal side of the tissue fold, anchor pushrod 280" is retracted proximal of motion limitation skive 430, thereby allowing knot K to escape from skive 430 and facilitating deployment of proximal anchor 64. Proximal anchor 64 may be deployed by either retracting needle 260" until the length of suture between the two anchors is pulled taut and pulls the proximal anchor out of the needle, or by re-advancing pushrod 280" to push the proximal anchor out of the needle.

The anchor assembly may then be unidirectionally adjusted via the suture loop trapped at skive 232, as described previously. After adjustment has been completed, anchor pushrod 280" is retracted proximal of unidirectional adjustment skive 432, thereby allowing the loop of suture formed by knot 69 of suture 39 to escape from skive 432. As with anchor delivery systems 250 and 400 described previously, upon deployment of the anchor assembly, system 400' may be removed from the patient, or may be reloaded while flexible tube 402 remains in the patient. A significant advantage of anchor delivery system 400', as compared to system 400 of FIG. 23, is that motion limitation skive 430 reduces a risk of premature deployment of proximal anchor 64.

With reference to FIG. 25, yet another alternative anchor delivery system is described. Anchor delivery system 500 is adapted to deliver multiple adjustable anchor assemblies without necessitating reloading or removal from a patient. Delivery system 500 may be used in conjunction with apparatus for forming a tissue fold or may be used for any other application, or in conjunction with any other apparatus, requiring delivery of an anchor assembly. In FIG. 25, anchor delivery system 500 is illustratively loaded with multiple anchor assemblies 60 of FIG. 7, but this should in no way be construed as limiting.

FIG. 25 illustrates a distal region of anchor delivery system 500. System 500 comprises flexible delivery tube 510, flexible needle tube 520, anchor pushrod 530 and skive rod 540. Delivery tube 510, which is substantially the same as delivery tube 402 described previously, comprises lumen 511 and optional bendable section 512. Needle tube 520 comprises delivery needle 522, anchor lumen 523 and skive bore 524. Lumen 523 extends through needle tube 520 from its proximal end to needle 522, and anchor pushrod 530, as well as anchor assemblies 60, is disposed within the lumen. Bore 524 preferably terminates just proximal of needle 522; skive rod 540 is disposed within the bore. For ease of manufacturing, bore 524 optionally may be replaced with a lumen (not shown) that extends all the way to needle 522.

Needle tube 520 further comprises two through-slots and two skives: first motion limitation through-slot 526a, first unidirectional adjustment skive 528a, second motion limitation through-slot 526b, and second unidirectional adjustment skive 528b. The skives and through-slots all communicate with skive bore 524. Through-slots 526 further communicate with anchor lumen 523 and provide passageways between the anchor lumen and skive bore 524. Skives 528 further communicate with the exterior of needle tube 520 and provide passageways between the exterior and skive bore 524.

As discussed previously, anchor delivery system 500 is illustratively shown loaded with anchor assemblies 60. First anchor assembly 60a and second anchor assembly 60b are disposed within anchor lumen 523, with assembly 60a disposed distal of assembly 60b. Anchor pushrod 530 is disposed proximal of second assembly 60b within lumen 523.

First suture 39a of first anchor assembly 60a proximally extends within lumen 523 from first distal anchor 62a to and through first proximal anchor 64a. Suture 39a then extends from anchor lumen 523 to skive bore 524 via first motion limitation through-slot 526a. Suture 39a loosely encircles skive rod 540 and is tied off to itself at first motion limitation knot $K_{1A}$, such that the loop of suture formed by knot $K_{1A}$ is trapped about skive rod 540. A length of suture disposed between first proximal anchor 64a and first motion limitation knot $K_{1A}$ is sufficient to allow deployment of first distal anchor 62a from lumen 523 of needle tube 520, but is not long enough to allow deployment of first proximal anchor 64a from the lumen. Rather, the length of suture is pulled taut with the loop formed by knot $K_{1A}$ abutting first through-slot 526a and trapped about skive rod 540. In this manner, the suture loop formed by knot $K_{1A}$ provides motion limitation when disposed about skive rod 540. Skive rod 540 may be translated relative to the suture loop to release the loop from the rod after deployment of first distal anchor 62a.

From knot $K_{1A}$, first suture 39a continues proximally to first unidirectional adjustment skive 528a. Suture 39a then once again loosely encircles skive rod 540 and is tied off to itself at first unidirectional adjustment knot $K_{1B}$. While disposed about skive rod 540 at first skive 528a, the loop of suture formed by knot $K_{1B}$ may be used to unidirectionally adjust first anchor assembly 60a post-deployment, as described hereinabove. A length of suture disposed between first proximal anchor 64a and first unidirectional adjustment knot $K_{1B}$ is sufficient to enable deployment of the anchor from lumen 523 of anchor tube 520.

Second suture 39b of second anchor assembly 60b couples second distal anchor 62b and second proximal anchor 64b to second motion limitation through-slot 526b and second unidirectional adjustment skive 528b in a manner similar to that described with respect to first suture 39a of first anchor assembly 60a. The loop of suture formed by second motion limitation knot $K_{2A}$ precludes premature deployment of second proximal anchor 64b, while the loop of suture formed by second unidirectional adjustment knot $K_{2B}$ enables adjustment of a length of suture disposed between second distal anchor 62b and second proximal anchor 64b.

Anchor assemblies 60a and 60b may be delivered from, and adjusted by, anchor delivery system 500 in a manner similar to that described hereinabove with respect to system 400' of FIG. 24, with a few alterations. Specifically, during deployment of first distal anchor 62a, anchor pushrod 530 is advanced against second proximal anchor 64b, which in turn advances in-line second distal anchor 62b and in-line first proximal anchor 64a. The pushrod is advanced a sufficient distance with respect to needle tube 520 to eject first distal anchor 62a from anchor lumen 523.

Additional advancement of pushrod 530 causes the suture loop formed by first motion limitation knot $K_{1A}$ to catch against first through-slot 526a, thereby ensuring that first proximal anchor 64a is not prematurely ejected from lumen 523. When ready to deploy the first proximal anchor, skive rod 540 may be retracted proximal of first motion limitation through-slot 526a, thereby freeing the loop of suture formed by knot $K_{1A}$ from the skive rod. First proximal anchor 64a may then be deployed by further distal advancement of the anchor pushrod against second anchor assembly 60b. The second anchor assembly advances first proximal anchor 64a out of needle 522.

First anchor assembly 60a then may be unidirectionally adjusted as described hereinabove, using first skive 528a, the loop of suture formed by first adjustment knot $K_{1B}$ and delivery tube 510. Once adjusted, skive rod 540 may be further retracted within skive bore 524 to a position proximal of first skive 528a, thereby releasing first anchor assembly 60a from anchor delivery system 500. Second anchor assembly 60b may then be deployed and adjusted in a similar manner using second through-slot 526b, second skive 528b and second knots $K_{2A}$ and $K_{2B}$.

As will be apparent to those of skill in the art, although anchor delivery system 500 illustratively has been described in a configuration suited for delivery of only two anchor assemblies, any number of anchor assemblies may be accommodated, for example, by adding additional pairs of motion limitation through-slots and unidirectional adjustment skives to needle tube 520. Additionally, spacers, for example, digestible spacers, wax spacers, polymer spacers, etc., may be provided between anchors and/or between anchor assemblies to reduce a risk of premature deployment of an anchor or assembly. Additional spacing and motion limitation techniques will be apparent.

Referring now to FIG. 26, an alternative embodiment of anchor delivery system 500 is described. For the purposes of illustration, flexible delivery tube 510 has been omitted from system 500' of FIG. 26. However, it should be understood that anchor delivery system 500' preferably comprises flexible delivery tube 510.

Anchor delivery system 500' is substantially the same as system 500, except that first and second through-slots 526a' and 526b' do not communicate with skive bore 524. Rather, through-slots 526' provide openings between anchor lumen 523 and the exterior of needle tube 520. Additionally, needle tube 520 further comprises first and second motion limitation skives 527a and 527b, which constrain the loops of suture formed by first and second motion limitation knots $K_{1A}$ and $K_{2A}$, respectively. It is expected that anchor delivery system 500' will be easier to manufacture than system 500. Additionally, enhanced suture management is expected, since a substantial length of first suture 39a and second suture 39b is disposed outside of needle tube 520 within lumen 511 of delivery tube 510 (see FIG. 25) during delivery. As with anchor delivery system 500, delivery system 500' may be provided with spacers between anchors and/or anchor assemblies to reduce a risk of premature anchor deployment.

Figure 27A:
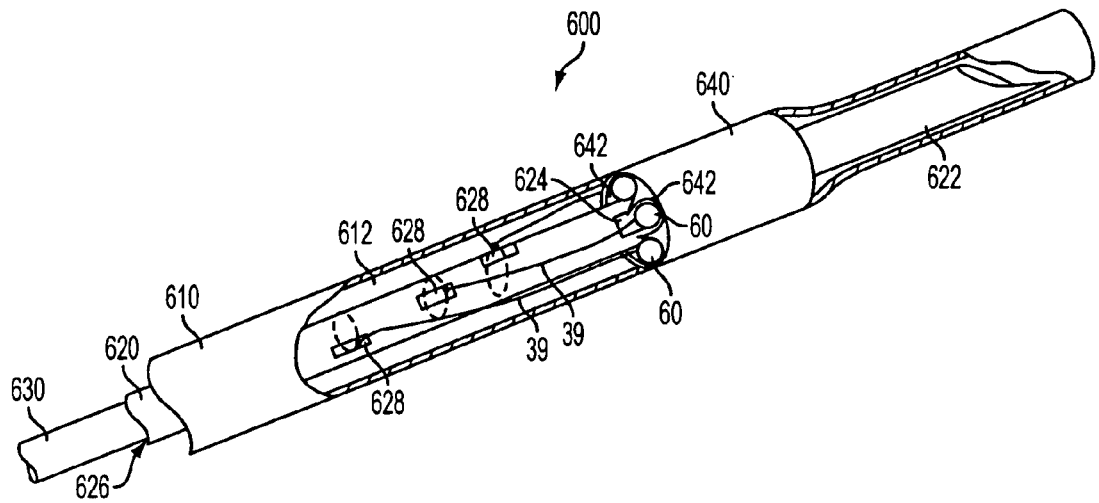
FIGS. 27A and 27B are, respectively, schematic isometric and side views, partially in section, of an alternative anchor delivery system adapted to deliver a plurality of anchor assemblies via a revolver.
Figure 27B:
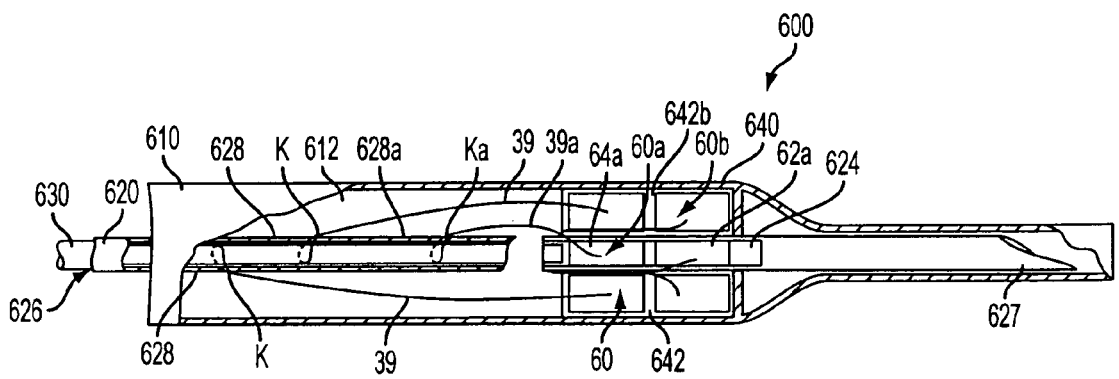

Anchor delivery systems 500 and 500' of FIGS. 25 and 26, respectively, provide for delivery and deployment of multiple adjustable anchor assemblies from a linear stack of anchors disposed within a lumen of the needle tube. FIG. 27 illustrate a first embodiment of an alternative anchor delivery system wherein the multiple anchor assemblies are delivered and deployed from chambers of a radial stack or revolver disposed about the needle tube, without necessitating reloading or removal from the patient. Either the revolver or the needle tube (or both) may be rotated to align the needle tube with successive chambers of the revolver for reloading the needle tube with anchor assemblies from the radial stack.

In FIG. 27, anchor delivery system 600 comprises flexible delivery tube 610, flexible needle tube 620, anchor pushrod 630 and revolver 640. Flexible delivery tube 610 comprises lumen 612. Needle tube 620 comprises needle 622, anchor loading slot 624, anchor lumen 626 and plurality of adjustment skives 628. Skives 628 are disposed over a longitudinal length of needle tube 620 and optionally may be disposed at varying radial positions about needle tube 620. Anchor pushrod 630 is translatably disposed within anchor lumen 626 of needle tube 620 for deployment and adjustment of anchor assemblies 60, and both needle 622 and anchor slot 624 communicate with lumen 626. Revolver 640, comprising plurality of chambers 642, preferably is coupled to, or is integral with, flexible delivery tube 610. Chambers 642 communicate with lumen 612 of flexible delivery tube 610.

Chambers 642 preferably are pre-loaded with plurality of anchor assemblies 60. Furthermore, lumen 626 of needle tube 620 preferably is pre-loaded with first anchor assembly 60a. Sutures 39 extend proximally from anchor assemblies 60 to skives 628, where sutures 39 form knotted suture loops K that are reversibly constrained within lumen 626 of needle tube 620 by anchor pushrod 630, in order to facilitate adjustment of the length of suture disposed between the proximal and distal anchors of each assembly, as discussed previously.

Suture 39a of first anchor assembly 60a extends proximally from first proximal anchor 64a through anchor loading slot 624 to first skive 628a, where it forms first knotted suture loop $K_a$. In use, anchor pushrod 630 may be used to deploy first anchor assembly 60a from lumen 626 of needle tube 620, for example, with distal anchor 62a disposed on the distal side of a tissue fold and proximal anchor 64a disposed on the proximal side. After adjustment in the manner described previously, anchor pushrod 630 may be retracted proximally to a position proximal of first skive 628a, thereby freeing first knotted suture loop from lumen 626. Proximal retraction of anchor delivery system 600 with respect to first anchor assembly 60a completely removes suture 39a from the delivery system, thereby completing deployment of first anchor assembly 60a.

As discussed previously, chambers 642 of revolver 640 communicate with lumen 612 of flexible delivery tube 610. This facilitates loading of successive anchor assemblies 60 within needle tube 620 by longitudinally and radially aligning successive loaded chambers 642 of revolver 640 with anchor loading slot 624 of the needle tube. Needle tube 620 and revolver 640 optionally may be initially aligned such that second anchor assembly 60b disposed in chamber 642b drops through anchor loading slot 624 into lumen 626 of anchor tube 620 upon retraction of anchor pushrod 630 proximal of anchor loading slot 624, e.g., while releasing first knotted suture loop $K_a$ from lumen 626. Subsequent loading of anchor assembly 60c, etc., post-deployment, -adjustment and -release of anchor assembly 60b, may be achieved by rotating needle tube 520 with respect to revolver 540/delivery tube 510, or vice versa.

In this manner, plurality of anchor assemblies 60 may be delivered and deployed without necessitating reloading or removal of anchor delivery system 600 from the patient. In FIG. 27, revolver 640 illustratively is shown with three loaded chambers 642. However, any alternative number of chambers and anchor assemblies may be provided, as will be apparent to those of skill in the art. Additionally, optional motion limitation apparatus may be provided. Furthermore, detents, color-coding or other mechanisms may be provided to facilitate proper radial and longitudinal alignment of delivery tube 610, needle tube 620 (as well as anchor loading slot 624 and skives 628 of the needle tube), anchor pushrod 630 and revolver 640 (as well as successive chambers 642 of the revolver) relative to one another.

Figure 28A:
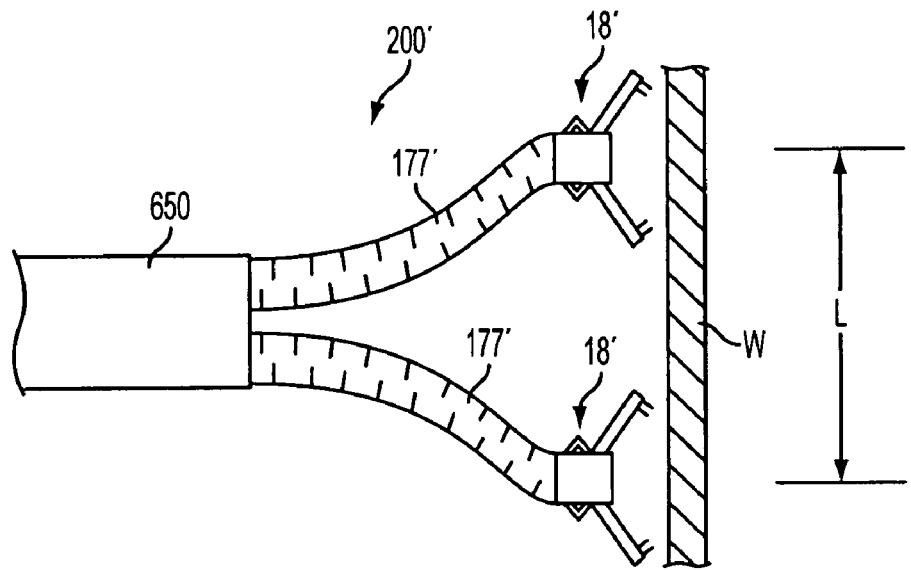
FIGS. 28A and 28B are side views of an alternative embodiment of the apparatus of FIG. 20 illustrating a method for simultaneously forming and approximating multiple gastrointestinal tissue folds.

With reference now to FIGS. 28-34, additional plication apparatus for forming tissue folds is described. FIG. 28 illustrates an alternative embodiment of apparatus 200 of FIG. 20. Apparatus 200' is adapted to simultaneously or sequentially form and approximate a plurality of tissue folds F within tissue wall W. Apparatus 200' may be used in conjunction with any of the anchors and anchor delivery systems described hereinabove, as well as with any applicable alternative anchors or systems, to secure the approximated tissue folds together. It is expected that approximating and securing a plurality of tissue folds will have substantial utility in performing a variety of medical treatments including, for example, gastric reduction.

Figure 28B:
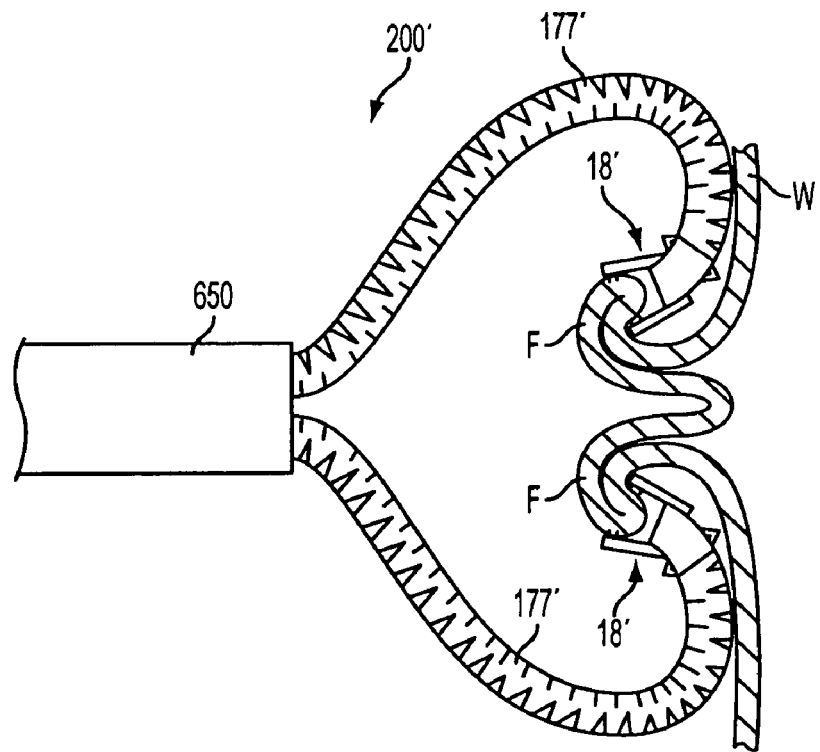

In FIG. 28, apparatus 200' comprises a plurality of articulate-able, flexible tubes 177', each with a tissue grabbing assembly 18'. Tubes 177' preferably are biased such that the tubes flare outward distal of sheath 650, thereby ensuring that the portions of tissue wall W plicated to form tissue folds F are separated by an appropriate distance prior to approximation, and that the tubes resiliently return to their flared position post-plication and release of tissue wall W. Tubes 177' preferably may be translated relative to sheath 650. As seen in FIG. 28B, flexible tubes 177' articulate inward toward a longitudinal axis of apparatus 200' in order to form and approximate tissue folds F. As will be apparent to those of skill in the art, a magnitude of the outward bias applied to tubes 177' may be specified such that an appropriate initial separation distance L between the tissue grasping assemblies for a desired medical treatment is achieved. Furthermore, in order to reduce a delivery profile of apparatus 200', flexible tubes 177' may be disposed within sheath 650 (or another external sheath) during delivery.

Figure 29:
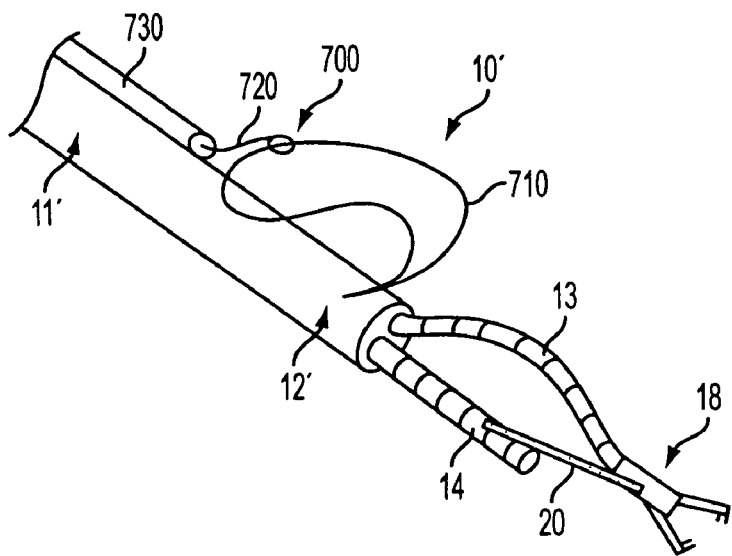
FIG. 29 is an isometric view of an alternative embodiment of the apparatus of FIG. 1 for forming a gastrointestinal tissue fold comprising backside stabilization.

With reference to FIG. 29, an alternative embodiment of apparatus 10 of FIG. 1 is described comprising backside stabilization. All plication apparatus described hereinabove comprise a distal region including a tissue grabbing assembly adapted to engage and stretch a portion of a tissue wall within a GI lumen at a first tissue contact point. A second tissue contact point then is established with the tissue wall at a location initially proximal of, or in line with, the first tissue contact point. The tissue engaged by the tissue grabbing assembly then is moved to a position proximal of the second tissue contact point to form a tissue fold, and an anchor assembly may be delivered across the tissue fold, e.g. across the muscularis and serosa layers of the tissue wall.

Apparatus 10' of FIG. 29 is a first embodiment of apparatus adapted to establish a third tissue contact point at another location initially proximal of, or in line with, the first tissue contact point; additional embodiments will be described hereinbelow. Upon movement of the tissue engaged by the tissue grabbing assembly to a position proximal of both the second and third tissue contact points, a tissue fold is formed with the second and third contact points on opposing sides of the fold. The second and third contact points provide both front and backside stabilization, respectively, of the tissue fold. When delivering an optional anchor assembly across the tissue fold from a vicinity of the second tissue contact point, backside stabilization at the third tissue contact point reduces backside tenting of tissue, thereby facilitating anchor delivery.

In FIG. 29, apparatus 10' of the present invention comprises torqueable catheter 11', which may be configured, for example, for insertion through a patient's mouth and esophagus into the patient's gastrointestinal lumen. Catheter 11' comprises distal region 12' having first and second interconnected flexible tubes 13 and 14 extending therefrom. Tubes 13 and 14 are joined by hinge assembly 20, and tissue grabbing assembly 18 is disposed on the distal end of flexible tube 13. The tissue grabbing assembly is coupled to a control wire (not shown) that extends through tube 13 to a proximal region of catheter 11' (not shown).

Distal region 12' of apparatus 10' is substantially the same as distal region 12 of apparatus 10 of FIG. 1, except that distal region 12' further comprises selectively deployable backside stabilizer 700. Backside stabilizer 700 comprises wire loop 710, which preferably is fabricated from a loop of shape memory material, e.g. Nitinol, coupled to control wire 720 that extends from wire tube 730. The proximal region of catheter 11' comprises actuators (not shown) in communication with the tissue grabbing assembly control wire and control wire 720 for actuating the tissue grabbing assembly and the backside stabilizer, respectively.

Figure 30A:
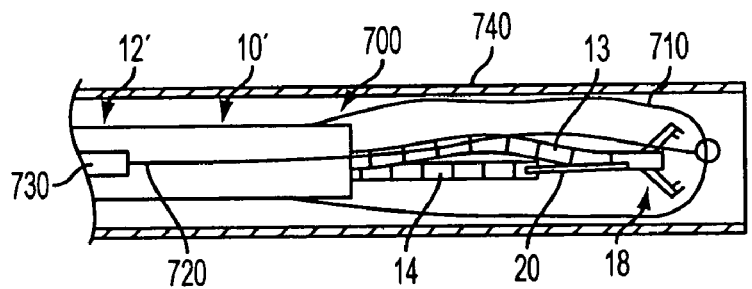
FIGS. 30A-30E are a side view, partially in section, and isometric views illustrating a method of using the apparatus of FIG. 29 to form a backside stabilized gastrointestinal tissue fold.
Figure 30B:
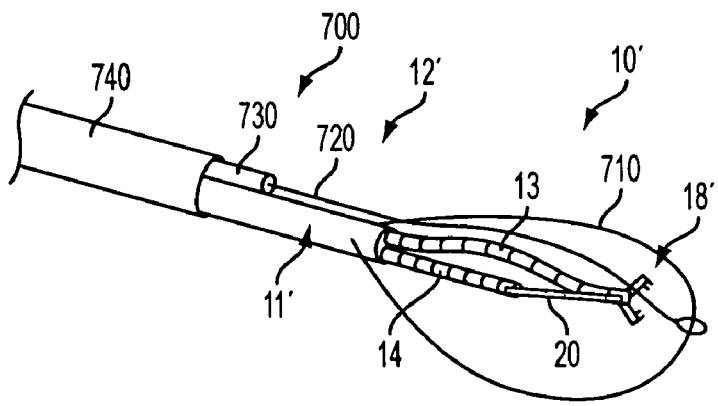
Figure 30C:
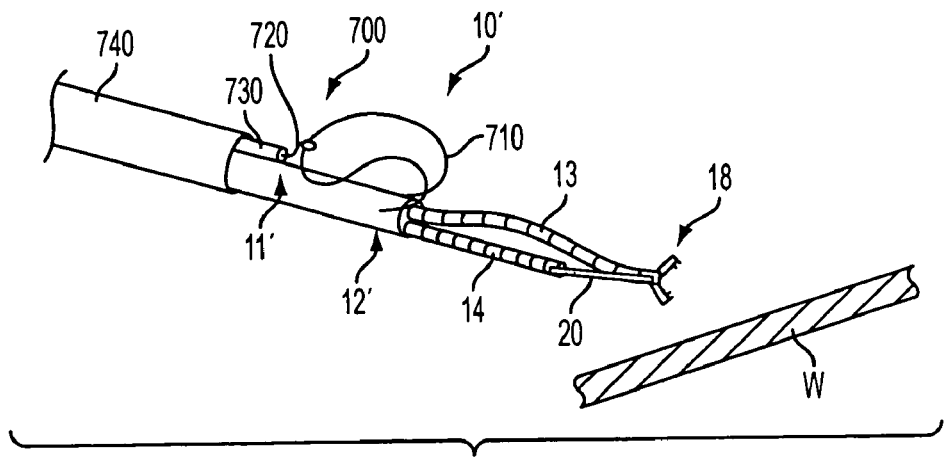
Figure 30D:
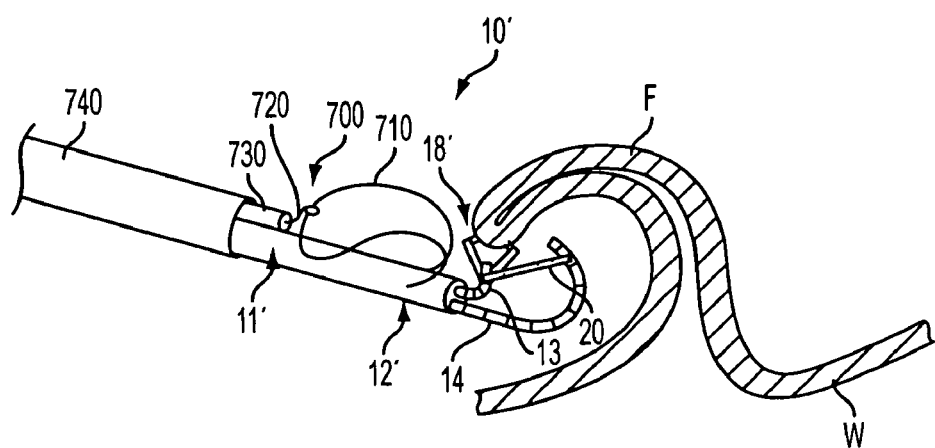

Referring to FIGS. 30A-30E, a method of using apparatus 10' of FIG. 29 to form a backside stabilized tissue fold is described. In FIG. 30A, apparatus 10' is delivered to a treatment site through delivery sheath 740 with wire loop 710 compressed to a reduced delivery configuration within the delivery sheath. In FIG. 30B, distal region 12' of catheter 11' is advanced distal of delivery sheath 740, such that wire loop 710 expands to a free-space configuration. In FIG. 30C, control wire 720 of backside stabilizer 700 is retracted proximally to retract wire loop 710 to an intermediate ready position. In FIG. 30D, tissue fold F is formed at tissue wall W with distal region 12', e.g., as described hereinabove with respect to FIG. 3.

Figure 30E:
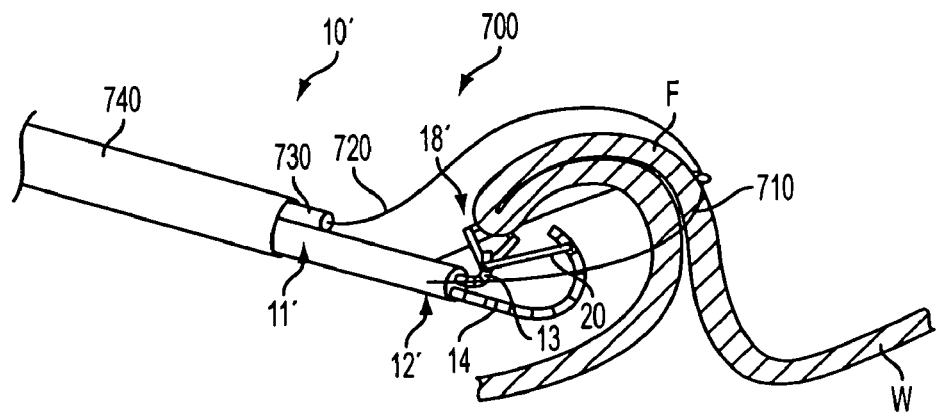

In FIG. 30E, tension is released from control wire 720, and wire loop 710 resiliently moves back towards its free-space configuration. Wire loop 710 of backside stabilizer 700 establishes a third tissue contact point on the backside of tissue fold F, thereby providing backside stabilization to the tissue fold. It is expected that backside stabilization/establishment of an opposing third tissue contact point will simplify delivery of an anchor assembly across the tissue fold while facilitating formation and securing of a serosa-to-serosa fold.

As will be apparent to those of skill in the art, the size, length or diameter of wire loop 710 may be adjustable to facilitate backside stabilization of tissue folds of variable size. Furthermore, wire loop 710 may may be provided as a substantially stagnant loop, i.e. the loop may not be retractable via control wire 720. In such a configuration, wire loop 710 would apply pressure to the tissue fold as it is formed, thereby facilitating formation of the fold in addition to providing stabilization.

With reference now to FIG. 31, further alternative tissue folding apparatus comprising optional backside stabilization is described. Apparatus 800 is adapted to linearly retract tissue at tissue wall W in order to form tissue fold F. The apparatus comprises catheter 810 having tissue grabbing assembly 18; such as described hereinabove and comprising a pair of jaws 28a, 28b having sharpened teeth 33 arranged to rotate about pivot point 29 between an open configuration and a closed configuration; coupled to tube 820 having slot 822. Control wire 19 is disposed within the lumen of tube 820 and extends from tissue grabbing assembly 18 to a proximal end of apparatus 800 (not shown) for actuating the tissue grabbing assembly. Tissue grabbing assembly 18 is configured to establish a first tissue contact point with tissue wall W and may be retracted proximally via tube 820 to facilitate formation of tissue fold F.

Apparatus 800 further comprises frontside and backside linkages 830a and 830b, respectively. Proximal regions of the linkages are pivotably and translatably disposed within slot 822 of tube 820. A distal region of frontside linkage 830a is pivotably coupled to anchor delivery tube 840 for delivery of an anchor assembly across a tissue fold, as described previously, while a distal region of backside linkage 830b is pivotably coupled to backside stabilizer 850. Anchor delivery tube 840 and backside stabilizer 850 preferably are biased such that they substantially align with the longitudinal axis of apparatus 800 when not under stress. Such alignment may be achieved, for example, by forming the elements from spring tube, or by providing the elements with resilient spines, e.g. Nitinol spines. Tube 840 and stabilizer 850 are configured to establish second and third tissue contact points, respectively, at tissue wall W, thereby providing frontside and backside stabilization of a tissue fold formed at the wall, as described hereinabove.

Figure 31A:
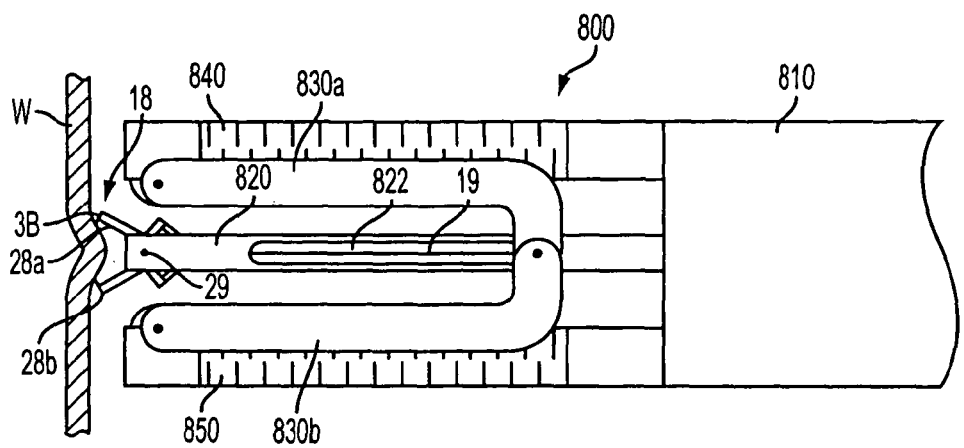
FIGS. 31A-31C are side views of further alternative tissue folding apparatus illustrating a method for forming a gastrointestinal tissue fold via a linear displacement of tissue.
Figure 31B:
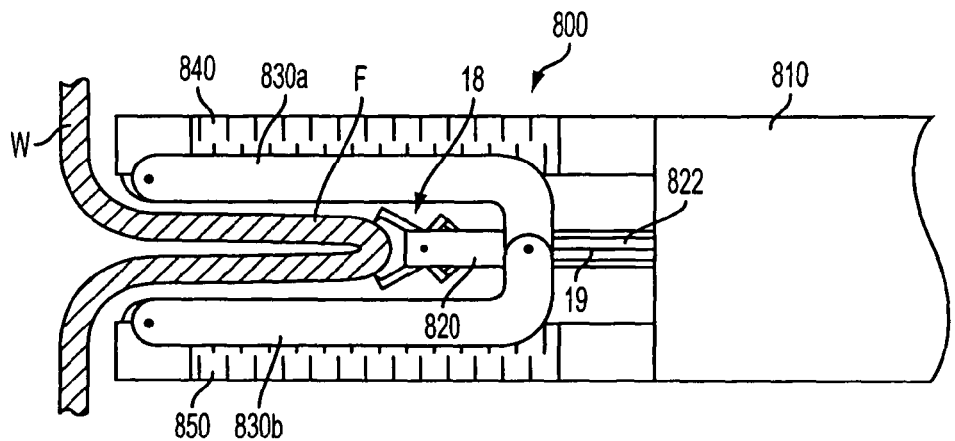

Referring again to FIG. 31, a method of using apparatus 800 to form tissue fold F at tissue wall W is described. In FIG. 31A, tissue grabbing assembly 18 has been advanced to a vicinity of tissue wall W with the proximal ends of linkages 830 disposed near the proximal end of slot 822 in tube 820. Tissue grabbing assembly 18 is then actuated via retraction of control wire 19 to grab tissue and establish the first tissue contact point. With tissue engaged, continued retraction of control wire 19 causes proximal retraction of tube 820 and assembly 18 in a substantially linear fashion relative to linkages 830, as seen in FIG. 31B.

Figure 31C:
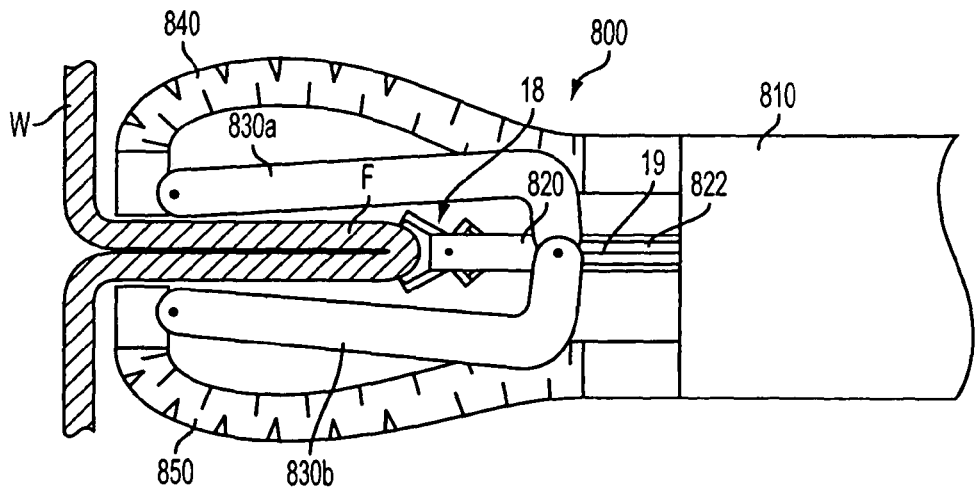

As tube 820 is linearly retracted, linkages 830 slidably translate within slot 822 of the tube 820 until the proximal regions of the linkages contact a distal end of slot 822. As seen in FIG. 31C, further proximal retraction of tube 820 beyond this bottoming-out point of slot 822 causes linkages 830 to rotatably pivot at both their proximal and distal regions. This, in turn, causes anchor delivery tube 840 and backside stabilizer 850 to rotate inwards and form the second and third tissue contact points, respectively, thereby forming frontside and backside-stabilized tissue fold F. Upon re-advancement of tube 820, anchor delivery tube 840 and backside stabilizer 850 resiliently realign with the longitudinal axis of apparatus 800.

Previous plication apparatus described hereinabove require more complex motion than linear retraction on the part of the tissue grabbing assembly in order to form tissue fold F. It is expected that reducing movement of the tissue grabbing assembly during tissue folding to a linear motion will reduce a magnitude of working space required at a treatment site to achieve formation of the tissue fold. As will be apparent to those of skill in the art, as an alternative to linearly retracting tube 820 relative to linkages 830 in order to form tissue fold F, linkages 830 may be linearly advanced relative to tube 820. Also, backside linkage 830b and backside stabilizer 850 (as well as concomitant backside stabilization of tissue fold F) optionally may be omitted. Alternatively, backside stabilizer 850 may comprise a second anchor delivery tube, e.g., for delivery of an anchor assembly across tissue fold F from the backside, for passage of all or part of an anchor assembly from frontside anchor delivery tube 840 to the backside stabilizer across the tissue fold, or for delivery of a multiple component anchor assembly having a first component deployable from the frontside anchor delivery tube and a second component deployable via the backside stabilizer. The first and second components optionally may be coupled together to form a composite anchor assembly. Additional configurations will be apparent to those of skill in the art.

Furthermore, slot 822 optionally may be omitted from tube 820, and the tube alternatively may be provided with proximal and distal stops disposed on the exterior of, or formed integral with, the tube near its distal end. In this arrangement, the proximal ends of linkages 830 would be pivotably and translatably disposed about the exterior of tube 820, such that the proximal and distal stops limit translation of the linkages relative to the tube. In both this arrangement and the arrangement of FIG. 31, tube 820 acts as a linear bearing about which linkages 830 may travel.

Figure 32:
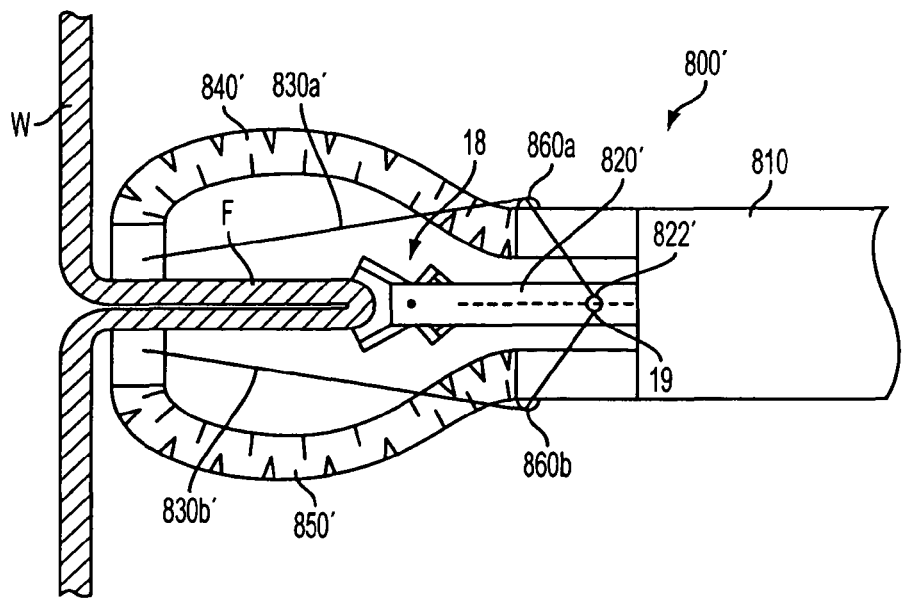
FIG. 32 is a side view of an alternative embodiment of the apparatus of FIG. 31 providing enhanced flexibility.

With reference now to FIG. 32, an alternative embodiment of apparatus 800 of FIG. 31 is described. Apparatus 800' is substantially the same as apparatus 800, except that linkages 830 have been replaced with control wires 830', while slot 822 of tube 820 has been replaced with skive 822' of tube 820'. Additionally, anchor delivery tube 840' and backside stabilizer 850' comprise optional pulley eyelets 860a and 860b, respectively, for routing of control wires 830'. Control wires 830' are proximally coupled to control wire 19 of tissue grabbing assembly 18 within the lumen of tube 820'. Control wires 830' exit the lumen at skive 822' and extend distally through optional pulley eyelets 860. Control wire 830a' is distally coupled to anchor delivery tube 840', while control wire 830b' is distally coupled to backside stabilizer 850'.

A length of control wires 830' is specified such that retraction of control wire 19 causes actuation of tissue grabbing assembly 18 and retraction of tube 820', prior to control wires 830' being pulled taut. Once control wires 830' have been pulled taut, continued retraction of control wire 19 causes control wires 830' to reversibly rotate anchor delivery tube 840' and backside stabilizer 850' inward, thereby forming the second and third tissue contact points and forming frontside- and backside-stabilized tissue fold F at tissue wall W. As with apparatus 800, backside stabilizer 850' (as well as associated control wire 830b') of apparatus 800' optionally may be omitted.

Figure 33A:
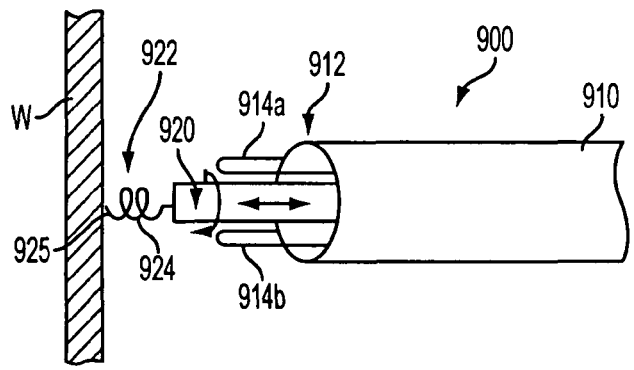
FIGS. 33A and 33B are side views of further alternative front and backside stabilized linear displacement plication apparatus, illustrating a method for forming a gastrointestinal tissue fold.
Figure 33B:
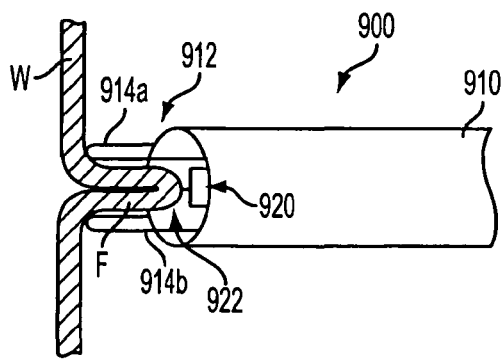

Referring to FIG. 33 further alternative tissue folding apparatus comprising optional backside stabilization is described. Apparatus 900 comprises outer tube 910 having distal region 912 with rigid or resilient frontside and backside stabilizers 914a and 914b, respectively. When substantially rigid, stabilizers 914 may be formed, for example, from a shaped stainless steel wire or rod. When resilient, the stabilizers may be formed, for example, from a wire or rod of shape memory material such as Nitinol or from a thinner wire or rod of stainless steel. The durometer of the material used to fabricate stabilizers 914 may be specified to achieve a desired degree of rigidity or resiliency.

Apparatus 900 further comprises inner tube 920, which is coaxially and slidably disposed within outer tube 910. Tissue grabbing assembly 922, coupled to a distal region of inner tube 910, comprises helical coil 924 having sharpened distal tip 925. Helical coil 924 is adapted to reversibly engage tissue by reversibly screwing the coil into the tissue in a manner similar to a wine corkscrew, and as demonstrated by arrows in FIG. 33A. As will be apparent to those of skill in the art, as an alternative or adjunct to helical coil 924, tissue grabbing assembly 922 may comprise a jaw structure similar to that of assembly 18; likewise any of the previously described tissue folding apparatus optionally may comprise a tissue grabbing assembly having a helical coil. Additional tissue grabbing assemblies, per se known, will be apparent in view of this disclosure.

FIG. 33 illustrate a method of forming a tissue fold with apparatus 900. In FIG. 33A, tissue grabbing assembly 922 is advanced distal of stabilizers 914 to engage tissue at tissue wall W at a first tissue contact point. Helical coil 924 is screwed into the tissue, and inner tube 920 is then retracted relative to outer tube 910, and/or the outer tube is advanced relative to the inner tube, such that tissue engaged by assembly 922 is pulled proximal of stabilizers 914, as seen in FIG. 9B. Stabilizers 914 contact the tissue at second and third contact points, and form frontside- and backside-stabilized tissue fold F. When rigid, a cross-sectional width of tissue fold F may be specified by a separation distance between the frontside and backside stabilizers. When resilient, the stabilizers may bow outward to facilitate formation of the tissue fold by decreasing a pulling force required by coil 924 to form the fold, as well as by reducing a risk of the coil detaching from, or tearing through, the tissue during fold formation.

As will be apparent to those of skill in the art, one of stabilizer 914a and stabilizer 914b optionally may be omitted when only a second tissue contact point is required. Additionally, apparatus 900 may be used in conjunction with an anchor delivery system, such as those described previously; the anchor delivery system optionally may provide the third tissue contact point. Also, one or both of stabilizers 914 may be extendable/retractable relative to distal region 912 of outer tube 910 of apparatus 900. Likewise, the stabilizers may be sizable in vivo to facilitate formation of a tissue fold of specified magnitude.

With reference now to FIG. 34, another embodiment of plication apparatus comprising backside stabilization is described. In contrast to previously described apparatus, apparatus 950 achieves backside stabilization of a tissue fold via tissue contact over an arcuate segment, as opposed to at discrete points or along a line. In FIG. 34, full 360° radial contact around the fold is established; however, as will be apparent to those of skill in the art, contact alternatively may be established at one or more locations over one or more arcuate segments of less than 360°.

Apparatus 950 comprises inner tube 960 and coaxially disposed outer tube 970. Inner tube 960 comprises tissue grabbing assembly 18 coupled to a distal of the tube. Apparatus 950 further comprises braided mesh 980 having proximal end 982 coupled to a distal end of outer tube 970, and distal end 984 coupled to inner tube 960 proximal of tissue grabbing assembly 18. Braided mesh 980 preferably is fabricated from polymer or metal wires. Upon advancement of outer tube 970 relative to inner tube 960, the mesh may be everted, e.g. over a tissue fold, to provide frontside and backside stabilization of a fold via arcuate contact. As will be apparent, apparatus 950 may be used in conjunction with an anchor delivery system to secure a stabilized tissue fold.

Figure 34A:
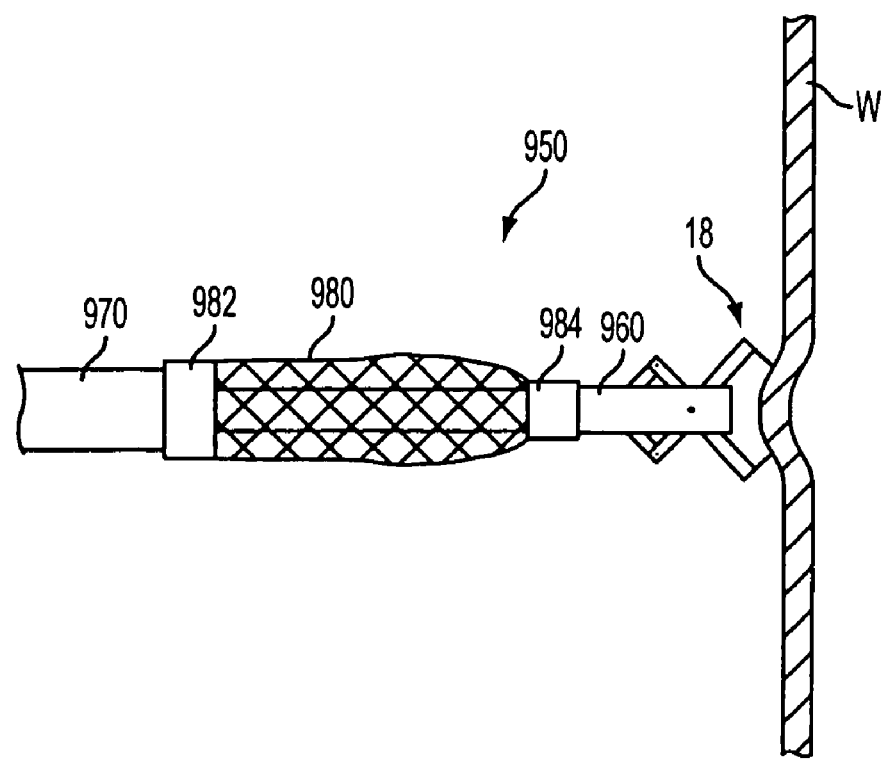
FIGS. 34A and 34B are, respectively, a side view and a side view, partially in section, of still further alternative apparatus illustrating a method for forming a stabilized gastrointestinal tissue fold via a braided mesh.
Figure 34B:
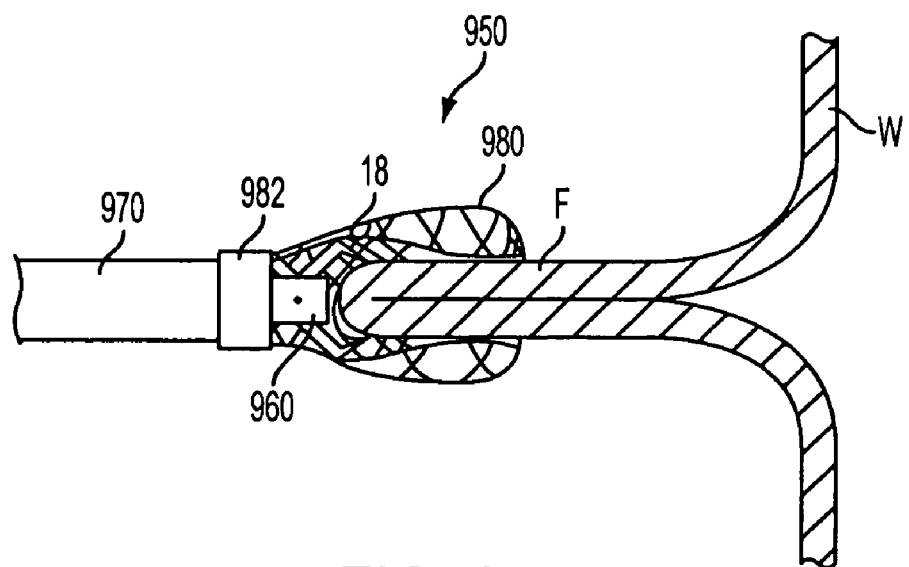

FIG. 34 illustrate a method of using apparatus 950 to form a stabilized tissue fold. In FIG. 34A, tissue grabbing assembly 18 engages tissue wall W at a first tissue contact point. In FIG. 34B, with tissue engaged by assembly 18, inner tube 960 is retracted relative to outer tube 970 and/or outer tube 970 is advanced relative to inner tube 980, such that proximal end 982 is advanced distal of distal end 984 of braided mesh 980. The braided mesh everts about tissue fold F, thereby providing frontside and backside stabilization to the tissue fold via contact over a full 360° radial segment (braided mesh 980 shown in section in FIG. 34B).

FIGS. 29-34 have illustrated exemplary plication apparatus comprising optional elements for backside stabilizing tissue folds formed with the apparatus. As will be apparent to those of skill in the art, backside stabilization elements optionally may also be provided with any other plication apparatus of the present invention. Furthermore, backside stabilization elements may be provided with any anchor delivery system, e.g., in order to reduce tissue tenting during deployment of an anchor assembly across a tissue fold.

With reference now to FIGS. 35-39, an embodiment of a shape-lockable guide for use with tools of the present invention is described. Shape-lockable guides have been described previously in Applicant's co-pending U.S. patent application Ser. No. 10/173,203, filed Jun. 13, 2002, which is incorporated herein by reference in its entirety and from which the present invention claims priority. As discussed hereinabove, a significant indication for use of the tissue grabbing assemblies, plication apparatus, anchor delivery systems and anchor assemblies of the present invention is within a patient's gastrointestinal ("GI") lumen. However, the GI lumen varies significantly in geometry and material properties along its length, and it is expected that properly positioning, as well as visualizing, endoluminal tools of the present invention at any desired location within the GI lumen will present significant challenges. Transmitting forces and torques to the tools over substantial separation distances between a medical practitioner and the working ends of the tools within the GI lumen presents additional challenges. It therefore would be nice to provide guide apparatus capable of providing exposure or targeting, stability, and flexibility to tools of the present invention when disposed within a patient.

Apparatus 1000 of FIGS. 35-39 addresses these challenges by facilitating placement of a diagnostic instrument, such as an endoscope, e.g., a colonoscope or gastroscope; and/or a therapeutic instrument, such as those described hereinabove; through the tortuous or unpredictably supported anatomy of a hollow body organ, such as the colon, esophagus and/or stomach; while reducing a risk of distending or injuring the organ. Apparatus 1000 permits such instruments to be readily advanced into the patient's tortuous or unpredictably supported anatomy by selectively shape-fixing an overtube portion of the apparatus, while also preventing tissue from being captured or pinched between the overtube and the instrument(s). Although apparatus 1000 illustratively comprises an overtube, it should be understood that apparatus 1000 alternatively may comprise a selectively rigidizable, shape-fixing or shape-locking guide wire or inner conduit, over which diagnostic or therapeutic instruments may be advanced.

Figure 35:
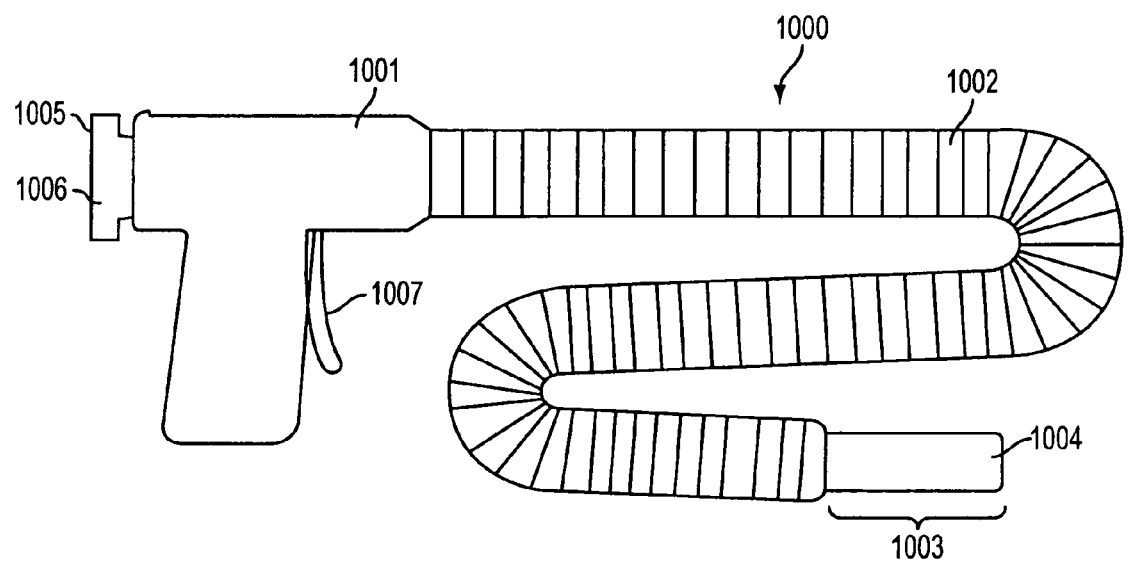
FIG. 35 is a side view of illustrative shape-lockable apparatus for use with the tissue folding and anchor delivery apparatus of the present invention.

Referring now to FIG. 35, apparatus 1000 of the present invention is described. Apparatus 1000 comprises handle 1001, overtube 1002, and distal region 1003 having atraumatic tip 1004. Handle 1001 includes lumen 1005 that extends from Toughy-Borst valve 1006 through overtube 1002, distal region 1003 and atraumatic tip 1004. Lumen 1005 is configured to facilitate passage of a standard commercially available endoscope, such as endoscope 1100 having steerable distal tip 1101 (see FIG. 40), and/or a therapeutic device of the present invention, e.g. a tissue grabbing assembly, plication apparatus, an anchor delivery system, or an anchor assembly, therethrough. Although apparatus 1000 illustratively comprises a single lumen, multiple lumens optionally may be provided for passage of multiple diagnostic and/or therapeutic instruments. Toughy-Borst valve 1006 may be actuated to releasably lock instrument(s) to apparatus 1000 when the instrument(s) are inserted within lumen 1005. As described hereinafter, overtube 1002 is configured so that it can be selectively transitioned between a flexible state and a rigid, shape-fixed state by actuator 1007 disposed on handle 1001.

Figure 36:
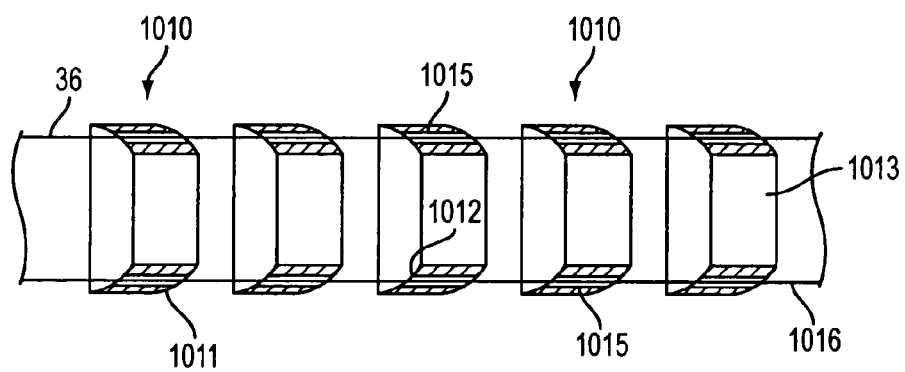
FIG. 36 is a side-sectional exploded view of nestable elements of a first embodiment of an overtube suitable for use with the shape-lockable apparatus of FIG. 35.

In FIG. 36, an illustrative embodiment of overtube 1002 comprises a multiplicity of nestable elements 1010. For purposes of illustration, nestable elements 1010 are shown spaced-apart, but it should be understood that elements 1010 are disposed so that their adjacent surfaces 1011 and 1012 coact. Each of nestable elements 1010 has central bore 1013 to accommodate diagnostic and therapeutic instruments, and preferably three or more tension wire bores 1015. When assembled as shown in FIG. 35, nestable elements 1010 are fastened with adjacent surfaces 1011 and 1012 disposed in a coacting fashion by a plurality of tension wires 1016 that extend through tension wire bores 1015.

In a preferred embodiment, adjacent surfaces 1011 and 1012 of each nestable element 1010 are contoured to mate with the next adjacent element, so that when tension wires 1016 are relaxed, surfaces 1011 and 1012 can rotate relative to one another. Tension wires 1016 are fixedly connected to the distal end of overtube 1002 at their distal ends and to a tensioning mechanism disposed within handle 1001 at their proximal ends. When actuated by actuator 1007, tension wires 1016 impose a load that clamps adjacent surfaces 1011 and 1012 of nestable elements 1010 together at the current relative orientation, thereby fixing the shape of overtube 1002.

When the load in tension wires 1016 is released, tension wires 1016 provide for relative angular movement between nestable elements 1010. This in turn renders overtube 1002 sufficiently flexible to negotiate a tortuous path or unpredictably supported anatomy through, for example, any region of a patient's GI lumen, such as the colon, esophagus and/or stomach. When the tensioning mechanism is actuated, however, tension wires 1016 are retracted proximally to apply a clamping load to the nestable elements. This load prevents further relative movement between adjacent elements 1010 and stiffens overtube 1002, so that any distally directed force applied to instruments within lumen 1005 causes the working ends of the instruments to advance further into the GI lumen, rather than cause overtube 1002 to bear against the wall of the lumen or lose its spatial orientation within an unpredictably supported space. The shape-fixed overtube absorbs and distributes vector forces, shielding the GI lumen.

Figure 37:
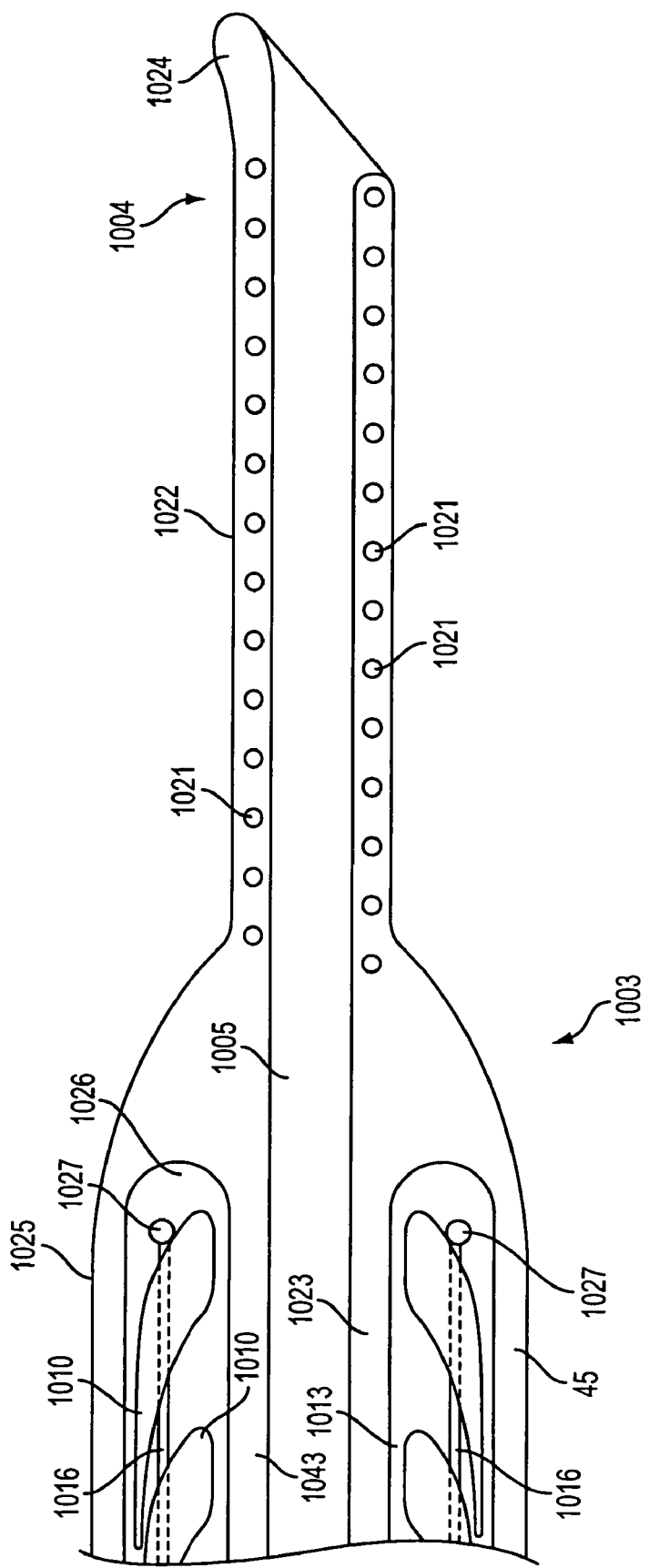
FIG. 37 is a side-sectional view of a distal region of the apparatus of FIG. 35 constructed in accordance with principles of the present invention.

Referring now to FIG. 37, an illustrative embodiment of distal region 1003 and atraumatic tip 1004 is described. Distal region 1003 comprises flexible, kink-resistant coil 1021 encapsulated in flexible layer 1022. Layer 1022 preferably comprises a soft elastomeric and hydrophilic coated material, such as silicon or synthetic rubber, and extends through bores 1013 of nestable elements 1010 to form liner 1023 for lumen

1005. Layer 1022 extends to handle 1001 at the proximal end, and at the distal end terminates in enlarged section 1024 that forms atraumatic tip 1004.

Layer 1022 preferably joins with or is integrally formed with flexible elastomeric cover 1025 which encapsulates nestable elements 1010 in annular chamber 1026. Cover 1025 provides a relatively smooth outer surface for overtube 1002, and prevents tissue from being captured or pinched during relative rotation of adjacent nestable elements 1010.

In accordance with one aspect of the present invention, endoscope 1100 may be positioned with its distal tip 1101 disposed in distal region 1003, so that deflection of steerable distal tip 1101 imparts an angular deflection to distal region 1003 and atraumatic tip 1004. To ensure that there is no gross relative motion between endoscope 1100 or other instruments within lumen 1005 and apparatus 1000, Toughy-Borst valve 1006 is tightened to engage apparatus 1000 to the endoscope/ instruments. In this manner, the instrument(s) and distal region 1003 may be simultaneously advanced through the colon, with the distal tip of endoscope 1100 providing a steering capability to apparatus 1000. Apparatus 1000 therefore may be advantageously advanced together with instruments disposed within lumen 1005 when overtube 1002 is in the flexible state, reducing relative motion between apparatus 1000 and such instruments to those instances where overtube 1002 must be shape-locked to prevent distension or to maintain distal region 1003 orientation with the GI lumen.

Still referring to FIG. 37, terminations 1027 of tension wires are described. Terminations 1027 illustratively comprise balls welded or molded onto the ends of tension wires 1016 that ensure the tension wires cannot be pulled through tension wire bores 1015 of the distalmost nestable element 1010. This ensures that the nestable elements cannot come loose when overtube 1002 is disposed within a patient.

Alternatively, terminations 1027 may comprise knots formed in the ends of tension wires 1016, or any suitable fastener that prevents the tension wires from being drawn through the tension wire bores of the distal-most nestable element. Advantageously, cover 1025 provides additional assurance that all of nestable elements 1010 can be safely retrieved from a patient's colon in the unlikely event of a tension wire failure.

Figure 38:
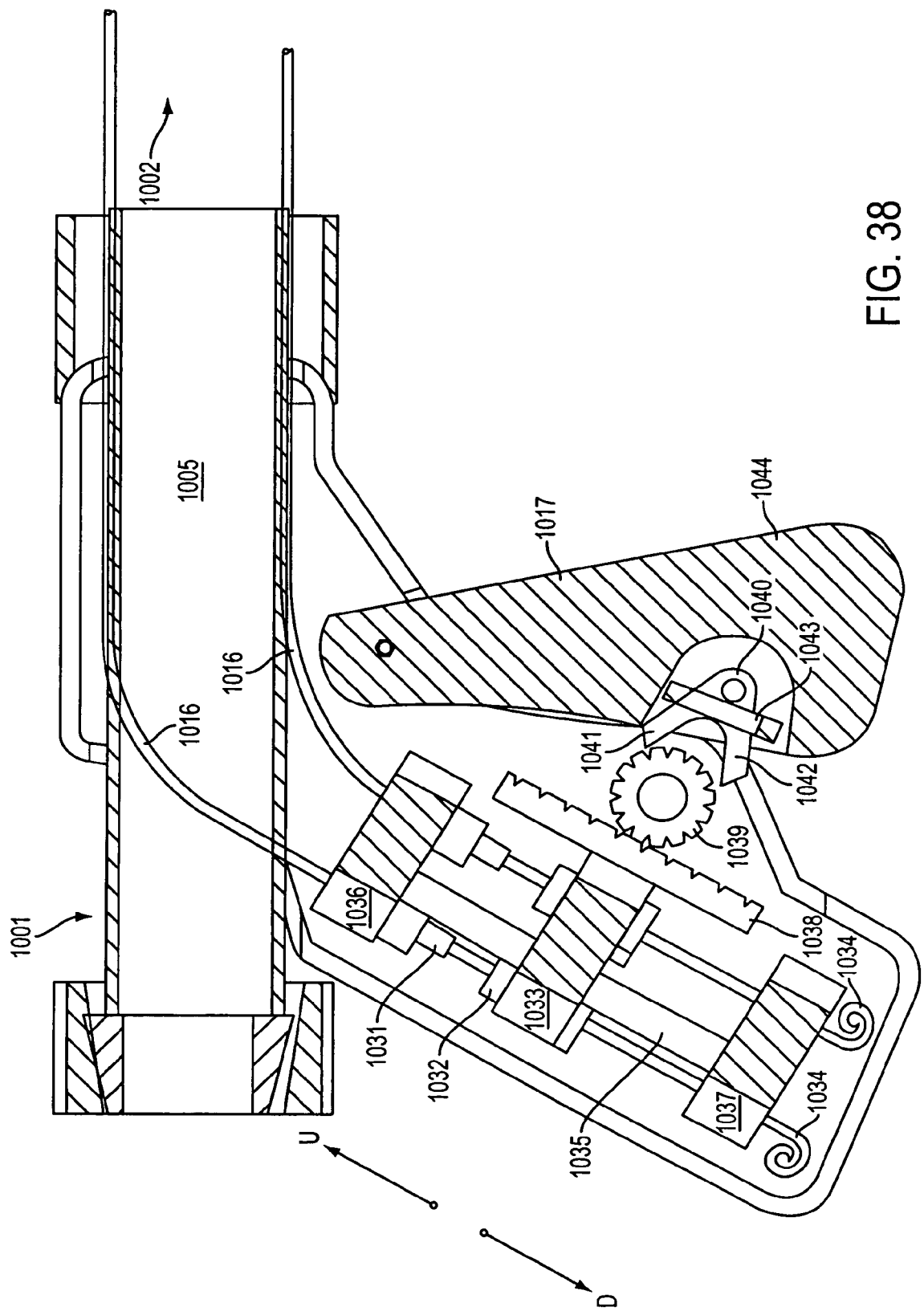
FIG. 38 is a side-sectional view of an illustrative arrangement of a mechanism suitable for use in the handle of the apparatus of FIG. 35.

Referring now to FIGS. 35 and 38, tension wires 1016 within overtube 1002, liner 1023 and lumen 1005 extend from distal region 1003, through overtube 1002, and to handle 1001. Within handle 1001, each tension wire 1016 passes through wire lock release 1031 fixedly attached to handle 1001, and wire lock 1032 disposed on slide block 1033. Each tension wire 1016 terminates at wire tension spring 1034, which maintains tension wires 1016 in light tension even when overtube 1002 is in the flexible state. The degree of tension provided by wire tension springs 1034 is not sufficient to clamp adjacent nestable elements 1010 together, but on the other hand does not let gaps form between adjacent nestable elements, and helps to manage the tension wire take up or slack as overtube 1002 makes various bends.

Slide block 1033 is keyed to slide along rail 1035 disposed between limit blocks 1036 and 1037, and comprises a rigid block having a bore through which rail 1035 extends and an additional number of bores as required for the number of tension wires 1016 employed. Rack gear 1038 is fixedly coupled to slide block 1033. Rack 1038 mates with pinion gear 1039, which is in turn driven by bi-directional pawl 1040 coupled to actuator 1007. Pinion gear 1039 may be selectively engaged by either prong 1041 or 1042 of bidirectional pawl 1040, depending upon the position of selector switch 1043.

If prong 1041 is selected to be engaged with pinion gear 1039, a squeezing action applied to actuator 1007, illustratively hand grip 1044, causes rack 1033 to move in the D direction in FIG. 38, thereby applying tension to tension wires 1016. Repeated actuation of hand grip 1044 causes slide block 1033 to move progressively further in direction D, thereby applying an increasing clamping load on nestable elements 1010. Any slack lengths of tension wires 1016 extending below slide block 1033 are taken up by wire tension springs 1034. As discussed in greater detail below with respect to FIG. 39, wire locks 1032, which are affixed to slide block 1033, engage and retract tension wires 1016 concurrently with movement of slide block 1033 in the D direction.

If prong 1042 is instead chosen by selector switch 1043 to engage pinion gear 1039, repeated actuation of hand grip 1044 causes slide block 1033 to translate in direction U, thereby relaxing the tensile load applied by tension wires 1016 to nestable elements 1010. Repeated actuation of hand grip 1044 causes slide block 1033 to advance in direction U until wire lock releases 1031 engage wire locks 1032, releasing all tension from tension wires 1016 except that provided by wire tension springs 1034. This action permits the clamping forces imposed on nestable elements 1010 to be progressively reduced and render overtube 1002 progressively more flexible, until when wire lock releases 1031 engage wire locks 1032, the overtube is returned to its most flexible state.

Figure 39:
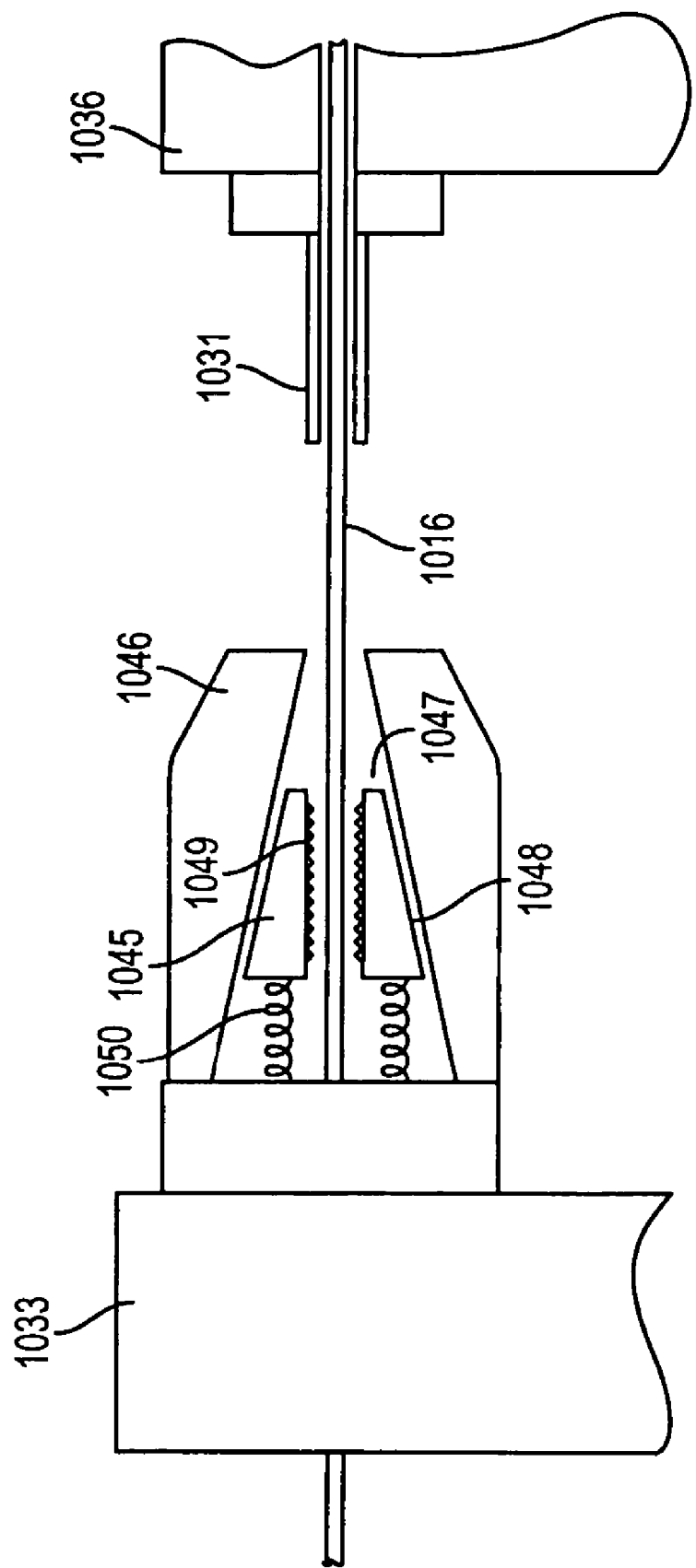
FIG. 39 is a side-sectional view of the detail of a wire clamping system suitable for use in the handle of FIG. 35.

Referring to FIG. 39, wire lock 1032 and lock release 1031 are described in greater detail. Wire lock 1032 includes jaws 1045 disposed within collet 1046. Collet 1046 includes a tapered conical bore 1047. Jaws 1045 have ramped exterior surfaces 1048 and teeth 1049, and are biased against the surface formed by the tapered conical bore by springs 70. Teeth 1049 are configured to engage tension wire 1016 under the bias force of springs 70. When slide block 1033 is moved in direction D (see FIG. 38), jaws 1045 engage and grasp tension wire 1016 and retract the tension wire in direction D.

To disengage teeth 1049 from tension wire 1016, e.g., when it is desired to allow overtube 1002 to return to a flexible state, slide block 1033 is actuated as described previously to move in direction U. Further actuation of slide block 1033 towards limit block 1036 and wire lock release 1031 causes wire lock release 1031 to extend into tapered conical bore 1047 and push jaws 1045 backward against the bias of springs 70. Once tension wires 1016 are freed from jaws 1045, overtube 1002 returns to its most flexible state.

In FIGS. 35-39, apparatus 1000 has been described as having a flexible state and rigid state. However, it should be understood that apparatus 1000 optionally may comprise one or more intermediary states wherein overtube 1002 is only partially flexible or only partially rigid. Furthermore, overtube 1002 optionally may comprise one or more sections of varied rigidity or flexibility in either the flexible or the rigid state, or both, as compared to one or more other sections of the overtube. For example, at least one section of the overtube may remain in the flexible state upon transition of the overtube to the rigid state. Alternatively, at least one section of the overtube may comprise varied rigidity relative to a different section of the overtube when the overtube is disposed in the rigid state. As yet another alternative, at least one section of the overtube may comprise varied flexibility relative to a different section of the overtube when the overtube is disposed in the flexible state. Additional configurations will be apparent to those of skill in the art.

It should be understood that apparatus 1000 optionally may be provided with steering capabilities in addition to locking capabilities, in order to properly position apparatus 1000 within a GI lumen, e.g. prior to locking the overtube in a desired orientation. Such steering capabilities may be achieved, for example, using tensioning or stiffening wires, per se known. Additional steering techniques will be apparent to those of skill in the art.

As an alternative, or in addition, to advancing diagnostic and/or therapeutic instruments through one or more lumens of apparatus 1000, such instruments optionally may be coupled to apparatus 1000. For example, an endoscope, a tissue grabbing assembly, plication apparatus and/or an anchor delivery system in accordance with the present invention, may be coupled to distal region 1003 of apparatus 1000. Alternatively, such instruments may be telescopically disposed and advanced from within distal region 1003. Coupling instruments or tools to a shape-lockable guide is described in more detail, for example, in Applicant's co-pending U.S. patent application Ser. No. 10/458,060, filed Jun. 9, 2003, which is incorporated herein by reference in its entirety and from which the present invention claims priority. Additional configurations will be apparent to those of skill in the art.

Figure 40A:
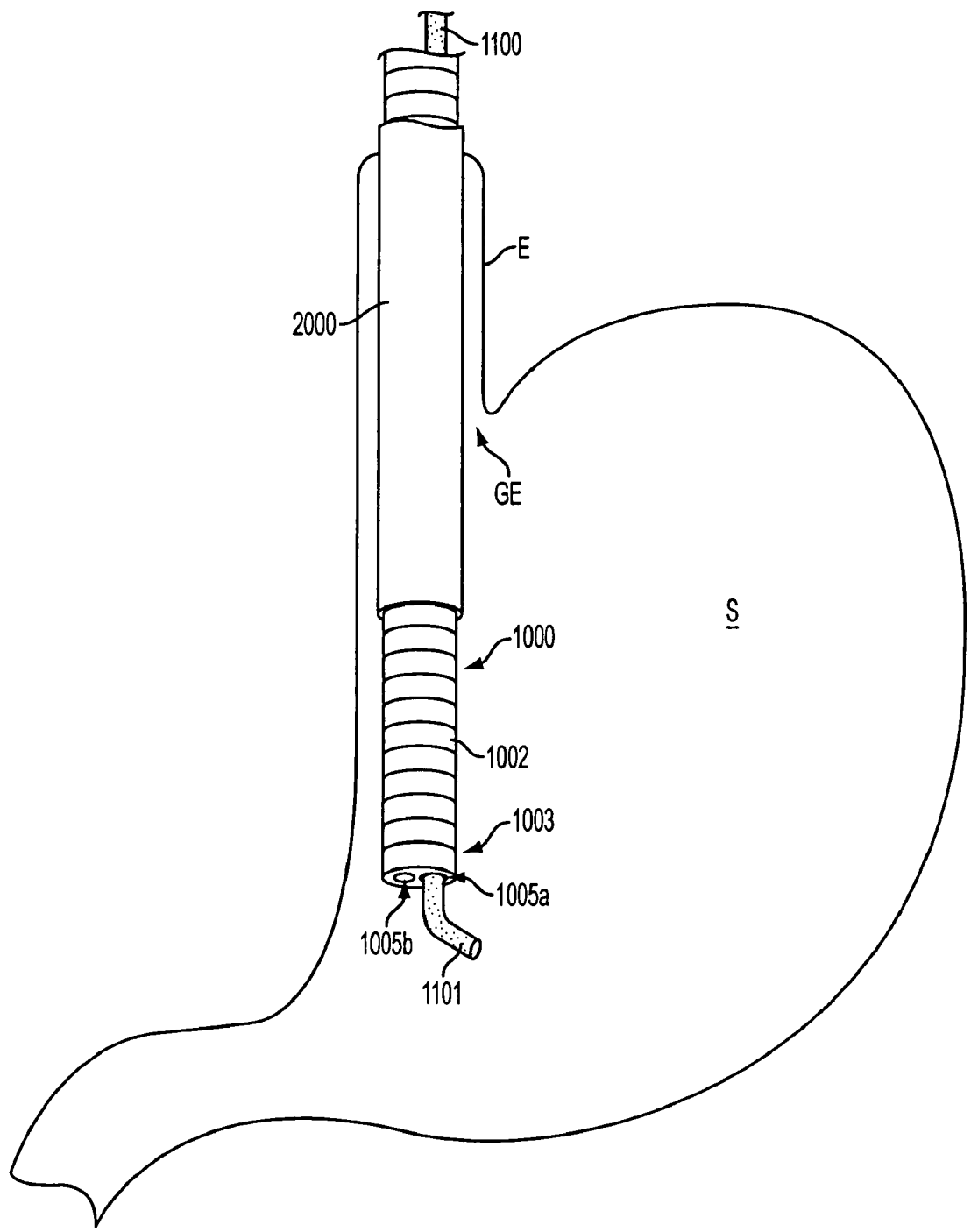
FIGS. 40A-40D are side-views, partially in section, illustrating an exemplary method of performing endoluminal gastric reduction with a system of tools illustratively comprising the shape-lockable apparatus of FIGS. 35-39, the plication apparatus of FIGS. 1-3, the anchor assembly of FIG. 7, the anchor delivery system of FIG. 21 and a commercially available gastroscope.
Figure 40B:
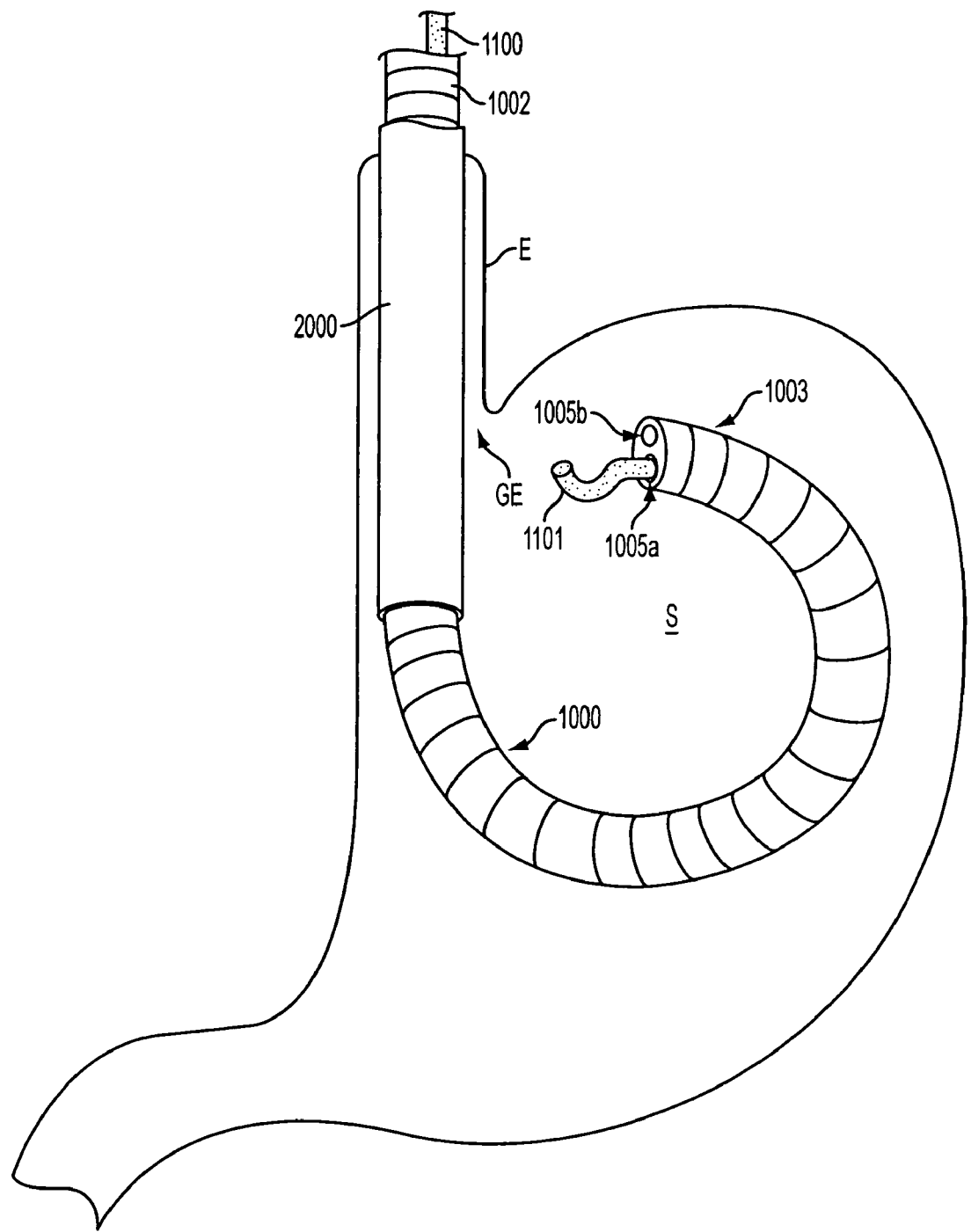
Figure 40C:
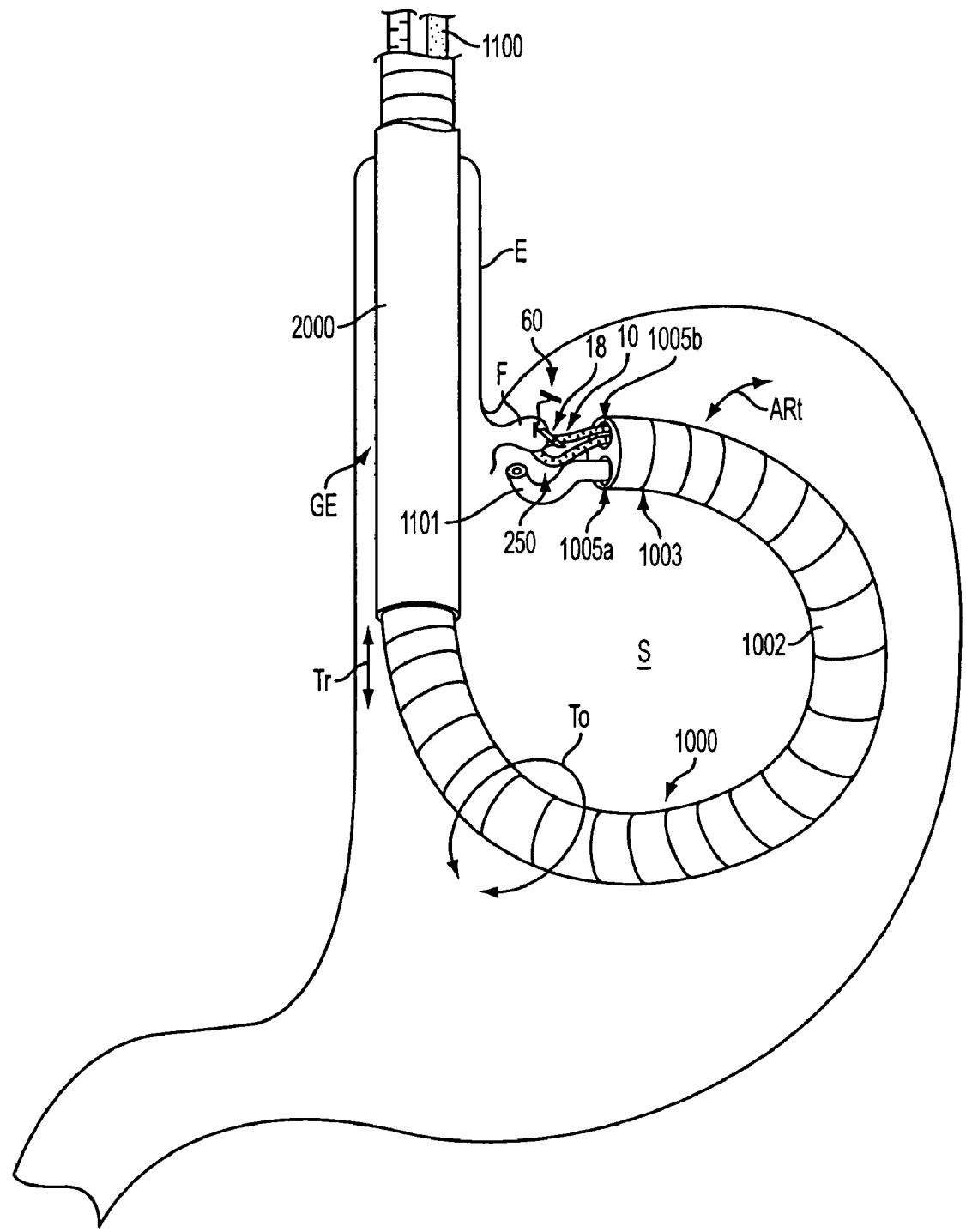
Figure 40D:
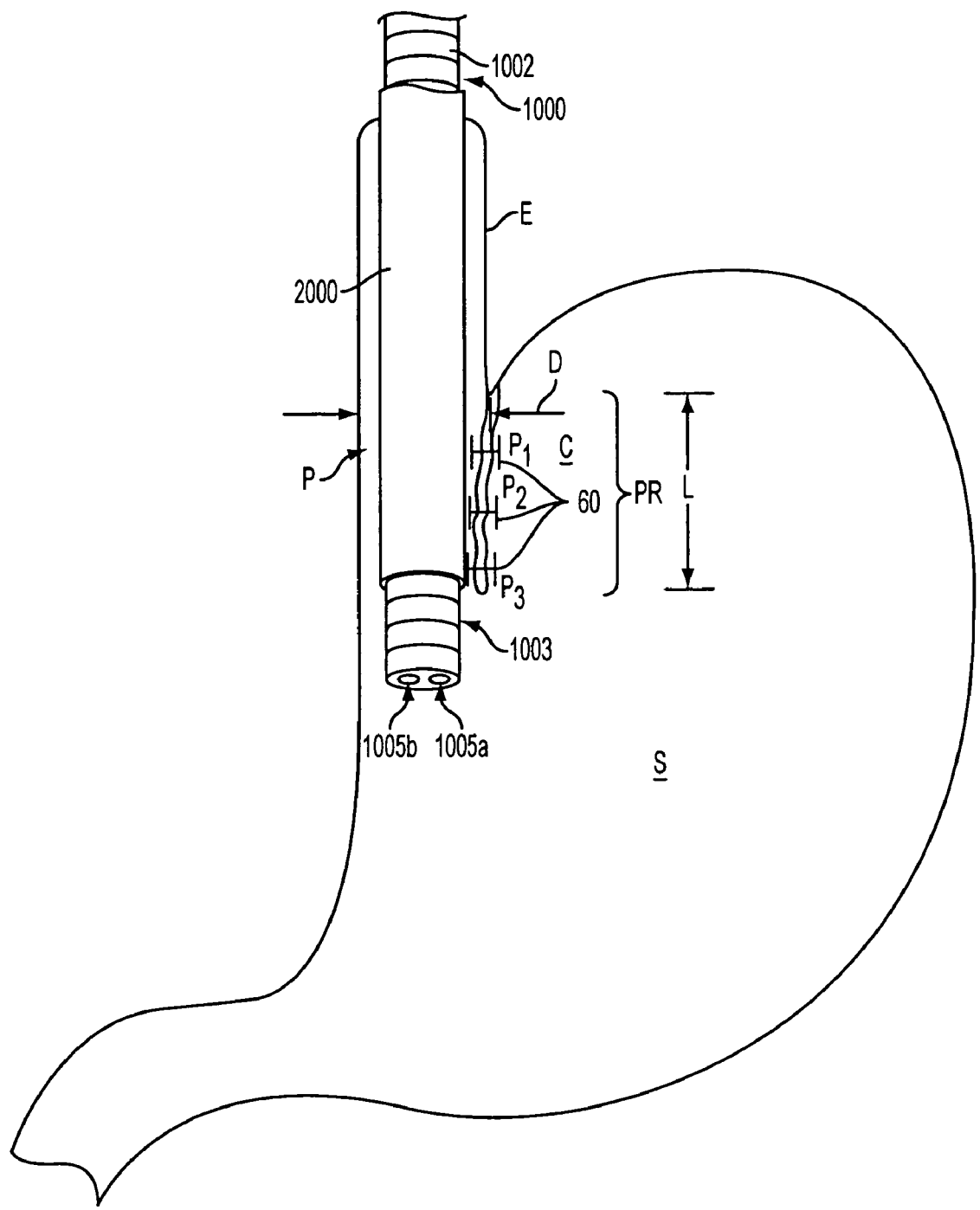
Figure 41A:
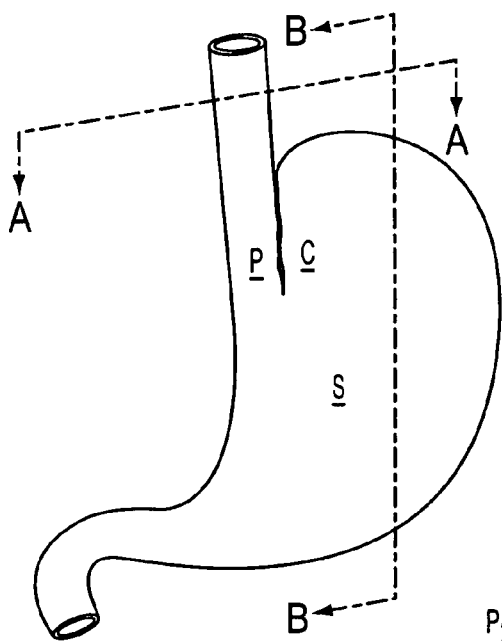
FIGS. 41A-41C are, respectively, an isometric view of a patient's stomach after performing endoluminal gastric reduction using the methods of FIG. 40; a cross-sectional view of the same along plane A—A in FIG. 41A; and a cross-sectional view of the stomach along plane B—B in FIG. 41A, prior to approximation of the pluralities of tissue folds to achieve the gastric reduction.

With reference now to FIG. 40, in conjunction with FIG. 41, a method of performing endoluminal gastric reduction is described utilizing a system of tools illustratively comprising commercially available gastroscope 1100, plication apparatus 10 of FIGS. 1-3, anchor delivery system 250 of FIG. 21 loaded with anchor assembly 60 of FIG. 7, and shape-lockable apparatus 1000 of FIGS. 35-39. Gastric reduction is a technique for reducing a patient's appetite and/or ability to ingest food by reducing a volume of the stomach through which food may pass. Endoluminal gastric reduction in accordance with the present invention entails partitioning the stomach into first and second chambers, and more specifically into a small lumen or pouch and a larger chamber, over at least a portion of the stomach.

The lumen/pouch preferably has a volume of approximately 10-50 cm$^3$, and even more preferably a volume of approximately 15 cm$^3$, and is positioned near and inferior to the patient's gastroesophageal junction. Ingested food may only pass through the small lumen over the partitioned portion of the stomach. The lumen preferably is formed by approximating opposing anterior and posterior segments of the patient's stomach wall over a length or arc of the wall near and inferior to the gastroesophageal junction.

As illustrated in FIGS. 40 and 41, endoscopic gastric reduction may be achieved by endoscopically forming, approximating and securing a plurality of tissue folds in a first plane within a patient's stomach, then endoscopically forming, approximating and securing at least one additional plurality of tissue folds in at least one substantially parallel plane within the patient's stomach. The first plurality of tissue folds and the at least one additional plurality of tissue folds may be attached or detached from one another. Each plurality of folds preferably comprises one or more tissue folds from opposing anterior and posterior segments of the stomach near and inferior to the gastroesophageal junction.

More, specifically, endoscopic gastric reduction may be achieved by advancing an overtube through a patient's esophagus into the patient's stomach while the overtube is disposed in a flexible state, then transitioning the overtube to a rigid state in a desired orientation within the patient's stomach. A plication device, either coupled to the overtube or advanced therethrough, may then be used to form the plurality of tissue folds, while an anchor delivery system may be used to approximate and/or secure the tissue folds, thereby partitioning the patient's stomach.

In FIG. 40, overtube 1002 of shape-lockable apparatus 1000 illustratively comprises first and second lumens 1005$a$ and 1005$b$ for passage of gastroscope 1100 and plication apparatus 10/anchor delivery system 250, respectively. In FIG. 40A, optional thin wall sheath 2000 is disposed within a patient's gastrointestinal lumen through the patient's mouth, into esophagus E, past the gastroesophageal junction GE, and into the patient's stomach S. Shape-lockable overtube 1002 of apparatus 1000 is advanced through sheath 2000 into stomach S while disposed in the flexible state. Sheath 2000 provides a barrier between overtube 1002 and esophagus E, which may facilitate increased maneuverability of apparatus 1000 by protecting the esophagus during optional torqueing, translation and/or articulation of overtube 1002.

In FIG. 40A, gastroscope 1100 illustratively has been advanced through lumen 1005$a$ of overtube 1002 past distal region 1003 while the overtube is disposed in the flexible state. As will be apparent to those of skill in the art, a visualization element alternatively or additionally may be coupled to overtube 1002; multiple point visualization may facilitate complex procedures and/or enable triangulation for deployment of anchor assemblies across tissue folds. Furthermore, plication apparatus 10 and anchor delivery system 250 optionally may be coupled to the overtube or may be advanced through the overtube while the tube is disposed in the flexible state.

In FIG. 40B, overtube 1002 is articulated to an orientation whereby distal region 1003 facilitates engagement of tissue near and inferior to the patient's gastroesophageal junction GE. Such articulation may be achieved, for example, by actuating steerable distal tip 1101 of gastroscope 1100. Alternatively, apparatus 1000 may comprise steering features. As yet another alternative, a steering tool, such as a shaped wire, may be advanced through second lumen 1005$b$ to properly orient the overtube. Furtherstill, the overtube may comprise a preformed flexible shape whereby the overtube assumes an arcuate configuration, and a rigid wire may be reversibly disposed with second lumen 1005$b$ of overtube 1002 in order to straighten the overtube during insertion through esophagus E; upon positioning of distal region 1003 of apparatus 1000 within stomach S, the wire may be removed from the lumen, such that overtube 1002 re-assumes its pre-formed shape. As yet another alternative, plication apparatus 10 and/or anchor delivery system 250 may comprise steering features and may be advanced through the second lumen to steer the overtube into position.

With apparatus 1000 disposed in the desired configuration or orientation, the apparatus is reversibly shape-locked to a rigid state as described previously, such that the apparatus maintains its position within the stomach. Preferably, the articulated portion of apparatus 1000 traverses an arc of substantially continuous radius of curvature in the shape-locked configuration, thereby reducing a magnitude of forces required to advance and retract instruments through overtube 1002. In a preferred embodiment, the arc traverses approximately 270° and has a radius of curvature between about 5 and 10 cm, and, even more preferably, approximately 7-8 cm. By retroflexing about 270°, distal region 1003 of apparatus 1000 is directed back towards the body of overtube 1002 near and inferior to gastroesophageal junction GE.

Plication apparatus 10 and anchor delivery system 250 are advanced through second lumen 1005$b$ of overtube 1002 distal of distal region 1003 (alternatively, the plication apparatus and anchor delivery system may be coupled to the overtube). As seen in FIG. 40C, e.g. under visualization provided by gastroscope 1100, tissue is engaged within stomach S using tissue grabbing assembly 18. Tissue fold F is formed, for example, as described previously with respect to FIG. 3. Anchor assembly 60 then is deployed across the tissue fold via anchor delivery system 250 and is adjusted to secure the fold, for example, as described hereinabove with respect to FIG. 21.

Figure 41C:
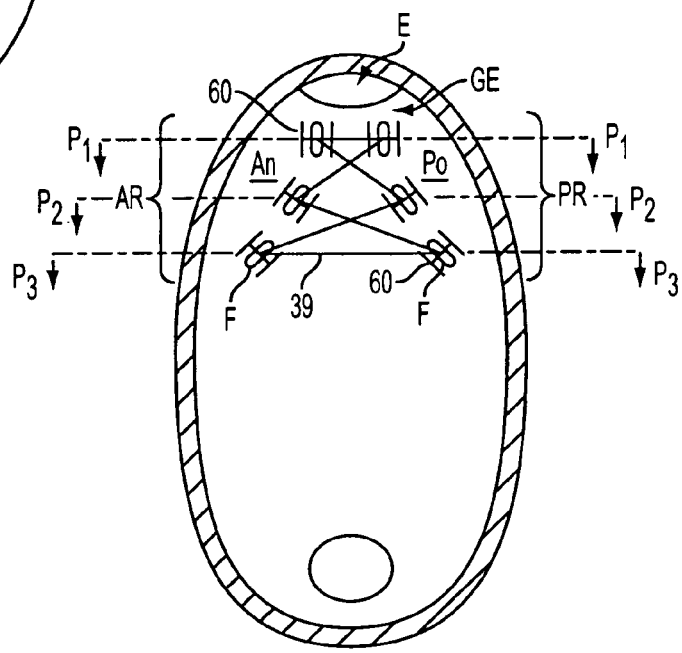
Figure 41B:
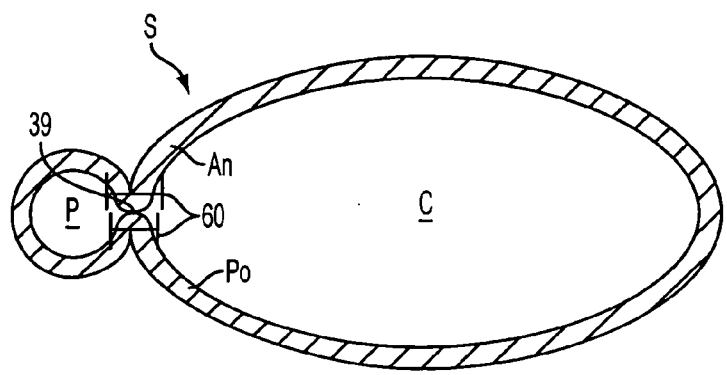

As discussed previously and seen in FIG. 41, in order to achieve endoluminal gastric reduction, opposing anterior An and posterior Po surfaces of stomach S are drawn together to partition the stomach into first lumen or pouch P and second larger chamber C. As seen in FIG. 41C, in order to achieve such partitioning, a plurality of folds is formed on the opposing surfaces in a first plane $P_1$. The opposing folds are connected by suture 39 or by other means and are approximated, for example, by reducing a length of suture disposed between the opposing surfaces, to partition the stomach as in FIG. 41B.

Optionally, at least one additional plurality of folds may be formed on the opposing anterior An and posterior Po surfaces in at least one additional plane that is substantially parallel to first plane $P_1$. FIGS. 40D and 41C comprise optional additional pluralities of tissue folds in second and third planes $P_2$ and $P_3$. In effect, an anterior ridge AR of tissue folds is formed, and an opposing posterior ridge PR of tissue folds is formed. These additional pluralities of tissue folds may be attached to the first plurality of tissue folds, as in FIG. 41C, or may be unattached. Upon approximation of the tissue folds, for example, via cinching of suture 39, pouch P is formed, and endoluminal gastric reduction is achieved.

The number of planes in which pluralities of tissue folds are formed may be specified based on a preferred longitudinal spacing of anchor assemblies and/or based upon a desired length of pouch P. The desired length L may be specified based on a desired volume V of pouch P and a diameter D of pouch P, according to the following equation:

$$L = 4V/(\pi D^2) \quad (1)$$

For example, overtube 1002 preferably has an outer diameter of approximately 1.6 cm. Thus, the diameter of pouch P must be at least 1.6 cm, so that the overtube may pass through the pouch. Assuming a pouch diameter of approximately 1.6 cm, and in order to provide the pouch with a volume of about 15 cm$^3$, a length of pouch P should be about 7.5 cm.

Referring again to FIG. 40C, in order to form, secure and approximate tissue folds on opposing anterior An and posterior. Po surfaces of stomach S, as well as in multiple planes $P_x$, overtube 1002 preferably comprises multiple degrees of freedom. Arrows in FIG. 40C describe illustrative directions in which apparatus 1000 may be maneuvered to re-orient or reconfigure overtube 1002. Specifically, apparatus 1000 may be translated relative to esophagus E and sheath 2000, as described by arrow Tr. Furthermore, apparatus 1000 may be torqued, as described by arrow To. Furtherstill, the apparatus may be articulated, as described by arrow ARt. As will be apparent, additional or alternative degrees of freedom optionally may be provided.

As an example, a medical practitioner translating or torqueing handle 1001 of apparatus 1000 from external to the patient may achieve translation and torqueing of overtube 1002. Articulation may be achieved by a number of means, such as steering features provided within overtube 1002, e.g. a tensioning wire, or by temporarily returning overtube 1002 to the flexible state, actuating steerable end 1101 of gastroscope 1100 to articulate overtube 1002 to a desired configuration, then once again shape-locking overtube 1002 to the rigid state. Combinations of torqueing, translation and articulation may be used to position overtube 1002 in any desired configuration.

In FIG. 40D, by repositioning overtube 1002, re-loading anchor delivery system 250, and re-actuating plication apparatus 10 and anchor delivery system 250, tissue folds have been formed, secured and approximated on opposing surfaces in multiple planes, thereby forming pouch P and chamber C within stomach S. Overtube 1002 has been transitioned back to the flexible state, and all instruments advanced through the overtube have been removed from apparatus 1000. Overtube 1002 and optional sheath 2000 now may be removed from stomach S and esophagus E through pouch P, thereby completing endoluminal gastric reduction.

Figure 42A:
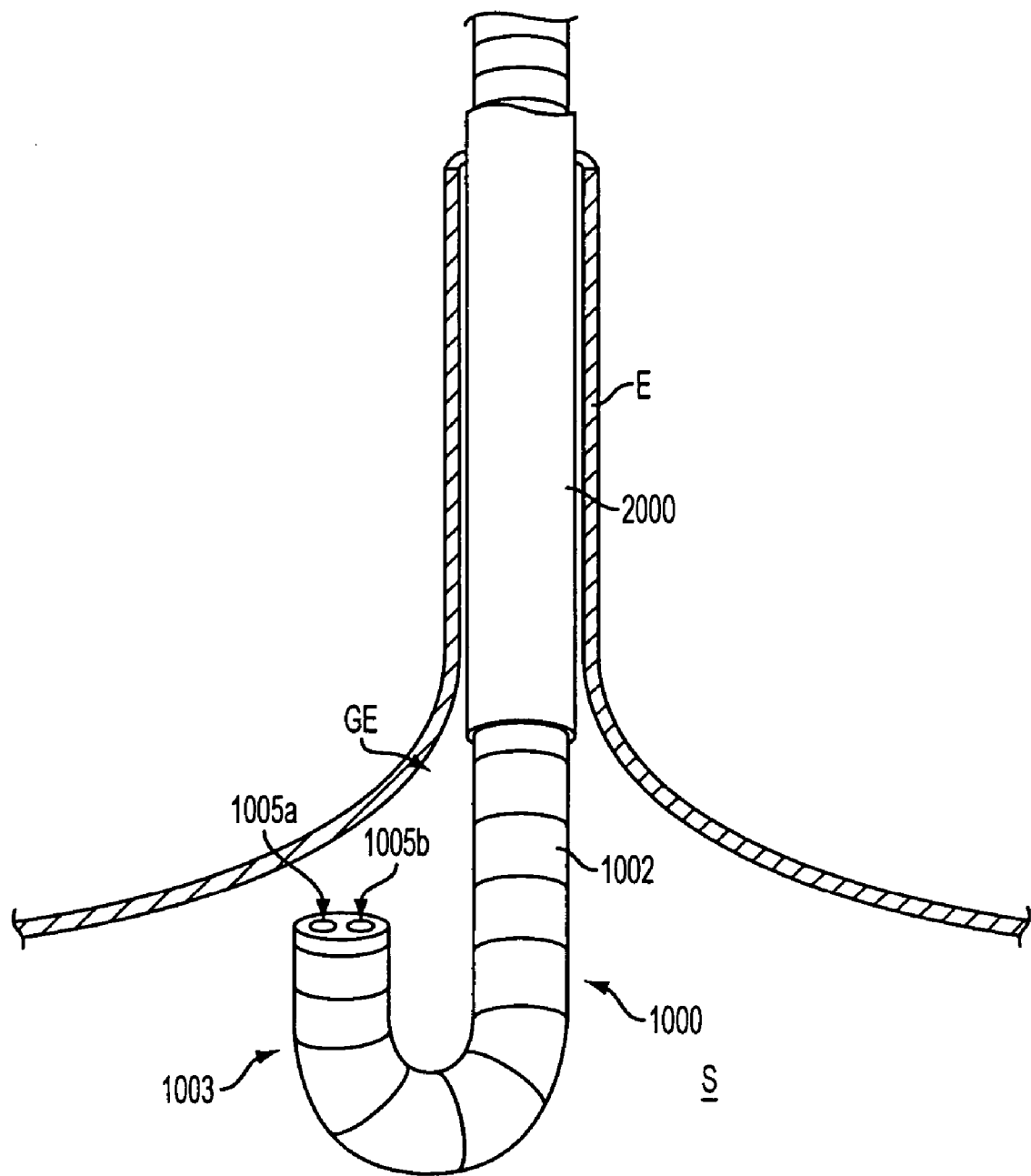
FIGS. 42A-42C are side-views, partially in section, illustrating an exemplary method of treating gastroesophageal reflux disease with the illustrative system of tools described with respect to FIG. 40.

With reference now to FIG. 42, a method of treating gastroesophageal reflux disease ("GERD") using the system of tools described with respect to FIG. 40 is provided. Apparatus 1000 is advanced through a patient's esophagus E with overtube 1002 disposed in a flexible state. Once again, optional sheath 2000 may be provided between esophagus E and apparatus 1000. The apparatus is then manipulated, for example, as described hereinabove, into a configuration enabling access to tissue in a vicinity of the patient's gastroesophageal junction GE. Overtube 1002 is then shape-locked to a rigid state, as seen in FIG. 42A.

Figure 42B:
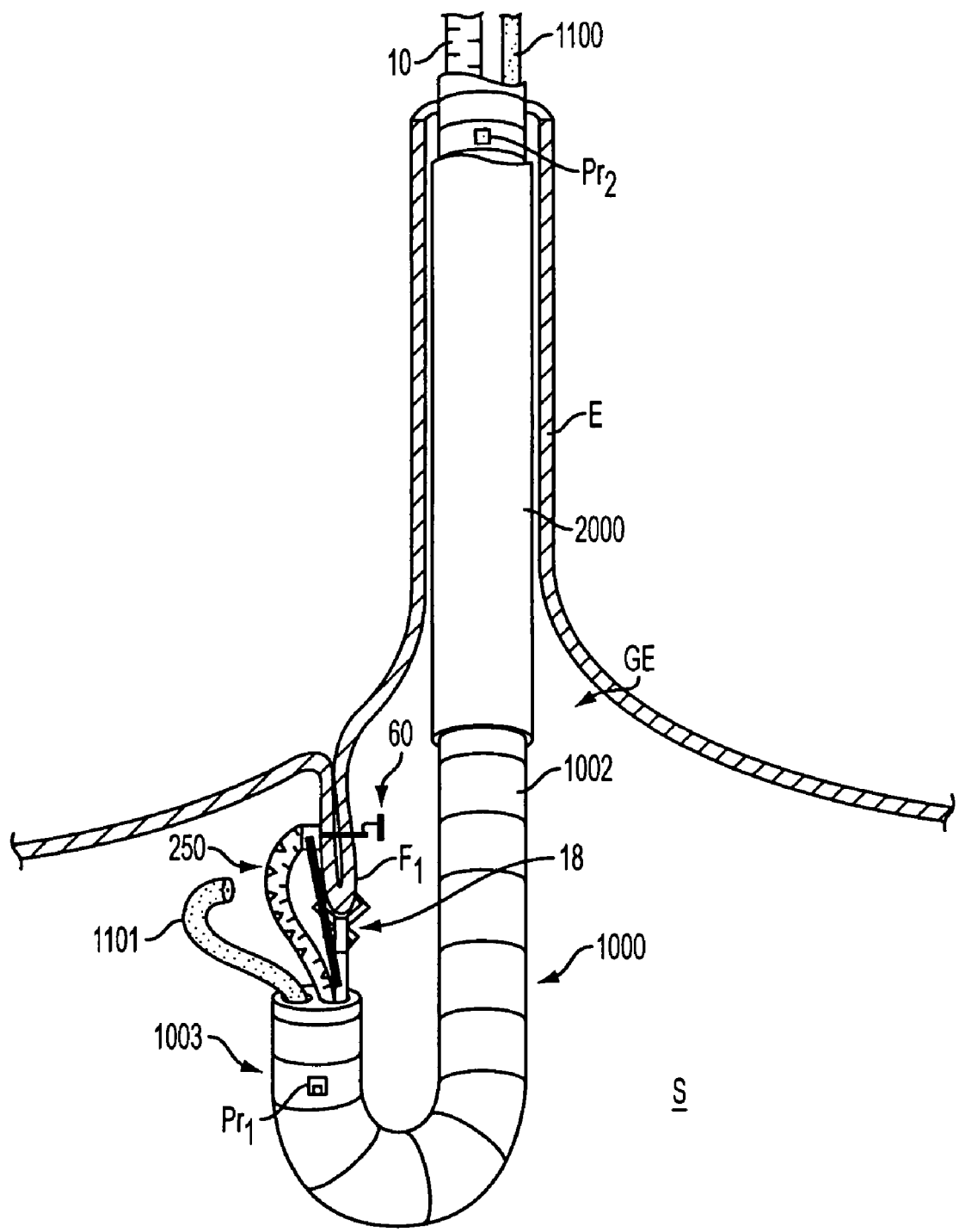
Figure 42C:
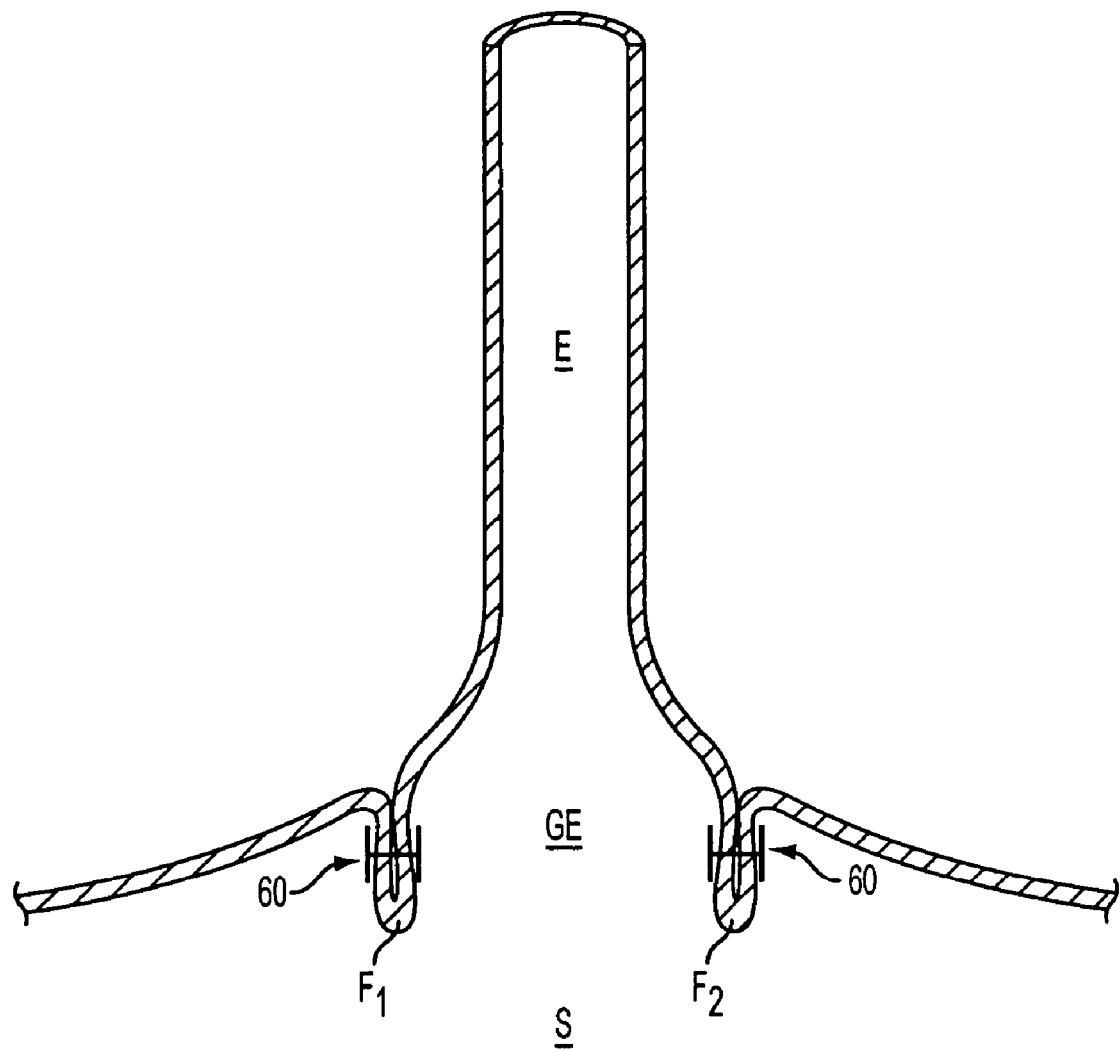

In FIG. 42B, plication apparatus 10 (either advanced through or coupled to apparatus 1000) is used to form tissue fold $F_1$ on a first side of gastroesophageal junction GE. Anchor assembly 60, which is deployed and adjusted via anchor delivery system 250, secures the tissue fold. Visualization of the procedure is achieved, for example, via gastroscope 1100.

Tissue fold $F_1$ provides a flap that reduces reflux of acid or other stomach materials into esophagus E. In patients with more serious conditions, it may be necessary to provide one or more additional folds around gastroesophageal junction GE. For example, apparatus 1000 may be repositioned, anchor delivery system 250 reloaded, and opposing fold $F_2$ formed, as in FIG. 42C. After a desired pressure differential has been established across gastroesophageal junction GE, overtube 1002 may be returned to the flexible state, and apparatus 1000, as well as any instruments advanced therethrough or coupled thereto, may be removed from the patient, thereby providing endoluminal treatment of gastroesophageal reflux disease. Optionally, first and second pressure sensors $Pr_1$ and $Pr_2$ may be provided along the length of apparatus 1000 to measure the pressure differential across gastroesophageal junction GE, as seen in FIG. 42B. In use, first pressure sensor $Pr_1$ may be positioned distal of the junction within the patient's stomach S, while second pressure sensor $Pr_2$ is disposed proximal of the junction within the patient's esophagus E. Additional or alternative sensors will be apparent to those of skill in the art.

With reference now to FIG. 43, an alternative method for achieving endoluminal gastric reduction or remodeling is described. Inamed Corporation of Santa Barbara, Calif., markets the BioEnterics® LAP-BAND® System, which consists of an inflatable silicone band that is laparascopically placed within a patient's abdomen. The band is fastened around the upper stomach, giving the stomach an hourglass profile and creating a tiny stomach pouch that limits and controls an amount of food the patient can ingest. It also creates a small outlet that slows the emptying process into the stomach and the intestines. According to the company's website, patients using the system experience an earlier sensation of fullness and are satisfied with smaller amounts of food, which results in weight loss.

A significant drawback of the BioEnterics® LAP-BAND® System is that a laparascopic incision must be made within the patient's abdomen in order to place the device. Applicant's co-pending U.S. patent application Ser. No. 10/288, 619, which is incorporated herein by reference in its entirety, and from which the present application claims priority, describes endoluminal methods and apparatus for providing the stomach with an hourglass profile to facilitate weight loss, thereby mitigating a need for laparascopic incisions. In FIG. 43, a system of tools of the present invention is used to endoluminally achieve such gastric reduction or remodeling via plicated tissue folds. In the method of FIG. 43, only suture is disposed on the exterior of the stomach post-reduction/remodeling.

Figure 43B:
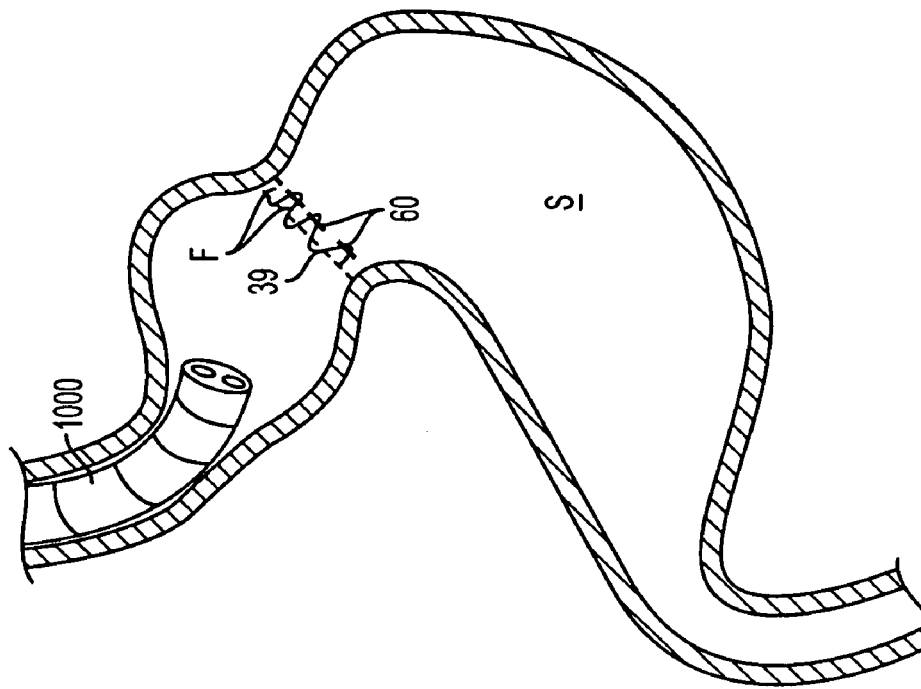
FIGS. 43A and 43B are side-views, partially in section, illustrating an alternative method of performing endoluminal gastric reduction utilizing a system of tools of the present invention.
Figure 43A:
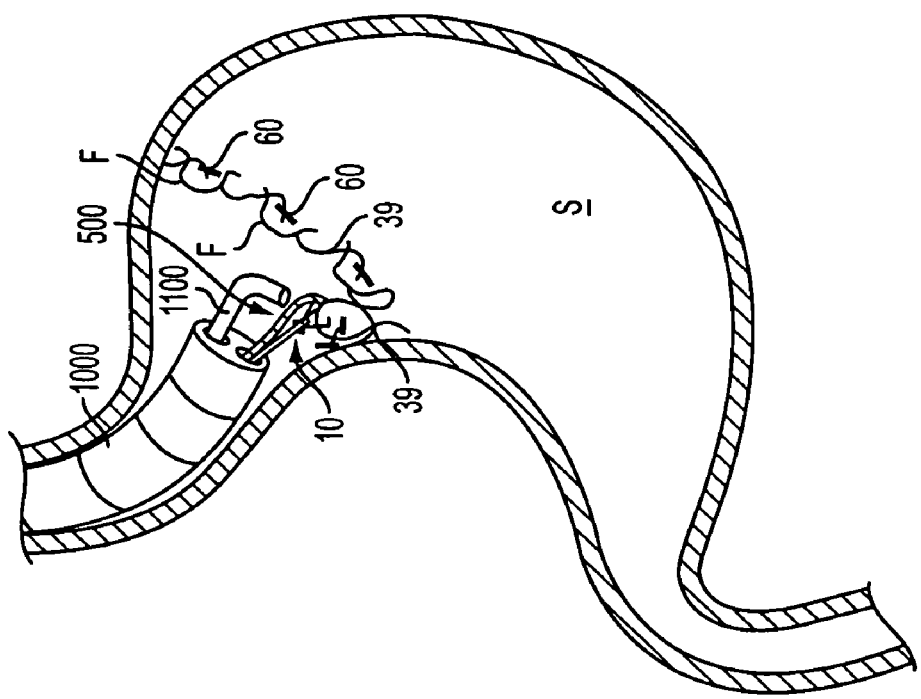

In FIG. 43A, a plurality of tissue folds F have been formed around the circumference of stomach S within an upper portion of the stomach via a system of tools comprising plication apparatus 10, a plurality of anchor assemblies 60 interconnected by suture 39, multi-fire anchor delivery system 500, shape-lockable apparatus 1000 and gastroscope 1100. In FIG. 43B, the interconnected anchor assemblies have been cinched together, thereby approximating the plurality of tissue folds F, and endoluminally providing stomach S with an hourglass profile. The system of tools may then be removed from the patient, thereby completing endoluminal reduction or remodeling of stomach S.

In FIGS. 40-42, as an alternative to using anchor delivery system 250 of FIG. 21, a multi-fire anchor delivery system, such as anchor delivery system 500, 500' or 600 of FIGS. 25-27 (loaded, for example, with multiple anchor assemblies 60 of FIG. 7), may be used so as to omit a need to remove and reload all or a portion of the anchor delivery system from the patient's GI lumen in order to deploy and secure multiple anchor assemblies across one or more tissue folds. Furthermore, although the methods of FIGS. 40-43 have illustratively been described with reference to a system of tools comprising plication apparatus 10, anchor assembly 60, anchor delivery system 250 (delivery system 500 in FIG. 43), shape-lockable apparatus 1000 and gastroscope 1100, any combination of diagnostic or therapeutic tools/instruments in accordance with the present invention may be utilized, including, for example, alternative plication apparatus, anchor assemblies, anchor delivery systems and shape-lockable apparatus described previously. Furtherstill, although the visualization element described in FIGS. 40-43 comprises an endoscope or gastroscope, it should be understood that any other alternative or additional methods or apparatus for visualizing a medical procedure may be provided, including, but not limited to, magnetic resonance imaging, ultrasound imaging, optical coherence tomography imaging, fluoroscopic imaging, and combinations thereof. Also, although the system of tools have illustratively been described as advanced through shape-lockable apparatus 1000, it should be understood that any or all of the tools alternatively or additionally may be coupled to apparatus 1000, for example, to distal region 1003 of apparatus 1000.

FIGS. 40-43 have presented methods of using apparatus of the present invention to perform endoluminal gastric reduction and treatment of GERD. Alternative methods for performing these medical procedures using apparatus of the present invention will be apparent to those of skill in the art. For example, U.S. Pat. No. 6,540,789 to Silvermann et al., which is incorporated herein by reference, describes a method for performing gastric reduction by injecting bulking agents into a patient's stomach at a plurality of locations, thereby reducing a volume of the stomach. Apparatus of the present invention may be used to reduce the volume of a patient's stomach by forming a plurality of secured tissue folds within the stomach. The tissue folds may be formed, for example, at a plurality of randomly selected locations. Alternatively, apparatus of the present invention may be used to perform gastric reduction via placement and/or sizing of an implantable stoma within the stomach. As yet another example, marking devices may be provided with apparatus of the present invention in order to map out locations for formation of tissue folds, e.g., to achieve gastric reduction. Additional methods will be apparent.

Apparatus of the present invention should in no way be construed as limited to treatment of GERD or morbid obesity. Rather, a variety of other medical procedures—both diagnostic and therapeutic, or a combination thereof—may be performed within a patient's gastrointestinal lumen or other body cavities or organs, including hollow, tortuous and/or unpredictably supported body cavities, using tools and instruments of the present invention. These include, but are not limited to, endoscopic retrograde cholangiopancreatography ("ERCP"), intubation of the bile duct, upper or lower gastrointestinal endoscopy, colonoscopy, flexible sigmoidoscopy, esophageal dilatation, anastomosis, liver biopsy, esophageal manometry, esophageal pH, cholecystectomy, enteroscopy, resection of lesions or early cancers, treatment of bleeding sites, trans-esophageal microsurgery, trans-anal microsurgery, and combinations thereof. Additional procedures will be apparent to those of skill in the art.

Figure 44:
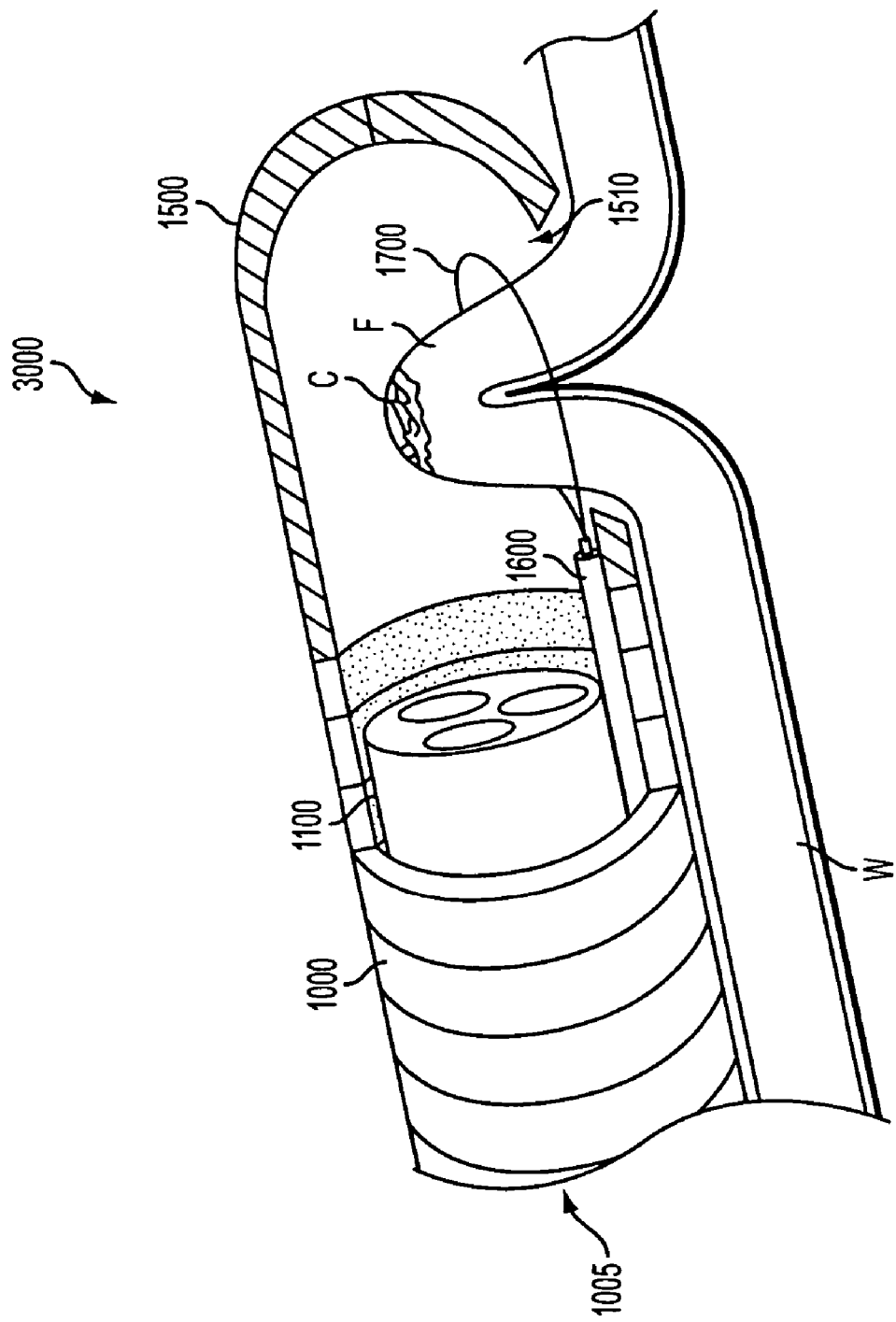
FIG. 44 is a side view, partially in section, illustrating a method of resecting a lesion or early cancer utilizing a system of tools of the present invention illustratively comprising a suction plicator and a resection loop.

With reference to FIG. 44, an exemplary method of resecting a lesion or early cancer, e.g. within a patient's gastrointestinal tract, using apparatus of the present invention is described. In FIG. 44, system of tools 3000 comprises shape-lockable overtube 1000 having suction plicator 1500 coupled to its distal end. System 3000 further comprises endoscope 1100 and tool delivery tube 1600 disposed within lumen 1005 of overtube 1000. Tool delivery tube 1600 optionally may comprise delivery tube 252 of anchor delivery system 250, as described hereinbelow with respect to FIG. 45, or may comprise the delivery tube of any alternative anchor delivery system described previously. Furthermore, tube 1600 may be coupled to overtube 1000 or may advanceable relative to the overtube.

Suction plicator 1500 comprises side aperture 1510 to facilitate side-suction plication of tissue. Plicator 1500 additionally or alternatively may comprise one or more apertures at its distal end (not shown) to facilitate end-suction plication of tissue. Plicator 1500 and overtube 1000 preferably are sealed along their lengths, such that suction may be drawn through the overtube and plicator, e.g., via a suction pump (not shown) coupled to a proximal region of overtube 1000 external to the patient.

Advantageously, as compared to previously-known suction plication apparatus, shape-lockable overtube 1000 allows system of tools 3000 to be positioned at a treatment site while the overtube is disposed in a flexible state. Overtube 1000 then optionally may be transitioned to a rigid state prior to drawing of suction through plicator 1500. In this manner, system 3000 may be directed to, and maintained at, a treatment site during a medical procedure.

In FIG. 44, shape-lockable overtube 1000 has been endoscopically advanced, e.g., through a patient's esophagus or colon, under endoscopic visualization provided by endoscope 1100, to a vicinity of lesion or early cancer C along tissue wall W, while the overtube was disposed in a flexible state. Overtube 1000 alternatively may be advanced laparascopically, e.g. through a trocar. The overtube preferably is then transitioned to a rigid state in a configuration enabling access, e.g. luminal access, to the lesion or early cancer.

Suction is drawn through overtube 1000 and suction plicator 1500 to urge tissue in the vicinity of lesion/early cancer C through side aperture 1510 and into lumen 1005 of overtube 1000, thereby forming tissue fold F. As can be verified by endbscopic visualization, lesion or cancer C resides on the folded tissue. The lesion, polyp, cancer, etc. then may be removed via cutting apparatus, such as snare or resection loop 1700 advanced through tool delivery tube 1600. As will be apparent to those of skill in the art, alternative plication apparatus in accordance with the present invention may be used to resect lesion C.

Figure 45:
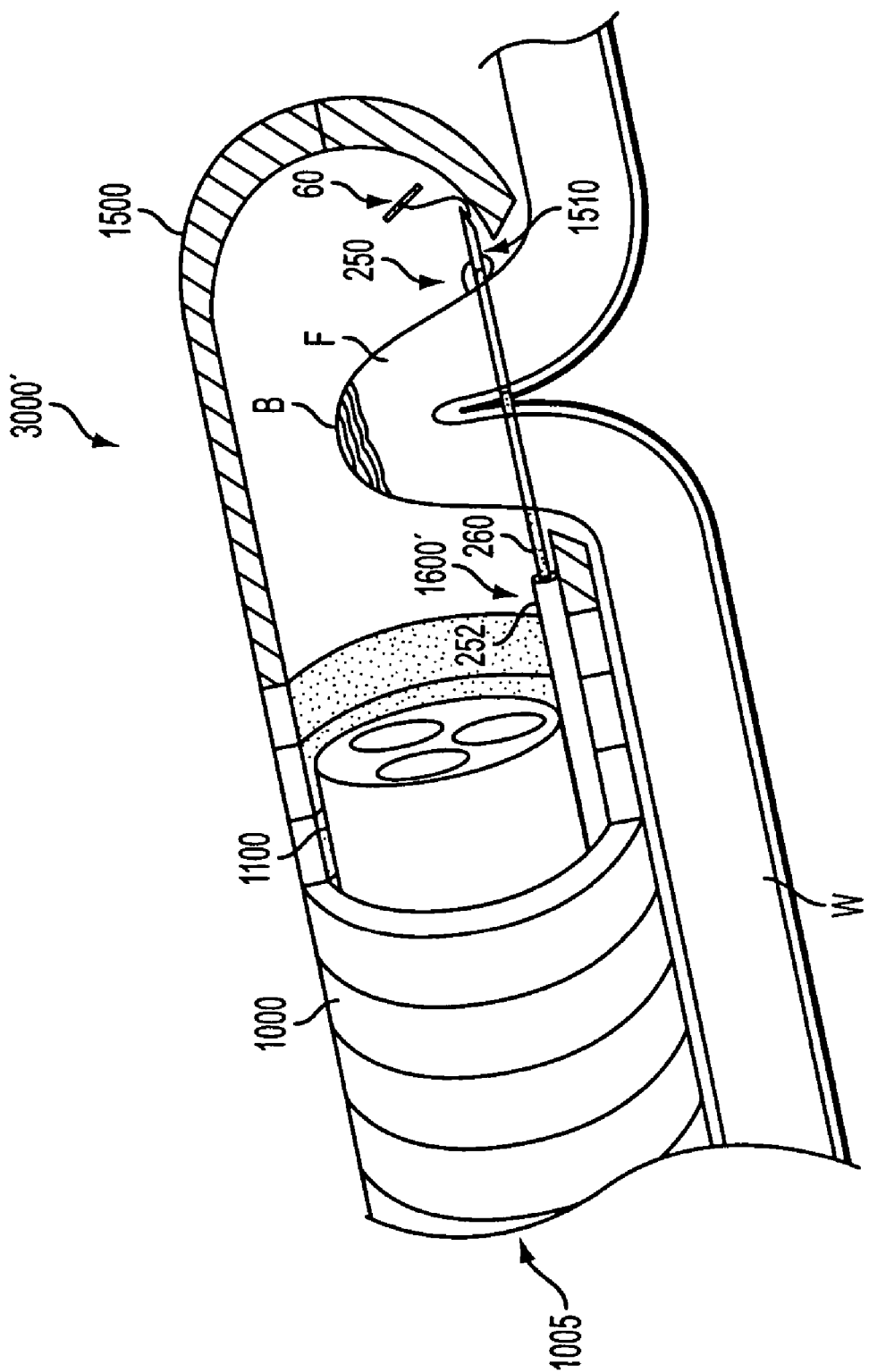
FIG. 45 is a side view, partially in section, illustrating a method of treating a bleeding site utilizing a system of tools of the present invention.

With reference now to FIG. 45, an exemplary method for endoscopically treating a bleeding site, e.g. within a patient's gastrointestinal tract, is described. In FIG. 45, system of tools 3000' is substantially the same as system 3000 of FIG. 44, except that tool delivery tube 1600' illustratively comprises delivery tube 252 of anchor delivery system of 250, and resection loop 1700 illustratively has been replaced with anchor delivery system 250 and anchor assembly 60 for securing tissue folds drawn through side-aperture 1510 of suction plicator 1500. System 3000' has been positioned, and tissue fold F has been formed, utilizing the techniques described hereinabove with respect to FIG. 44, such that bleeding site B resides on folded tissue F. Anchor delivery system 250 having needle 260 is then actuated in the manner described previously to deploy and adjust anchor assembly 60 and secure tissue fold F, thereby sealing and precluding additional bleeding from bleeding site B.

As will be apparent to those of skill in the art, alternative plication apparatus and/or anchor delivery systems in accordance with the present invention may be used to treat bleeding site B. Furthermore, although tool systems 3000 and 3000' of FIGS. 44 and 45, respectively, have illustratively been described for use in resecting lesions and/or treating bleeding sites, these systems alternatively or additionally may be used for any other applicable medical procedure, including, but not limited to, those described previously, such as gastric reduction and treatment of gastroesophageal reflux disease.

Although preferred illustrative embodiments of the present invention are described hereinabove, it will be apparent to those skilled in the art that various changes and modifications may be made thereto without departing from the invention. It is intended in the appended claims to cover all such changes and modifications that fall within the true spirit and scope of the invention.

What is claimed is:

1. A method for performing a medical procedure within a hollow body organ of tortuous or unpredictably supported anatomy, the method comprising:
   advancing an overtube comprising a plurality of nested elements having mating contoured surfaces within the hollow body organ in a flexible state;
   transitioning the overtube to a rigid state by imposing a load that clamps the contoured surfaces of adjacent nested elements together to thereby substantially fix the shape of the overtube in any desired configuration;
   advancing a plication device through a lumen defined by the overtube after the overtube has been transitioned to the rigid state, the plication device comprising a pair of movable jaws adapted to engage tissue within the hollow body organ;
   forming a tissue fold within the hollow body organ with the plication device; and
   securing the tissue fold using a tissue anchor deployed from a needle of the plication device.

2. The method of claim 1 further comprising visualizing formation of the tissue fold.

3. The method of claim 2, wherein visualizing formation of the tissue fold further comprises visualizing formation with a visualization element advanced through the overtube.

4. The method of claim 2, wherein visualizing formation of the tissue fold further comprises visualizing formation with a visualization element coupled to the overtube.

5. The method of claim 1, wherein the medical procedure comprises endoscopically treating gastroesophageal reflux disease, advancing the overtube within a hollow body organ comprises advancing the overtube through a patient's esophagus and into the patient's stomach, transitioning the overtube to a rigid state comprises transitioning the overtube to a rigid state in a configuration enabling access to the patient's gastroesophageal junction, and forming a tissue fold comprises forming at least one tissue fold in a vicinity of the patient's gastroesophageal junction.

6. The method of claim 1, wherein the medical procedure comprises endoscopically performing gastric reduction, advancing the overtube within a hollow body organ comprises advancing an overtube through a patient's esophagus and into the patient's stomach, transitioning the overtube to a rigid state comprises transitioning the overtube to a rigid state in a desired configuration within the patient's stomach, and forming a tissue fold comprises forming a plurality of tissue folds within the patient's stomach.

7. The method of claim 6 further comprising approximating and securing the plurality of tissue folds, thereby partitioning the patient's stomach into at least first and second chambers over at least a portion of the stomach.

8. The method of claim 7, wherein forming, approximating and securing a plurality of tissue folds further comprises: forming, approximating and securing a first plurality of tissue folds in a first plane; and forming, approximating and securing at least one additional plurality of tissue folds in at least one additional plane, wherein the first plane and the at least one additional plane are substantially parallel to one another.

9. The method of claim 7, wherein partitioning the stomach into first and second chambers further comprises partitioning the stomach into a first lumen and a second chamber.

10. The method of claim 9, wherein partitioning the stomach into a first lumen and a second chamber further comprises partitioning the stomach such that the patient's gastroesophageal junction only communicates with the first lumen.

11. The method of claim 10, wherein partitioning the stomach into a first lumen comprises partitioning the stomach into a first lumen having a volume in the range of 10-50 $cm^3$.

12. The method of claim 6, wherein forming a plurality of tissue folds further comprises forming a plurality of tissue folds inferior to the patient's gastroesophageal junction.

13. The method of claim 12, wherein forming a plurality of tissue folds further comprises forming a plurality of tissue folds having at least one tissue fold from an anterior segment of the patient's stomach and at least one tissue fold from an opposing posterior segment of the patient's stomach.

14. The method of claim 6, wherein forming a plurality of tissue folds within a patient's stomach comprises forming and securing a plurality of tissue folds disposed at substantially randomly selected locations to reduce a volume of the stomach.

15. The method of claim 6, wherein forming a plurality of tissue folds within a patient's stomach comprises forming a plurality of interconnected tissue folds around a perimeter of the patient's stomach with instruments advanced through, or coupled to, the overtube, the method further comprising approximating the plurality of interconnected tissue folds to remodel the stomach to an hourglass profile.

16. The method of claim 1, wherein the medical procedure comprises resecting a lesion or cancer within a patient's gastrointestinal tract, advancing the overtube within a hollow body organ comprises advancing the overtube through the patient's esophagus or colon, transitioning the overtube to a rigid state comprises transitioning the overtube to a rigid state in a configuration enabling access to the lesion or cancer, and forming a tissue fold comprises forming at least one tissue fold with a plication device advanced through, or coupled to, the overtube, so that the lesion or cancer is disposed on the tissue fold.

17. The method of claim 16 further comprising removing the lesion or cancer.

18. The method of claim 17, wherein removing the lesion or cancer further comprises removing the lesion or cancer with cutting apparatus.

19. The method of claim 18, wherein removing the lesion or cancer with cutting apparatus further comprises removing the lesion or cancer with a snare.

20. The method of claim 1, wherein the medical procedure comprises endoscopically treating a bleeding site within a patient's gastrointestinal tract, advancing the overtube within a hollow body organ comprises advancing the overtube through the patient's esophagus or colon, transitioning the overtube to a rigid state comprises transitioning the overtube to a rigid state in a configuration enabling access to the bleeding site, and forming a tissue fold comprises forming at least one tissue fold with a plication device advanced through, or coupled to, the overtube, so that the bleeding site is disposed on the tissue fold.

21. The method of claim 20 further comprising securing the tissue fold, thereby reducing bleeding from the bleeding site.

22. The method of claim 21, wherein securing the tissue fold further comprises securing the tissue fold with an anchor assembly.

* * * * *